United States Patent [19]

Braun, III et al.

[11] Patent Number: 5,792,937
[45] Date of Patent: Aug. 11, 1998

[54] PLANTS RESISTANT TO INFECTION BY PVX

[75] Inventors: Carl Joseph Braun, III, Creve Coeur; Cynthia Lou Hemenway, St. Louis; Nilgun Ereken Tumer, Chesterfield, all of Mo.

[73] Assignee: Monsanto Company, St. Louis, Mo.

[21] Appl. No.: 803,972

[22] Filed: Feb. 21, 1997

Related U.S. Application Data

[63] Continuation of Ser. No. 804,862, Dec. 6, 1991, abandoned, which is a continuation-in-part of Ser. No. 771,912, Oct. 4, 1991, abandoned.

[51] Int. Cl.[6] .............................. A01H 5/00; C12N 5/10; C12N 15/63; C12N 15/82
[52] U.S. Cl. .................. 800/205; 800/200; 800/DIG. 40; 800/DIG. 42; 800/DIG. 44; 435/172.1; 435/172.3; 435/320.1; 435/375; 435/417; 536/23.72; 536/24.1
[58] Field of Search .......................... 435/172.3, 320.1, 435/375, 69.1, 70.1, 91.1, 172.1, 235.1, 236, 237, 430; 800/205, DIG. 40, 42–44

[56] References Cited

U.S. PATENT DOCUMENTS 5,580,716  12/1996  Johnston et al. ................ 435/5
5,633,449  5/1997   Zaitlin et al. .................. 800/205

OTHER PUBLICATIONS

M. Huiswan et al. J. Gen. Vivol. 69:1789–98, 1988.

D. Ow et al. PNAS 84:4870–74, 1987.

Primary Examiner—Charles C. P. Rories
Attorney, Agent, or Firm—Grace L. Bonner; Arnold, White & Durkee

[57] ABSTRACT

A DNA sequence encoding a PVX replicase gene obtained from ORF1 of a PVX genome is provided. A plant gene containing the PVX replicase coding region is also provided as is a truncated derivative of the PVX replicase gene. A PVX replicase gene is inserted into a plant to confer resistance to the plant against PVX infection when the PVX replicase gene is sufficiently expressed.

8 Claims, 28 Drawing Sheets

```
              10                  30                  50
               .                   .                   .
       GAAAACTAAACCATACACCACCAACACAACCAAACCCACCACGCCCAATTGTTACACACC
       ---------+---------+---------+---------+---------+---------+

70                  90                 110
               .                   .                   .
       CGCTTGAAAAAGCAAGTCTGACAAATGGCCAAAGTGCGCGAGGTTTACCAATCCTTTACA
       ---------+---------+---------+---------+---------+---------+
                                    MetAlaLysValArgGluValTyrGlnSerPheThr 130                 150                 170
               .                   .                   .
       GACTCCACCACAAAAACTCTCATCCAAGATGAGGCTTATAGAAATATTCGTCCCATCATG
       ---------+---------+---------+---------+---------+---------+
       AspSerThrThrLysThrLeuIleGlnAspGluAlaTyrArgAsnIleArgProIleMet 190                 210                 230
               .                   .                   .
       GAAAAACATAAACTAGCTAACCCGTACGCTCAAACGGTTGAAGCGGCTAATGATCTAGAG
       ---------+---------+---------+---------+---------+---------+
       GluLysHisLysLeuAlaAsnProTyrAlaGlnThrValGluAlaAlaAsnAspLeuGlu 250                 270                 290
               .                   .                   .
       GGGTTCGGCATAGCCACCAATCCCTATAGCATTGAGTTGCATACACATGCAGCTGCTAAG
       ---------+---------+---------+---------+---------+---------+
       GlyPheGlyIleAlaThrAsnProTyrSerIleGluLeuHisThrHisAlaAlaAlaLys 310                 330                 350
               .                   .                   .
       ACCATAGAGAATAAACTTCTAGAGGTGCTTGGTTCCATCCTACCACAAGAACCTGTTACA
       ---------+---------+---------+---------+---------+---------+
       ThrIleGluAsnLysLeuLeuGluValLeuGlySerIleLeuProGlnGluProValThr 370                 390                 410
               .                   .                   .
       TTTATGTTCCTTAAACCCAGGAAGCTAAACTACATGAGAAGAAACCCGCGGATCAAGGAC
       ---------+---------+---------+---------+---------+---------+
       PheMetPheLeuLysProArgLysLeuAsnTyrMetArgArgAsnProArgIleLysAsp 430                 450                 470
               .                   .                   .
       ATTTTCCACAATGTTGCCATTGAACCGAGAGACGTAGCAAGGTACCCCAAGGAAACAATA
       ---------+---------+---------+---------+---------+---------+
       IlePheHisAsnValAlaIleGluProArgAspValAlaArgTyrProLysGluThrIle 490                 510                 530
               .                   .                   .
       ATTGACAAACTCACAGAGATCACAACAGACACAGCATACATTAGTGACACTCTGCACTTC
       ---------+---------+---------+---------+---------+---------+
       IleAspLysLeuThrGluIleThrThrAspThrAlaTyrIleSerAspThrLeuHisPhe
```

FIG. 1A

```
            550                  570                 590
    TTGGATCCGAGCTACATAGTGGAGACATTCCAAAACTGCCCAAAACTGCAAACATTGTAT
    ---------+---------+---------+---------+---------+---------+
    LeuAspProSerTyrIleValGluThrPheGlnAsnCysProLysLeuGlnThrLeuTyr 610                  630                 650
    GCGACCTTAGTTCTCCCCGTTGAGGCAGCCTTCAAAATGGAAAGCACTCACCCGAACATA
    ---------+---------+---------+---------+---------+---------+
    AlaThrLeuValLeuProValGluAlaAlaPheLysMetGluSerThrHisProAsnIle 670                  690                 710
    TACAGCCTCAAATACTTCGGAGATGGTTTCCAGTATATACCAGGCAACCATGGTGGTGGA
    ---------+---------+---------+---------+---------+---------+
    TyrSerLeuLysTyrPheGlyAspGlyPheGlnTyrIleProGlyAsnHisGlyGlyGly 730                  750                 770
    GCGTACCATCATGAATTTGCTCATTTACAATGGCTCAAAGTGGGAAAGATCAAATGGAGG
    ---------+---------+---------+---------+---------+---------+
    AlaTyrHisHisGluPheAlaHisLeuGlnTrpLeuLysValGlyLysIleLysTrpArg 790                  810                 830
    GACCCCAAGGATAGCTTTCTCGGACATCTCAATTACACGACTGAGCAGGTTGAGATGCAC
    ---------+---------+---------+---------+---------+---------+
    AspProLysAspSerPheLeuGlyHisLeuAsnTyrThrThrGluGlnValGluMetHis 850                  870                 890
    ACAGTGACAGTGCAGTTGCAGGAATCGTTCGCGGCAAACCACTTGTACTGCATCAGGAGA
    ---------+---------+---------+---------+---------+---------+
    ThrValThrValGlnLeuGlnGluSerPheAlaAlaAsnHisLeuTyrCysIleArgArg 910                  930                 950
    GGAGATTTGCTCACACCGGAGGTGCGCACTTTTGGCCAACCTGACAGGTATGTGATTCCA
    ---------+---------+---------+---------+---------+---------+
    GlyAspLeuLeuThrProGluValArgThrPheGlyGlnProAspArgTyrValIlePro 970                  990                 1010
    CCACAGATCTTCCTCCCGAAAGTCCATAACTGCAAGAAGCCGATTCTTAAAAAAACTATG
    ---------+---------+---------+---------+---------+---------+
    ProGlnIlePheLeuProLysValHisAsnCysLysLysProIleLeuLysLysThrMet 1030                 1050                1070
    ATGCAGCTCTTCTTGTATGTTAGGACAGTTAAGGTCGCAAAAAATTGTGACATTTTTGCC
    ---------+---------+---------+---------+---------+---------+
    MetGlnLeuPheLeuTyrValArgThrValLysValAlaLysAsnCysAspIlePheAla
```

FIG. 1B

```
              1090                    1110                    1130
                .                       .                       .
    AAAGTCAGACAATTAATTAAATCATCTGACCTGGACAAATATTCTGCTGTGGAACTGGTT
    ---------+---------+---------+---------+---------+---------+
    LysValArgGlnLeuIleLysSerSerAspLeuAspLysTyrSerAlaValGluLeuVal 1150                    1170                    1190
                .                       .                       .
    TACTTAGTAAGCTATATGGAGTTCCTTGCCGATCTACAAGCTACCACCTGCTTCTCAGAC
    ---------+---------+---------+---------+---------+---------+
    TyrLeuValSerTyrMetGluPheLeuAlaAspLeuGlnAlaThrThrCysPheSerAsp 1210                    1230                    1250
                .                       .                       .
    ACACTTTCTGGTGGCTTACTAACAAAGACCCTTGCACCGGTGAGGGCTTGGATACAAGAG
    ---------+---------+---------+---------+---------+---------+
    ThrLeuSerGlyGlyLeuLeuThrLysThrLeuAlaProValArgAlaTrpIleGlnGlu 1270                    1290                    1310
                .                       .                       .
    AAAAAGATGCAGCTGTTTGGTCTTGAGGACTACGCGAAGTTAGTCAAAGCAGTTGATTTC
    ---------+---------+---------+---------+---------+---------+
    LysLysMetGlnLeuPheGlyLeuGluAspTyrAlaLysLeuValLysAlaValAspPhe 1330                    1350                    1370
                .                       .                       .
    CACCCAGTGGATTTTTCTTTTAAAGTTGAAACTTGGGACTTCAGATTCCACCCCTTGCAA
    ---------+---------+---------+---------+---------+---------+
    HisProValAspPheSerPheLysValGluThrTrpAspPheArgPheHisProLeuGln 1390                    1410                    1430
                .                       .                       .
    GCGTGGAAAGCCTTCCGACCAAGGGAAGTGTCGGATGTAGAGGAAATGGAAAGTTTGTTC
    ---------+---------+---------+---------+---------+---------+
    AlaTrpLysAlaPheArgProArgGluValSerAspValGluGluMetGluSerLeuPhe 1450                    1470                    1490
                .                       .                       .
    TCAGATGGGGACCTGCTTGACTGCTTCACAAGAATGCCAGCTTATGCAGTAAACGCAGAG
    ---------+---------+---------+---------+---------+---------+
    SerAspGlyAspLeuLeuAspCysPheThrArgMetProAlaTyrAlaValAsnAlaGlu 1510                    1530                    1550
                .                       .                       .
    GAAGATTTAGCTACAATCAGGAAAACGCCCGAGATGGATGTCGGTCAAGAAGCCAAAGAA
    ---------+---------+---------+---------+---------+---------+
    GluAspLeuAlaThrIleArgLysThrProGluMetAspValGlyGlnGluAlaLysGlu 1570                    1590                    1610
                .                       .                       .
    CCTGCAGGAGACAGAAATCAATACTTAAACCCTGCAGAAACTTTCCTCAACAAGCTCCAC
    ---------+---------+---------+---------+---------+---------+
    ProAlaGlyAspArgAsnGlnTyrLeuAsnProAlaGluThrPheLeuAsnLysLeuHis
```

FIG. 1C

```
                1630              1650              1670
        AGGAAACACAGTAGGGAGGTGAAACATCAGGCCGTAAAGAAAGCTAAACGCCTAGCTGAA
        ---------+---------+---------+---------+---------+---------+
        ArgLysHisSerArgGluValLysHisGlnAlaValLysLysAlaLysArgLeuAlaGlu 1690              1710              1730
        ATCCAGGAGTCCATGAGAGCTGAGGGTGAGGCCGAACTAAATGAGATGAGCGGGGGCATG
        ---------+---------+---------+---------+---------+---------+
        IleGlnGluSerMetArgAlaGluGlyGluAlaGluLeuAsnGluMetSerGlyGlyMet 1750              1770              1790
        AGGGCAATACCTAGCAACGCAGAACTTCCCAGCACGAACGATGCTAGACAAGAACTCACA
        ---------+---------+---------+---------+---------+---------+
        ArgAlaIleProSerAsnAlaGluLeuProSerThrAsnAspAlaArgGlnGluLeuThr 1810              1830              1850
        CTCCCAACCACTAAACCTGTCCCTGCAAGGTGGGAAGATGCTTCATTCACAGATTCTAGT
        ---------+---------+---------+---------+---------+---------+
        LeuProThrThrLysProValProAlaArgTrpGluAspAlaSerPheThrAspSerSer 1870              1890              1910
        GTGAAAGAGGAGCAAGTGAAACTCCCTGGAAAAGAAGCCGTTGAGACAGCGACGCAACAA
        ---------+---------+---------+---------+---------+---------+
        ValLysGluGluGlnValLysLeuProGlyLysGluAlaValGluThrAlaThrGlnGln 1930              1950              1970
        GTCATAGAAGGACTCCCTTGGAAACACTGGATTCCTCAACTAAATGCTGTTGGATTCAAG
        ---------+---------+---------+---------+---------+---------+
        ValIleGluGlyLeuProTrpLysHisTrpIleProGlnLeuAsnAlaValGlyPheLys 1990              2010              2030
        GCGCTGGAAATTCAGAGGGATAGGAGTGGGACAATGATCATGCCCATCACAGAAATGGTC
        ---------+---------+---------+---------+---------+---------+
        AlaLeuGluIleGlnArgAspArgSerGlyThrMetIleMetProIleThrGluMetVal 2050              2070              2090
        TCCGGGTTGGAAAAAGAGGACTTCCCGGAAGGAACTCCAAAAGAGTTGGCACGAGAATTG
        ---------+---------+---------+---------+---------+---------+
        SerGlyLeuGluLysGluAspPheProGluGlyThrProLysGluLeuAlaArgGluLeu 2110              2130              2150
        CTCGCTATGAACAGAAGCCCTGCCACCATTCCTTTGGACCTGCTTAGAGCCAGAGACTAC
        ---------+---------+---------+---------+---------+---------+
        LeuAlaMetAsnArgSerProAlaThrIleProLeuAspLeuLeuArgAlaArgAspTyr
```

FIG. 1D

```
        2170                    2190                    2210
          .                       .                       .
   GGCAGTGATGTGAAGAACAAGAGAATTGGTGCCATCACAAAGACACAAGCAACAAGTTGG
   ---------+---------+---------+---------+---------+---------+
   GlySerAspValLysAsnLysArgIleGlyAlaIleThrLysThrGlnAlaThrSerTrp 2230                    2250                    2270
          .                       .                       .
   GGCGAGTACCTAACAGGAAAGATAGAAAGTCTGACTGAGAGGAAAGTTGCGACTTGTGTC
   ---------+---------+---------+---------+---------+---------+
   GlyGluTyrLeuThrGlyLysIleGluSerLeuThrGluArgLysValAlaThrCysVal 2290                    2310                    2330
          .                       .                       .
   ATTCATGGAGCTGGAGGCTCTGGGAAAAGTCATGCCATCCAGAAGGCATTGAGAGAAATT
   ---------+---------+---------+---------+---------+---------+
   IleHisGlyAlaGlyGlySerGlyLysSerHisAlaIleGlnLysAlaLeuArgGluIle 2350                    2370                    2390
          .                       .                       .
   GGCAAGGGGTCAGACATCACTGTAGTCCTGCCGACCAATGAACTGCGACTAGATTGGAGC
   ---------+---------+---------+---------+---------+---------+
   GlyLysGlySerAspIleThrValValLeuProThrAsnGluLeuArgLeuAspTrpSer 2410                    2430                    2450
          .                       .                       .
   AAGAAAGTGCCTAACACTGAACCATATATGTTCAAGACCTATGAAAAGGCATTAATTGGG
   ---------+---------+---------+---------+---------+---------+
   LysLysValProAsnThrGluProTyrMetPheLysThrTyrGluLysAlaLeuIleGly 2470                    2490                    2510
          .                       .                       .
   GGAACAGGCAGTATAGTCATCTTTGACGATTACTCAAAACTTCCTCCCGGTTACATAGAA
   ---------+---------+---------+---------+---------+---------+
   GlyThrGlySerIleValIlePheAspAspTyrSerLysLeuProProGlyTyrIleGlu 2530                    2550                    2570
          .                       .                       .
   GCCTTAATCTGTTTCTACTCTAAAATCAAGCTAGTCATTCTAACAGGAGATAGCAGACAG
   ---------+---------+---------+---------+---------+---------+
   AlaLeuIleCysPheTyrSerLysIleLysLeuValIleLeuThrGlyAspSerArgGln 2590                    2610                    2630
          .                       .                       .
   AGCGTCTACCATGAAACTGCTGAGGACGCCTCCATCAGGCATTTGGGACCAGCGACAGAG
   ---------+---------+---------+---------+---------+---------+
   SerValTyrHisGluThrAlaGluAspAlaSerIleArgHisLeuGlyProAlaThrGlu 2650                    2670                    2690
          .                       .                       .
   TACTTCTCAAAATACTGCCGATACTATCTCAATGCTACACACCGCAACAAGAAAGACCTT
   ---------+---------+---------+---------+---------+---------+
   TyrPheSerLysTyrCysArgTyrTyrLeuAsnAlaThrHisArgAsnLysLysAspLeu
```

FIG. 1E

```
                2710                2730                 2750
        GCGAACATGCTCGGTGTCTACAGTGAGAGAACGGGGGTCACCGAAATCAGCATGAGCGCC
        --------+---------+---------+---------+---------+---------+
        AlaAsnMetLeuGlyValTyrSerGluArgThrGlyValThrGluIleSerMetSerAla 2770                2790                 2810
        GAGTTCTTAGAAGGAATCCCAACTTTAGTACCCTCGGATGAGAAGAGAAAGCTGTACATG
        --------+---------+---------+---------+---------+---------+
        GluPheLeuGluGlyIleProThrLeuValProSerAspGluLysArgLysLeuTyrMet 2830                2850                 2870
        GGCACCGGGAGGAACGACACGTTCACATACGCTGGATGCCAGGGGCTGACCAAGCCGAAA
        --------+---------+---------+---------+---------+---------+
        GlyThrGlyArgAsnAspThrPheThrTyrAlaGlyCysGlnGlyLeuThrLysProLys 2890                2910                 2930
        GTACAAATAGTGTTGGACCACAACACCCAAGTGTGTAGCGCGAATGTGATGTACACGGCA
        --------+---------+---------+---------+---------+---------+
        ValGlnIleValLeuAspHisAsnThrGlnValCysSerAlaAsnValMetTyrThrAla 2950                2970                 2990
        CTTTCTAGAGCCACCGACAGGATTCACTTCGTGAACACAAGTGCAAACTCTTCGGCCTTC
        --------+---------+---------+---------+---------+---------+
        LeuSerArgAlaThrAspArgIleHisPheValAsnThrSerAlaAsnSerSerAlaPhe 3010                3030                 3050
        TGGGAAAAGTTAGACAGCACCCCTTATCTCAAGACTTTCCTATCAGTGGTGAGAGAACAA
        --------+---------+---------+---------+---------+---------+
        TrpGluLysLeuAspSerThrProTyrLeuLysThrPheLeuSerValValArgGluGln 3070                3090                 3110
        GCACTCAGGGAGTACGAGCCGGCAGAGGCAGAGCCAATTCGAGAGCCTGAGCCCCAGACA
        --------+---------+---------+---------+---------+---------+
        AlaLeuArgGluTyrGluProAlaGluAlaGluProIleArgGluProGluProGlnThr 3130                3150                 3170
        CACATGTGTGTCGAGAATGAGGAGTCCGTGCTAGAAGAGTACAAAGAGGAACTCTTGGAA
        --------+---------+---------+---------+---------+---------+
        HisMetCysValGluAsnGluGluSerValLeuGluGluTyrLysGluGluLeuLeuGlu 3190                3210                 3230
        AAGTTTGACAGAGAGATCCACTCGGAATCCCATGGTCATTCAAACTGTGTCCAAACAGAA
        --------+---------+---------+---------+---------+---------+
        LysPheAspArgGluIleHisSerGluSerHisGlyHisSerAsnCysValGlnThrGlu
```

FIG. 1F

```
         3790                3810                3830
             .                   .                   .
AATTTCGGCAGACCTAGCTTGGCCAATGACTACACAGCTTTCGACCAGTCTCAGGATGGA
---------+---------+---------+---------+---------+---------+
AsnPheGlyArgProSerLeuAlaAsnAspTyrThrAlaPheAspGlnSerGlnAspGly 3850                3870                3890
             .                   .                   .
GCTATGCTGCAATTTGAGGTGCTCAAAGCCAAGCACCATTGCATACCAGAGGAAATCATC
---------+---------+---------+---------+---------+---------+
AlaMetLeuGlnPheGluValLeuLysAlaLysHisHisCysIleProGluGluIleIle 3910                3930                3950
             .                   .                   .
CAAGCATACATAGACATTAAGACCAATGCACAGATTTTCCTAGGCACATTGTCAATCATG
---------+---------+---------+---------+---------+---------+
GlnAlaTyrIleAspIleLysThrAsnAlaGlnIlePheLeuGlyThrLeuSerIleMet 3970                3990                4010
             .                   .                   .
CGCCTGACTGGTGAGGGTCCCACTTTTGATGCAAACACTGAGTGCAACATAGCTTACACC
---------+---------+---------+---------+---------+---------+
ArgLeuThrGlyGluGlyProThrPheAspAlaAsnThrGluCysAsnIleAlaTyrThr 4030                4050                4070
             .                   .                   .
CATACAAAGTTTGACATCCCAGCAGGAACTGCTCAAGTTTATGCAGGAGACGACTCAGCA
---------+---------+---------+---------+---------+---------+
HisThrLysPheAspIleProAlaGlyThrAlaGlnValTyrAlaGlyAspAspSerAla 4090                4110                4130
             .                   .                   .
CTGGATTGCGTTCCAGAAGTGAAGCATAGCTTCCACAGGCTTGAAGACAAACTACTCCTT
---------+---------+---------+---------+---------+---------+
LeuAspCysValProGluValLysHisSerPheHisArgLeuGluAspLysLeuLeuLeu 4150                4170                4190
             .                   .                   .
AAGTCAAAGCCCGTAATCACGCAGCAAAAGAAAGGCAGTTGGCCTGAGTTTTGTGGTTGG
---------+---------+---------+---------+---------+---------+
LysSerLysProValIleThrGlnGlnLysLysGlySerTrpProGluPheCysGlyTrp 4210                4230                4250
             .                   .                   .
CTGATTACACCAAAAGGGGTAATGAAAGACCCAATTAAGCTCCATGTTAGCTTAAAATTG
---------+---------+---------+---------+---------+---------+
LeuIleThrProLysGlyValMetLysAspProIleLysLeuHisValSerLeuLysLeu 4270                4290                4310
             .                   .                   .
GCCGAAGCTAAGGGCGAACTCAAGAAATGTCAAGACTCCTATGAAATTGATCTGAGTTAT
---------+---------+---------+---------+---------+---------+
AlaGluAlaLysGlyGluLeuLysLysCysGlnAspSerTyrGluIleAspLeuSerTyr
```

FIG. 1G

```
             3790               3810              3830
              .                  .                 .
      AATTTCGGCAGACCTAGCTTGGCCAATGACTACACAGCTTTCGACCAGTCTCAGGATGGA
      ---------+---------+---------+---------+---------+---------+
      AsnPheGlyArgProSerLeuAlaAsnAspTyrThrAlaPheAspGlnSerGlnAspGly 3850               3870              3890
              .                  .                 .
      GCTATGCTGCAATTTGAGGTGCTCAAAGCCAAGCACCATTGCATACCAGAGGAAATCATC
      ---------+---------+---------+---------+---------+---------+
      AlaMetLeuGlnPheGluValLeuLysAlaLysHisHisCysIleProGluGluIleIle 3910               3930              3950
              .                  .                 .
      CAAGCATACATAGACATTAAGACCAATGCACAGATTTTCCTAGGCACATTGTCAATCATG
      ---------+---------+---------+---------+---------+---------+
      GlnAlaTyrIleAspIleLysThrAsnAlaGlnIlePheLeuGlyThrLeuSerIleMet 3970               3990              4010
              .                  .                 .
      CGCCTGACTGGTGAGGGTCCCACTTTTGATGCAAACACTGAGTGCAACATAGCTTACACC
      ---------+---------+---------+---------+---------+---------+
      ArgLeuThrGlyGluGlyProThrPheAspAlaAsnThrGluCysAsnIleAlaTyrThr 4030               4050              4070
              .                  .                 .
      CATACAAAGTTTGACATCCCAGCAGGAACTGCTCAAGTTTATGCAGGAGACGACTCAGCA
      ---------+---------+---------+---------+---------+---------+
      HisThrLysPheAspIleProAlaGlyThrAlaGlnValTyrAlaGlyAspAspSerAla 4090               4110              4130
              .                  .                 .
      CTGGATTGCGTTCCAGAAGTGAAGCATAGCTTCCACAGGCTTGAAGACAAACTACTCCTT
      ---------+---------+---------+---------+---------+---------+
      LeuAspCysValProGluValLysHisSerPheHisArgLeuGluAspLysLeuLeuLeu 4150               4170              4190
              .                  .                 .
      AAGTCAAAGCCCGTAATCACGCAGCAAAAGAAAGGCAGTTGGCCTGAGTTTTGTGGTTGG
      ---------+---------+---------+---------+---------+---------+
      LysSerLysProValIleThrGlnGlnLysLysGlySerTrpProGluPheCysGlyTrp 4210               4230              4250
              .                  .                 .
      CTGATTACACCAAAAGGGGTAATGAAAGACCCAATTAAGCTCCATGTTAGCTTAAAATTG
      ---------+---------+---------+---------+---------+---------+
      LeuIleThrProLysGlyValMetLysAspProIleLysLeuHisValSerLeuLysLeu 4270               4290              4310
              .                  .                 .
      GCCGAAGCTAAGGGCGAACTCAAGAAATGTCAAGACTCCTATGAAATTGATCTGAGTTAT
      ---------+---------+---------+---------+---------+---------+
      AlaGluAlaLysGlyGluLeuLysLysCysGlnAspSerTyrGluIleAspLeuSerTyr
```

FIG. 1H

```
            4330                    4350                    4370
GCCTACGACCACAAGGACTCTCTGCATGACTTGTTCGATGAGAAACAGTGTCAGGCACAT
---------+---------+---------+---------+---------+---------+
AlaTyrAspHisLysAspSerLeuHisAspLeuPheAspGluLysGlnCysGlnAlaHis 4390                    4410                    4430
ACACTCACTTGCAGAACACTGATCAAGTCAGGGAGAGGCACTGTCTCACTTCCCCGCCTC
---------+---------+---------+---------+---------+---------+
ThrLeuThrCysArgThrLeuIleLysSerGlyArgGlyThrValSerLeuProArgLeu

4450
AGAAACTTTCTTTAA
---------+-----
ArgAsnPheLeuEnd
```

FIG. 1I

```
         10              30              50
          .               .               .
     GAAAACTAAACCATACACCACCAACACAACCAAACCCACCACGCCCAATTGTTACACACC
     ---------+---------+---------+---------+---------+---------+

70              90              110
          .               .               .
     CGCTTGAAAAAGCAAGTCTGACAAATGGCCAAAGTGCGCGAGGTTTACCAATCCTTTACA
     ---------+---------+---------+---------+---------+---------+
                                    MetAlaLysValArgGluValTyrGlnSerPheThr 130             150             170
          .               .               .
     GACTCCACCACAAAAACTCTCATCCAAGATGAGGCTTATAGAAATATTCGTCCCATCATG
     ---------+---------+---------+---------+---------+---------+
     AspSerThrThrLysThrLeuIleGlnAspGluAlaTyrArgAsnIleArgProIleMet 190             210             230
          .               .               .
     GAAAAACATAAACTAGCTAACCCGTACGCTCAAACGGTTGAAGCGGCTAATGATCTAGAG
     ---------+---------+---------+---------+---------+---------+
     GluLysHisLysLeuAlaAsnProTyrAlaGlnThrValGluAlaAlaAsnAspLeuGlu 250             270             290
          .               .               .
     GGGTTCGGCATAGCCACCAATCCCTATAGCATTGAGTTGCATACACATGCAGCTGCTAAG
     ---------+---------+---------+---------+---------+---------+
     GlyPheGlyIleAlaThrAsnProTyrSerIleGluLeuHisThrHisAlaAlaAlaLys 310             330             350
          .               .               .
     ACCATAGAGAATAAACTTCTAGAGGTGCTTGGTTCCATCCTACCACAAGAACCTGTTACA
     ---------+---------+---------+---------+---------+---------+
     ThrIleGluAsnLysLeuLeuGluValLeuGlySerIleLeuProGlnGluProValThr 370             390             410
          .               .               .
     TTTATGTTCCTTAAACCCAGGAAGCTAAACTACATGAGAAGAAACCCGCGGATCAAGGAC
     ---------+---------+---------+---------+---------+---------+
     PheMetPheLeuLysProArgLysLeuAsnTyrMetArgArgAsnProArgIleLysAsp 430             450             470
          .               .               .
     ATTTTCCACAATGTTGCCATTGAACCGAGAGACGTAGCAAGGTACCCCAAGGAAACAATA
     ---------+---------+---------+---------+---------+---------+
     IlePheHisAsnValAlaIleGluProArgAspValAlaArgTyrProLysGluThrIle 490             510             530
          .               .               .
     ATTGACAAACTCACAGAGATCACAACAGACACAGCATACATTAGTGACACTCTGCACTTC
     ---------+---------+---------+---------+---------+---------+
     IleAspLysLeuThrGluIleThrThrAspThrAlaTyrIleSerAspThrLeuHisPhe 550             570             590
          .               .               .
     TTGGATCCGAGCTACATAGTGGAGACATTCCAAAACTGCCCAAAACTGCAAACATTGTAT
```

FIG. 2A

```
                                          LeuAspProSerTyrIleValGluThrPheGlnAsnCysProLysLeuGlnThrLeuTyr
           610              630              650
GCGACCTTAGTTCTCCCCGTTGAGGCAGCCTTCAAAATGGAAAGCACTCACCCGAACATA
AlaThrLeuValLeuProValGluAlaAlaPheLysMetGluSerThrHisProAsnIle
           670              690              710
TACAGCCTCAAATACTTCGGAGATGGTTTCCAGTATATACCAGGCAACCATGGTGGTGGA
TyrSerLeuLysTyrPheGlyAspGlyPheGlnTyrIleProGlyAsnHisGlyGlyGly
           730              750              770
GCGTACCATCATGAATTTGCTCATTTACAATGGCTCAAAGTGGGAAAGATCAAATGGAGG
AlaTyrHisHisGluPheAlaHisLeuGlnTrpLeuLysValGlyLysIleLysTrpArg
           790              810              830
GACCCCAAGGATAGCTTTCTCGGACATCTCAATTACACGACTGAGCAGGTTGAGATGCAC
AspProLysAspSerPheLeuGlyHisLeuAsnTyrThrThrGluGlnValGluMetHis
           850              870              890
ACAGTGACAGTGCAGTTGCAGGAATCGTTCGCGGCAAACCACTTGTACTGCATCAGGAGA
ThrValThrValGlnLeuGlnGluSerPheAlaAlaAsnHisLeuTyrCysIleArgArg
           910              930              950
GGAGATTTGCTCACACCGGAGGTGCGCACTTTTGGCCAACCTGACAGGTATGTGATTCCA
GlyAspLeuLeuThrProGluValArgThrPheGlyGlnProAspArgTyrValIlePro
           970              990              1010
CCACAGATCTTCCTCCCGAAAGTCCATAACTGCAAGAAGCCGATTCTTAAAAAAACTATG
ProGlnIlePheLeuProLysValHisAsnCysLysLysProIleLeuLysLysThrMet
           1030             1050             1070
ATGCAGCTCTTCTTGTATGTTAGGACAGTTAAGGTCGCAAAAAATTGTGACATTTTTGCC
MetGlnLeuPheLeuTyrValArgThrValLysValAlaLysAsnCysAspIlePheAla
           1090             1110             1130
AAAGTCAGACAATTAATTAAATCATCTGACCTGGACAAATATTCTGCTGTGGAACTGGTT
LysValArgGlnLeuIleLysSerSerAspLeuAspLysTyrSerAlaValGluLeuVal
           1150             1170             1190
```

FIG. 2B

```
TACTTAGTAAGCTATATGGAGTTCCTTGCCGATCTACAAGCTACCACCTGCTTCTCAGAC
---------+---------+---------+---------+---------+---------+
TyrLeuValSerTyrMetGluPheLeuAlaAspLeuGlnAlaThrThrCysPheSerAsp
     1210          1230          1250

ACACTTTCTGGTGGCTTACTAACAAAGACCCTTGCACCGGTGAGGGCTTGGATACAAGAG
---------+---------+---------+---------+---------+---------+
ThrLeuSerGlyGlyLeuLeuThrLysThrLeuAlaProValArgAlaTrpIleGlnGlu
     1270          1290          1310

AAAAAGATGCAGCTGTTTGGTCTTGAGGACTACGCGAAGTTAGTCAAAGCAGTTGATTTC
---------+---------+---------+---------+---------+---------+
LysLysMetGlnLeuPheGlyLeuGluAspTyrAlaLysLeuValLysAlaValAspPhe
     1330          1350          1370

CACCCAGTGGATTTTTCTTTTAAAGTTGAAACTTGGGACTTCAGATTCCACCCCTTGCAA
---------+---------+---------+---------+---------+---------+
HisProValAspPheSerPheLysValGluThrTrpAspPheArgPheHisProLeuGln
     1390          1410          1430

GCGTGGAAAGCCTTCCGACCAAGGGAAGTGTCGGATGTAGAGGAAATGGAAAGTTTGTTC
---------+---------+---------+---------+---------+---------+
AlaTrpLysAlaPheArgProArgGluValSerAspValGluGluMetGluSerLeuPhe
     1450          1470          1490

TCAGATGGGGACCTGCTTGACTGCTTCACAAGAATGCCAGCTTATGCAGTAAACGCAGAG
---------+---------+---------+---------+---------+---------+
SerAspGlyAspLeuLeuAspCysPheThrArgMetProAlaTyrAlaValAsnAlaGlu
     1510          1530          1550

GAAGATTTAGCTACAATCAGGAAAACGCCCGAGATGGATGTCGGTCAAGAAGCCAAAGAA
---------+---------+---------+---------+---------+---------+
GluAspLeuAlaThrIleArgLysThrProGluMetAspValGlyGlnGluAlaLysGlu
     1570          1590          1610

CCTGCAGGAGACAGAAATCAATACTTAAACCCTGCAGAAACTTTCCTCAACAAGCTCCAC
---------+---------+---------+---------+---------+---------+
ProAlaGlyAspArgAsnGlnTyrLeuAsnProAlaGluThrPheLeuAsnLysLeuHis
     1630          1650          1670

AGGAAACACAGTAGGGAGGTGAAACATCAGGCCGTAAAGAAAGCTAAACGCCTAGCTGAA
---------+---------+---------+---------+---------+---------+
ArgLysHisSerArgGluValLysHisGlnAlaValLysLysAlaLysArgLeuAlaGlu
     1690          1710          1730

ATCCAGGAGTCCATGAGAGCTGAGGGTGAGGCCGAACTAAATGAGATGAGCGGGGGCATG
---------+---------+---------+---------+---------+---------+
IleGlnGluSerMetArgAlaGluGlyGluAlaGluLeuAsnGluMetSerGlyGlyMet
```

FIG. 2C

```
              1750                  1770                  1790
                .                    .                    .
       AGGGCAATACCTAGCAACGCAGAACTTCCCAGCACGAACGATGCTAGACAAGAACTCACA
       ---------+---------+---------+---------+---------+---------+
       ArgAlaIleProSerAsnAlaGluLeuProSerThrAsnAspAlaArgGlnGluLeuThr 1810                  1830                  1850
                .                    .                    .
       CTCCCAACCACTAAACCTGTCCCTGCAAGGTGGGAAGATGCTTCATTCACAGATTCTAGT
       ---------+---------+---------+---------+---------+---------+
       LeuProThrThrLysProValProAlaArgTrpGluAspAlaSerPheThrAspSerSer 1870                  1890                  1910
                .                    .                    .
       GTGAAAGAGGAGCAAGTGAAACTCCCTGGAAAAGAAGCCGTTGAGACAGCGACGCAACAA
       ---------+---------+---------+---------+---------+---------+
       ValLysGluGluGlnValLysLeuProGlyLysGluAlaValGluThrAlaThrGlnGln 1930                  1950                  1970
                .                    .                    .
       GTCATAGAAGGACTCCCTTGGAAACACTGGATTCCTCAACTAAATGCTGTTGGATTCAAG
       ---------+---------+---------+---------+---------+---------+
       ValIleGluGlyLeuProTrpLysHisTrpIleProGlnLeuAsnAlaValGlyPheLys 1990                  2010                  2030
                .                    .                    .
       GCGCTGGAAATTCAGAGGGATAGGAGTGGGACAATGATCATGCCCATCACAGAAATGGTC
       ---------+---------+---------+---------+---------+---------+
       AlaLeuGluIleGlnArgAspArgSerGlyThrMetIleMetProIleThrGluMetVal 2050                  2070                  2090
                .                    .                    .
       TCCGGGTTGGAAAAAGAGGACTTCCCGGAAGGAACTCCAAAAGAGTTGGCACGAGAATTG
       ---------+---------+---------+---------+---------+---------+
       SerGlyLeuGluLysGluAspPheProGluGlyThrProLysGluLeuAlaArgGluLeu

CTCGCTAAGAGCTC
       ------
       LeuAla
```

FIG. 2D

Systemic levels of PVX in plants challenged with a 5.0 ug/ml inoculum

Legend:
- □ samsun (control)
- ○ 30205
- ● 30199
- ▲ 30219
- ✦ 29436

Y-axis: PVX antigen levels (ng/mg of fresh weight tissue)
X-axis: days post infection

FIG. 7

PVX antigen levels in inoculated
leaves challenged with 0.5 ug/ml inoculum

Legend:
- samsun (control)
- 30205
- 30199
- 30219
- 29436

FIG. 8

```
                SspI
                ------
       TCATCAAAATATTTAGCAGCATTCCAGATTGGGTTCAATCAACAAGGTACGAGCCATATC
 6358  --+----------+----------+----------+----------+----------+-------  6417
       AGTAGTTTTATAAATCGTCGTAAGGTCTAACCCAAGTTAGTTGTTCCATGCTCGGTATAG

ACTTTATTCAAATTGGTATCGCCAAAACCAAGAAGGAACTCCCATCCTCAAAGGTTTGTA
 6418  --+----------+----------+----------+----------+----------+-------  6477
       TGAAATAAGTTTAACCATAGCGGTTTTGGTTCTTCCTTGAGGGTAGGAGTTTCCAAACAT

AGGAAGAATTCTCAGTCCAAAGCCTCAACAAGGTCAGGGTACAGAGTCTCCAAACCATTA
 6478  --+----------+----------+----------+----------+----------+-------  6537
       TCCTTCTTAAGAGTCAGGTTTCGGAGTTGTTCCAGTCCCATGTCTCAGAGGTTTGGTAAT

GCCAAAAGCTACAGGAGATCAATGAAGAATCTTCAATCAAAGTAAACTACTGTTCCAGCA
 6538  --+----------+----------+----------+----------+----------+-------  6597
       CGGTTTTCGATGTCCTCTAGTTACTTCTTAGAAGTTAGTTTCATTTGATGACAAGGTCGT

CATGCATCATGGTCAGTAAGTTTCAGAAAAGACATCCACCGAAGACTTAAAGTTAGTGG
 6598  --+----------+----------+----------+----------+----------+-------  6657
       GTACGTAGTACCAGTCATTCAAAGTCTTTTTCTGTAGGTGGCTTCTGAATTTCAATCACC

GCATCTTTGAAAGTAATCTTGTCAACATCGAGCAGCTGGCTTGTGGGACCAGACAAAAA
       GCCAAAAGCTACAGGAGATCAATGAAGAATCTTCAATCAAAGTAAACTACTGTTCCAGCA
 6538  --+----------+----------+----------+----------+----------+-------  6597
       CGGTTTTCGATGTCCTCTAGTTACTTCTTAGAAGTTAGTTTCATTTGATGACAAGGTCGT

CATGCATCATGGTCAGTAAGTTTCAGAAAAGACATCCACCGAAGACTTAAAGTTAGTGG
 6598  --+----------+----------+----------+----------+----------+-------  6657
       GTACGTAGTACCAGTCATTCAAAGTCTTTTTCTGTAGGTGGCTTCTGAATTTCAATCACC

GCATCTTTGAAAGTAATCTTGTCAACATCGAGCAGCTGGCTTGTGGGACCAGACAAAAA
 6658  --+----------+----------+----------+----------+----------+-------  6717
       CGTAGAAACTTTCATTAGAACAGTTGTAGCTCGTCGACCGAACACCCCTGGTCTGTTTTT

AGGAATGGTGCAGAATTGTTAGGCGCACCTACCAAAAGCATCTTTGCCTTTATTGCAAAG
 6718  --+----------+----------+----------+----------+----------+-------  6777
       TCCTTACCACGTCTTAACAATCCGCGTGGATGGTTTTCGTAGAAACGGAAATAACGTTTC

ATAAAGCAGATTCCTCTAGTACAAGTGGGGAACAAAATAACGTGGAAAAGAGCTGTCCTG
 6778  --+----------+----------+----------+----------+----------+-------  6837
       TATTTCGTCTAAGGAGATCATGTTCACCCCTTGTTTTATTGCACCTTTTCTCGACAGGAC

ACAGCCCACTCACTAATGCGTATGACGAACGCAGTGACGACCACAAAAGAATTCCCTCTA
 6838  --+----------+----------+----------+----------+----------+-------  6897
       TGTCGGGTGAGTGATTACGCATACTGCTTGCGTCACTGCTGGTGTTTTCTTAAGGGAGAT
                                                                SspI
                                                                ------
       TATAAGAAGGCATTCATTCCCATTTGAAGGATCATCAGATACTAACCAATATTTCTC
 6898  --+----------+----------+----------+----------+----------+-----    6954
       ATATTCTTCCGTAAGTAAGGGTAAACTTCCTAGTAGTCTATGATTGGTTATAAAGAG
```

FIG. 12

```
        10                    30                    50
         .                     .                     .
GAAAACTAAACCATACACCACCAACACAACCAAACCCACCACGCCCAATTGTTACACACC
---------+---------+---------+---------+---------+---------+

70                    90                   110
         .                     .                     .
CGCTTGAAAAAGCAAGTCTGACAAATGGCCAAAGTGCGCGAGGTTTACCAATCCTTTACA
---------+---------+---------+---------+---------+---------+
                          MetAlaLysValArgGluValTyrGlnSerPheThr 130                   150                   170
         .                     .                     .
GACTCCACCACAAAAACTCTCATCCAAGATGAGGCTTATAGAAATATTCGTCCCATCATG
---------+---------+---------+---------+---------+---------+
AspSerThrThrLysThrLeuIleGlnAspGluAlaTyrArgAsnIleArgProIleMet 190                   210                   230
         .                     .                     .
GAAAAACATAAACTAGCTAACCCGTACGCTCAAACGGTTGAAGCGGCTAATGATCTAGAG
---------+---------+---------+---------+---------+---------+
GluLysHisLysLeuAlaAsnProTyrAlaGlnThrValGluAlaAlaAsnAspLeuGlu 250                   270                   290
         .                     .                     .
GGGTTCGGCATAGCCACCAATCCCTATAGCATTGAGTTGCATACACATGCAGCTGCTAAG
---------+---------+---------+---------+---------+---------+
GlyPheGlyIleAlaThrAsnProTyrSerIleGluLeuHisThrHisAlaAlaAlaLys 310                   330                   350
         .                     .                     .
ACCATAGAGAATAAACTTCTAGAGGTGCTTGGTTCCATCCTACCACAAGAACCTGTTACA
---------+---------+---------+---------+---------+---------+
ThrIleGluAsnLysLeuLeuGluValLeuGlySerIleLeuProGlnGluProValThr 370                   390                   410
         .                     .                     .
TTTATGTTCCTTAAACCCAGGAAGCTAAACTACATGAGAAGAAACCCGCGGATCAAGGAC
---------+---------+---------+---------+---------+---------+
PheMetPheLeuLysProArgLysLeuAsnTyrMetArgArgAsnProArgIleLysAsp 430                   450                   470
         .                     .                     .
ATTTTCCACAATGTTGCCATTGAACCGAGAGACGTAGCAAGGTACCCCAAGGAAACAATA
---------+---------+---------+---------+---------+---------+
IlePheHisAsnValAlaIleGluProArgAspValAlaArgTyrProLysGluThrIle 490                   510                   530
         .                     .                     .
ATTGACAAACTCACAGAGATCACAACAGACACAGCATACATTAGTGACACTCTGCACTTC
---------+---------+---------+---------+---------+---------+
IleAspLysLeuThrGluIleThrThrAspThrAlaTyrIleSerAspThrLeuHisPhe
```

FIG. 13A

```
       550                  570                 590
TTGGATCCGAGCTACATAGTGGAGACATTCCAAAACTGCCCAAAACTGCAAACATTGTAT
---------+---------+---------+---------+---------+---------+
LeuAspProSerTyrIleValGluThrPheGlnAsnCysProLysLeuGlnThrLeuTyr 610                  630                 650
GCGACCTTAGTTCTCCCCGTTGAGGCAGCCTTCAAAATGGAAAGCACTCACCCGAACATA
---------+---------+---------+---------+---------+---------+
AlaThrLeuValLeuProValGluAlaAlaPheLysMetGluSerThrHisProAsnIle 670                  690                 710
TACAGCCTCAAATACTTCGGAGATGGTTTCCAGTATATACCAGGCAACCATGGTGGTGGA
---------+---------+---------+---------+---------+---------+
TyrSerLeuLysTyrPheGlyAspGlyPheGlnTyrIleProGlyAsnHisGlyGlyGly 730                  750                 770
GCGTACCATCATGAATTTGCTCATTTACAATGGCTCAAAGTGGGAAAGATCAAATGGAGG
---------+---------+---------+---------+---------+---------+
AlaTyrHisHisGluPheAlaHisLeuGlnTrpLeuLysValGlyLysIleLysTrpArg 790                  810                 830
GACCCCAAGGATAGCTTTCTCGGACATCTCAATTACACGACTGAGCAGGTTGAGATGCAC
---------+---------+---------+---------+---------+---------+
AspProLysAspSerPheLeuGlyHisLeuAsnTyrThrThrGluGlnValGluMetHis 850                  870                 890
ACAGTGACAGTGCAGTTGCAGGAATCGTTCGCGGCAAACCACTTGTACTGCATCAGGAGA
---------+---------+---------+---------+---------+---------+
ThrValThrValGlnLeuGlnGluSerPheAlaAlaAsnHisLeuTyrCysIleArgArg 910                  930                 950
GGAGATTTGCTCACACCGGAGGTGCGCACTTTTGGCCAACCTGACAGGTATGTGATTCCA
---------+---------+---------+---------+---------+---------+
GlyAspLeuLeuThrProGluValArgThrPheGlyGlnProAspArgTyrValIlePro 970                  990                1010
CCACAGATCTTCCTCCCGAAAGTCCATAACTGCAAGAAGCCGATTCTTAAAAAAACTATG
---------+---------+---------+---------+---------+---------+
ProGlnIlePheLeuProLysValHisAsnCysLysLysProIleLeuLysLysThrMet 1030                 1050                1070
ATGCAGCTCTTCTTGTATGTTAGGACAGTTAAGGTCGCAAAAAATTGTGACATTTTTGCC
---------+---------+---------+---------+---------+---------+
MetGlnLeuPheLeuTyrValArgThrValLysValAlaLysAsnCysAspIlePheAla
```

FIG. 13B

```
          1090                1110                1130
            .                   .                   .
AAAGTCAGACAATTAATTAAATCATCTGACCTGGACAAATATTCTGCTGTGGAACTGGTT
---------+---------+---------+---------+---------+---------+
LysValArgGlnLeuIleLysSerSerAspLeuAspLysTyrSerAlaValGluLeuVal 1150                1170                1190
            .                   .                   .
TACTTAGTAAGCTATATGGAGTTCCTTGCCGATCTACAAGCTACCACCTGCTTCTCAGAC
---------+---------+---------+---------+---------+---------+
TyrLeuValSerTyrMetGluPheLeuAlaAspLeuGlnAlaThrThrCysPheSerAsp 1210                1230                1250
            .                   .                   .
ACACTTTCTGGTGGCTTACTAACAAAGACCCTTGCACCGGTGAGGGCTTGGATACAAGAG
---------+---------+---------+---------+---------+---------+
ThrLeuSerGlyGlyLeuLeuThrLysThrLeuAlaProValArgAlaTrpIleGlnGlu 1270                1290                1310
            .                   .                   .
AAAAAGATGCAGCTGTTTGGTCTTGAGGACTACGCGAAGTTAGTCAAAGCAGTTGATTTC
---------+---------+---------+---------+---------+---------+
LysLysMetGlnLeuPheGlyLeuGluAspTyrAlaLysLeuValLysAlaValAspPhe 1330                1350                1370
            .                   .                   .
CACCCAGTGGATTTTTCTTTTAAAGTTGAAACTTGGGACTTCAGATTCCACCCCTTGCAA
---------+---------+---------+---------+---------+---------+
HisProValAspPheSerPheLysValGluThrTrpAspPheArgPheHisProLeuGln 1390                1410                1430
            .                   .                   .
GCGTGGAAAGCCTTCCGACCAAGGGAAGTGTCGGATGTAGAGGAAATGGAAAGTTTGTTC
---------+---------+---------+---------+---------+---------+
AlaTrpLysAlaPheArgProArgGluValSerAspValGluGluMetGluSerLeuPhe 1450                1470                1490
            .                   .                   .
TCAGATGGGGACCTGCTTGACTGCTTCACAAGAATGCCAGCTTATGCAGTAAACGCAGAG
---------+---------+---------+---------+---------+---------+
SerAspGlyAspLeuLeuAspCysPheThrArgMetProAlaTyrAlaValAsnAlaGlu 1510                1530                1550
            .                   .                   .
GAAGATTTAGCTACAATCAGGAAAACGCCCGAGATGGATGTCGGTCAAGAAGCCAAAGAA
---------+---------+---------+---------+---------+---------+
GluAspLeuAlaThrIleArgLysThrProGluMetAspValGlyGlnGluAlaLysGlu 1570                1590                1610
            .                   .                   .
CCTGCAGGAGACAGAAATCAATACTTAAACCCTGCAGAAACTTTCCTCAACAAGCTCCAC
---------+---------+---------+---------+---------+---------+
ProAlaGlyAspArgAsnGlnTyrLeuAsnProAlaGluThrPheLeuAsnLysLeuHis
```

FIG. 13C

```
        1630               1650              1670
AGGAAACACAGTAGGGAGGTGAAACATCAGGCCGTAAAGAAAGCTAAACGCCTAGCTGAA
---------+---------+---------+---------+---------+---------+
ArgLysHisSerArgGluValLysHisGlnAlaValLysLysAlaLysArgLeuAlaGlu 1690               1710              1730
ATCCAGGAGTCCATGAGAGCTGAGGGTGAGGCCGAACTAAATGAGATGAGCGGGGCATG
---------+---------+---------+---------+---------+---------+
IleGlnGluSerMetArgAlaGluGlyGluAlaGluLeuAsnGluMetSerGlyGlyMet 1750               1770              1790
AGGGCAATACCTAGCAACGCAGAACTTCCAGCACGAACGATGCTAGACAAGAACTCACA
---------+---------+---------+---------+---------+---------+
ArgAlaIleProSerAsnAlaGluLeuProSerThrAsnAspAlaArgGlnGluLeuThr 1810               1830              1850
CTCCCAACCACTAAACCTGTCCCTGCAAGGTGGGAAGATGCTTCATTCACAGATTCTAGT
---------+---------+---------+---------+---------+---------+
LeuProThrThrLysProValProAlaArgTrpGluAspAlaSerPheThrAspSerSer 1870               1890              1910
GTGAAAGAGGAGCAAGTGAAACTCCCTGGAAAAGAAGCCGTTGAGACAGCGACGCAACAA
---------+---------+---------+---------+---------+---------+
ValLysGluGluGlnValLysLeuProGlyLysGluAlaValGluThrAlaThrGlnGln 1930               1950              1970
GTCATAGAAGGACTCCCCTTGGAAACACTGGATTCCTCAACTAAATGCTGTTGGATTCAAG
---------+---------+---------+---------+---------+---------+
ValIleGluGlyLeuProTrpLysHisTrpIleProGlnLeuAsnAlaValGlyPheLys 1990               2010              2030
GCGCTGGAAATTCAGAGGGATAGGAGTGGGACAATGATCATGCCCATCACAGAAATGGTC
---------+---------+---------+---------+---------+---------+
AlaLeuGluIleGlnArgAspArgSerGlyThrMetIleMetProIleThrGluMetVal 2050               2070              2090
TCCGGGTTGGAAAAAGAGGACTTCCCGGAAGGAACTCCAAAAGAGTTGGCACGAGAATTG
---------+---------+---------+---------+---------+---------+
SerGlyLeuGluLysGluAspPheProGluGlyThrProLysGluLeuAlaArgGluLeu 2110               2130              2150
CTCGCTAAGAGCTCGCCCGGGGATCCAGCTTTCGTTCGTATCGGTTTCGACAACGTTCGT
---------+---------+---------+---------+---------+---------+
LeuAlaLysSerSerProGlyAspProAlaPheValArgIleGlyPheAspAsnValArg
```

FIG. 13D

```
                 2170                    2190
         CAAGTTCAATGCATCAGTTTCATTGCGCACACACCAGAATCCTACTGA
         ----------+----------+----------+----------+--------
         GlnValGlnCysIleSerPheIleAlaHisThrProGluSerTyrEnd
```

FIG. 13E

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 4371 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..4371

( x i ) SEQUENCE DESCRIPTION: SEQ ID NO:1:

```
ATG GCC AAA GTG CGC GAG GTT TAC CAA TCC TTT ACA GAC TCC ACC ACA        48
Met Ala Lys Val Arg Glu Val Tyr Gln Ser Phe Thr Asp Ser Thr Thr
 1               5                  10                  15

AAA ACT CTC ATC CAA GAT GAG GCT TAT AGA AAT ATT CGT CCC ATC ATG        96
Lys Thr Leu Ile Gln Asp Glu Ala Tyr Arg Asn Ile Arg Pro Ile Met
             20                  25                  30

GAA AAA CAT AAA CTA GCT AAC CCG TAC GCT CAA ACG GTT GAA GCG GCT       144
Glu Lys His Lys Leu Ala Asn Pro Tyr Ala Gln Thr Val Glu Ala Ala
         35                  40                  45

AAT GAT CTA GAG GGG TTC GGC ATA GCC ACC AAT CCC TAT AGC ATT GAG       192
Asn Asp Leu Glu Gly Phe Gly Ile Ala Thr Asn Pro Tyr Ser Ile Glu
     50                  55                  60

TTG CAT ACA CAT GCA GCT GCT AAG ACC ATA GAG AAT AAA CTT CTA GAG       240
Leu His Thr His Ala Ala Ala Lys Thr Ile Glu Asn Lys Leu Leu Glu
 65                  70                  75                  80

GTG CTT GGT TCC ATC CTA CCA CAA GAA CCT GTT ACA TTT ATG TTC CTT       288
Val Leu Gly Ser Ile Leu Pro Gln Glu Pro Val Thr Phe Met Phe Leu
                 85                  90                  95

AAA CCC AGG AAG CTA AAC TAC ATG AGA AGA AAC CCG CGG ATC AAG GAC       336
Lys Pro Arg Lys Leu Asn Tyr Met Arg Arg Asn Pro Arg Ile Lys Asp
            100                 105                 110

ATT TTC CAC AAT GTT GCC ATT GAA CCG AGA GAC GTA GCA AGG TAC CCC       384
Ile Phe His Asn Val Ala Ile Glu Pro Arg Asp Val Ala Arg Tyr Pro
        115                 120                 125
```

```
AAG GAA ACA ATA ATT GAC AAA CTC ACA GAG ATC ACA ACA GAC ACA GCA    432
Lys Glu Thr Ile Ile Asp Lys Leu Thr Glu Ile Thr Thr Asp Thr Ala
    130             135                 140

TAC ATT AGT GAC ACT CTG CAC TTC TTG GAT CCG AGC TAC ATA GTG GAG    480
Tyr Ile Ser Asp Thr Leu His Phe Leu Asp Pro Ser Tyr Ile Val Glu
145             150                 155                      160

ACA TTC CAA AAC TGC CCA AAA CTG CAA ACA TTG TAT GCG ACC TTA GTT    528
Thr Phe Gln Asn Cys Pro Lys Leu Gln Thr Leu Tyr Ala Thr Leu Val
                165                 170                 175

CTC CCC GTT GAG GCA GCC TTC AAA ATG GAA AGC ACT CAC CCG AAC ATA    576
Leu Pro Val Glu Ala Ala Phe Lys Met Glu Ser Thr His Pro Asn Ile
            180                 185                 190

TAC AGC CTC AAA TAC TTC GGA GAT GGT TTC CAG TAT ATA CCA GGC AAC    624
Tyr Ser Leu Lys Tyr Phe Gly Asp Gly Phe Gln Tyr Ile Pro Gly Asn
        195                 200                 205

CAT GGT GGT GGA GCG TAC CAT CAT GAA TTT GCT CAT TTA CAA TGG CTC    672
His Gly Gly Gly Ala Tyr His His Glu Phe Ala His Leu Gln Trp Leu
    210                 215                 220

AAA GTG GGA AAG ATC AAA TGG AGG GAC CCC AAG GAT AGC TTT CTC GGA    720
Lys Val Gly Lys Ile Lys Trp Arg Asp Pro Lys Asp Ser Phe Leu Gly
225             230                 235                      240

CAT CTC AAT TAC ACG ACT GAG CAG GTT GAG ATG CAC ACA GTG ACA GTG    768
His Leu Asn Tyr Thr Thr Glu Gln Val Glu Met His Thr Val Thr Val
                245                 250                 255

CAG TTG CAG GAA TCG TTC GCG GCA AAC CAC TTG TAC TGC ATC AGG AGA    816
Gln Leu Gln Glu Ser Phe Ala Ala Asn His Leu Tyr Cys Ile Arg Arg
            260                 265                 270

GGA GAT TTG CTC ACA CCG GAG GTG CGC ACT TTT GGC CAA CCT GAC AGG    864
Gly Asp Leu Leu Thr Pro Glu Val Arg Thr Phe Gly Gln Pro Asp Arg
        275                 280                 285

TAT GTG ATT CCA CCA CAG ATC TTC CTC CCG AAA GTC CAT AAC TGC AAG    912
Tyr Val Ile Pro Pro Gln Ile Phe Leu Pro Lys Val His Asn Cys Lys
    290                 295                 300

AAG CCG ATT CTT AAA AAA ACT ATG ATG CAG CTC TTC TTG TAT GTT AGG    960
Lys Pro Ile Leu Lys Lys Thr Met Met Gln Leu Phe Leu Tyr Val Arg
305             310                 315                      320

ACA GTT AAG GTC GCA AAA AAT TGT GAC ATT TTT GCC AAA GTC AGA CAA   1008
Thr Val Lys Val Ala Lys Asn Cys Asp Ile Phe Ala Lys Val Arg Gln
                325                 330                 335

TTA ATT AAA TCA TCT GAC CTG GAC AAA TAT TCT GCT GTG GAA CTG GTT   1056
Leu Ile Lys Ser Ser Asp Leu Asp Lys Tyr Ser Ala Val Glu Leu Val
            340                 345                 350

TAC TTA GTA AGC TAT ATG GAG TTC CTT GCC GAT CTA CAA GCT ACC ACC   1104
Tyr Leu Val Ser Tyr Met Glu Phe Leu Ala Asp Leu Gln Ala Thr Thr
        355                 360                 365

TGC TTC TCA GAC ACA CTT TCT GGT GGC TTA CTA ACA AAG ACC CTT GCA   1152
Cys Phe Ser Asp Thr Leu Ser Gly Gly Leu Leu Thr Lys Thr Leu Ala
    370                 375                 380

CCG GTG AGG GCT TGG ATA CAA GAG AAA AAG ATG CAG CTG TTT GGT CTT   1200
Pro Val Arg Ala Trp Ile Gln Glu Lys Lys Met Gln Leu Phe Gly Leu
385             390                 395                      400

GAG GAC TAC GCG AAG TTA GTC AAA GCA GTT GAT TTC CAC CCA GTG GAT   1248
Glu Asp Tyr Ala Lys Leu Val Lys Ala Val Asp Phe His Pro Val Asp
                405                 410                 415

TTT TCT TTT AAA GTT GAA ACT TGG GAC TTC AGA TTC CAC CCC TTG CAA   1296
Phe Ser Phe Lys Val Glu Thr Trp Asp Phe Arg Phe His Pro Leu Gln
            420                 425                 430

GCG TGG AAA GCC TTC CGA CCA AGG GAA GTG TCG GAT GTA GAG GAA ATG   1344
Ala Trp Lys Ala Phe Arg Pro Arg Glu Val Ser Asp Val Glu Glu Met
        435                 440                 445
```

| | | | | | | | | | | | | | | | | |
|---|---|---|---|---|---|---|---|---|---|---|---|---|---|---|---|---|
| GAA | AGT | TTG | TTC | TCA | GAT | GGG | GAC | CTG | CTT | GAC | TGC | TTC | ACA | AGA | ATG | 1392 |
| Glu | Ser | Leu | Phe | Ser | Asp | Gly | Asp | Leu | Leu | Asp | Cys | Phe | Thr | Arg | Met | |
| | 450 | | | | 455 | | | | | 460 | | | | | | |
| CCA | GCT | TAT | GCA | GTA | AAC | GCA | GAG | GAA | GAT | TTA | GCT | ACA | ATC | AGG | AAA | 1440 |
| Pro | Ala | Tyr | Ala | Val | Asn | Ala | Glu | Glu | Asp | Leu | Ala | Thr | Ile | Arg | Lys | |
| 465 | | | | | 470 | | | | | 475 | | | | | 480 | |
| ACG | CCC | GAG | ATG | GAT | GTC | GGT | CAA | GAA | GCC | AAA | GAA | CCT | GCA | GGA | GAC | 1488 |
| Thr | Pro | Glu | Met | Asp | Val | Gly | Gln | Glu | Ala | Lys | Glu | Pro | Ala | Gly | Asp | |
| | | | | 485 | | | | | 490 | | | | | 495 | | |
| AGA | AAT | CAA | TAC | TTA | AAC | CCT | GCA | GAA | ACT | TTC | CTC | AAC | AAG | CTC | CAC | 1536 |
| Arg | Asn | Gln | Tyr | Leu | Asn | Pro | Ala | Glu | Thr | Phe | Leu | Asn | Lys | Leu | His | |
| | | | 500 | | | | | 505 | | | | | 510 | | | |
| AGG | AAA | CAC | AGT | AGG | GAG | GTG | AAA | CAT | CAG | GCC | GTA | AAG | AAA | GCT | AAA | 1584 |
| Arg | Lys | His | Ser | Arg | Glu | Val | Lys | His | Gln | Ala | Val | Lys | Lys | Ala | Lys | |
| | | 515 | | | | | 520 | | | | | 525 | | | | |
| CGC | CTA | GCT | GAA | ATC | CAG | GAG | TCC | ATG | AGA | GCT | GAG | GGT | GAG | GCC | GAA | 1632 |
| Arg | Leu | Ala | Glu | Ile | Gln | Glu | Ser | Met | Arg | Ala | Glu | Gly | Glu | Ala | Glu | |
| | 530 | | | | | 535 | | | | | 540 | | | | | |
| CTA | AAT | GAG | ATG | AGC | GGG | GGC | ATG | AGG | GCA | ATA | CCT | AGC | AAC | GCA | GAA | 1680 |
| Leu | Asn | Glu | Met | Ser | Gly | Gly | Met | Arg | Ala | Ile | Pro | Ser | Asn | Ala | Glu | |
| 545 | | | | | 550 | | | | | 555 | | | | | 560 | |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn | Asp | Ala | Arg | Gln | Glu | Leu | Thr | Leu | Pro | Thr | Thr | |
| | | | | 565 | | | | | 570 | | | | | 575 | | |
| AAA | CCT | GTC | CCT | GCA | AGG | TGG | GAA | GAT | GCT | TCA | TTC | ACA | GAT | TCT | AGT | 1776 |
| Lys | Pro | Val | Pro | Ala | Arg | Trp | Glu | Asp | Ala | Ser | Phe | Thr | Asp | Ser | Ser | |
| | | | 580 | | | | | 585 | | | | | 590 | | | |
| GTG | AAA | GAG | GAG | CAA | GTG | AAA | CTC | CCT | GGA | AAA | GAA | GCC | GTT | GAG | ACA | 1824 |
| Val | Lys | Glu | Glu | Gln | Val | Lys | Leu | Pro | Gly | Lys | Glu | Ala | Val | Glu | Thr | |
| | | 595 | | | | | 600 | | | | | 605 | | | | |
| GCG | ACG | CAA | CAA | GTC | ATA | GAA | GGA | CTC | CCT | TGG | AAA | CAC | TGG | ATT | CCT | 1872 |
| Ala | Thr | Gln | Gln | Val | Ile | Glu | Gly | Leu | Pro | Trp | Lys | His | Trp | Ile | Pro | |
| | 610 | | | | | 615 | | | | | 620 | | | | | |
| CAA | CTA | AAT | GCT | GTT | GGA | TTC | AAG | GCG | CTG | GAA | ATT | CAG | AGG | GAT | AGG | 1920 |
| Gln | Leu | Asn | Ala | Val | Gly | Phe | Lys | Ala | Leu | Glu | Ile | Gln | Arg | Asp | Arg | |
| 625 | | | | | 630 | | | | | 635 | | | | | 640 | |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile | Met | Pro | Ile | Thr | Glu | Met | Val | Ser | Gly | Leu | Glu | |
| | | | | 645 | | | | | 650 | | | | | 655 | | |
| AAA | GAG | GAC | TTC | CCG | GAA | GGA | ACT | CCA | AAA | GAG | TTG | GCA | CGA | GAA | TTG | 2016 |
| Lys | Glu | Asp | Phe | Pro | Glu | Gly | Thr | Pro | Lys | Glu | Leu | Ala | Arg | Glu | Leu | |
| | | | 660 | | | | | 665 | | | | | 670 | | | |
| CTC | GCT | ATG | AAC | AGA | AGC | CCT | GCC | ACC | ATT | CCT | TTG | GAC | CTG | CTT | AGA | 2064 |
| Leu | Ala | Met | Asn | Arg | Ser | Pro | Ala | Thr | Ile | Pro | Leu | Asp | Leu | Leu | Arg | |
| | | 675 | | | | | 680 | | | | | 685 | | | | |
| GCC | AGA | GAC | TAC | GGC | AGT | GAT | GTG | AAG | AAC | AAG | AGA | ATT | GGT | GCC | ATC | 2112 |
| Ala | Arg | Asp | Tyr | Gly | Ser | Asp | Val | Lys | Asn | Lys | Arg | Ile | Gly | Ala | Ile | |
| | 690 | | | | | 695 | | | | | 700 | | | | | |
| ACA | AAG | ACA | CAA | GCA | ACA | AGT | TGG | GGC | GAG | TAC | CTA | ACA | GGA | AAG | ATA | 2160 |
| Thr | Lys | Thr | Gln | Ala | Thr | Ser | Trp | Gly | Glu | Tyr | Leu | Thr | Gly | Lys | Ile | |
| 705 | | | | | 710 | | | | | 715 | | | | | 720 | |
| GAA | AGT | CTG | ACT | GAG | AGG | AAA | GTT | GCG | ACT | TGT | GTC | ATT | CAT | GGA | GCT | 2208 |
| Glu | Ser | Leu | Thr | Glu | Arg | Lys | Val | Ala | Thr | Cys | Val | Ile | His | Gly | Ala | |
| | | | | 725 | | | | | 730 | | | | | 735 | | |
| GGA | GGC | TCT | GGG | AAA | AGT | CAT | GCC | ATC | CAG | AAG | GCA | TTG | AGA | GAA | ATT | 2256 |
| Gly | Gly | Ser | Gly | Lys | Ser | His | Ala | Ile | Gln | Lys | Ala | Leu | Arg | Glu | Ile | |
| | | | 740 | | | | | 745 | | | | | 750 | | | |
| GGC | AAG | GGG | TCA | GAC | ATC | ACT | GTA | GTC | CTG | CCG | ACC | AAT | GAA | CTG | CGA | 2304 |
| Gly | Lys | Gly | Ser | Asp | Ile | Thr | Val | Val | Leu | Pro | Thr | Asn | Glu | Leu | Arg | |
| | | 755 | | | | | 760 | | | | | 765 | | | | |

```
CTA GAT TGG AGC AAG AAA GTG CCT AAC ACT GAA CCA TAT ATG TTC AAG    2352
Leu Asp Trp Ser Lys Lys Val Pro Asn Thr Glu Pro Tyr Met Phe Lys
    770             775                 780

ACC TAT GAA AAG GCA TTA ATT GGG GGA ACA GGC AGT ATA GTC ATC TTT    2400
Thr Tyr Glu Lys Ala Leu Ile Gly Gly Thr Gly Ser Ile Val Ile Phe
785             790                 795                 800

GAC GAT TAC TCA AAA CTT CCT CCC GGT TAC ATA GAA GCC TTA ATC TGT    2448
Asp Asp Tyr Ser Lys Leu Pro Pro Gly Tyr Ile Glu Ala Leu Ile Cys
                805                 810                 815

TTC TAC TCT AAA ATC AAG CTA GTC ATT CTA ACA GGA GAT AGC AGA CAG    2496
Phe Tyr Ser Lys Ile Lys Leu Val Ile Leu Thr Gly Asp Ser Arg Gln
            820                 825                 830

AGC GTC TAC CAT GAA ACT GCT GAG GAC GCC TCC ATC AGG CAT TTG GGA    2544
Ser Val Tyr His Glu Thr Ala Glu Asp Ala Ser Ile Arg His Leu Gly
        835                 840                 845

CCA GCG ACA GAG TAC TTC TCA AAA TAC TGC CGA TAC TAT CTC AAT GCT    2592
Pro Ala Thr Glu Tyr Phe Ser Lys Tyr Cys Arg Tyr Tyr Leu Asn Ala
    850                 855                 860

ACA CAC CGC AAC AAG AAA GAC CTT GCG AAC ATG CTC GGT GTC TAC AGT    2640
Thr His Arg Asn Lys Lys Asp Leu Ala Asn Met Leu Gly Val Tyr Ser
865                 870                 875                 880

GAG AGA ACG GGG GTC ACC GAA ATC AGC ATG AGC GCC GAG TTC TTA GAA    2688
Glu Arg Thr Gly Val Thr Glu Ile Ser Met Ser Ala Glu Phe Leu Glu
                885                 890                 895

GGA ATC CCA ACT TTA GTA CCC TCG GAT GAG AAG AGA AAG CTG TAC ATG    2736
Gly Ile Pro Thr Leu Val Pro Ser Asp Glu Lys Arg Lys Leu Tyr Met
            900                 905                 910

GGC ACC GGG AGG AAC GAC ACG TTC ACA TAC GCT GGA TGC CAG GGG CTG    2784
Gly Thr Gly Arg Asn Asp Thr Phe Thr Tyr Ala Gly Cys Gln Gly Leu
        915                 920                 925

ACC AAG CCG AAA GTA CAA ATA GTG TTG GAC CAC AAC ACC CAA GTG TGT    2832
Thr Lys Pro Lys Val Gln Ile Val Leu Asp His Asn Thr Gln Val Cys
    930                 935                 940

AGC GCG AAT GTG ATG TAC ACG GCA CTT TCT AGA GCC ACC GAC AGG ATT    2880
Ser Ala Asn Val Met Tyr Thr Ala Leu Ser Arg Ala Thr Asp Arg Ile
945                 950                 955                 960

CAC TTC GTG AAC ACA AGT GCA AAC TCT TCG GCC TTC TGG GAA AAG TTA    2928
His Phe Val Asn Thr Ser Ala Asn Ser Ser Ala Phe Trp Glu Lys Leu
                965                 970                 975

GAC AGC ACC CCT TAT CTC AAG ACT TTC CTA TCA GTG GTG AGA GAA CAA    2976
Asp Ser Thr Pro Tyr Leu Lys Thr Phe Leu Ser Val Val Arg Glu Gln
            980                 985                 990

GCA CTC AGG GAG TAC GAG CCG GCA GAG GCA GAG CCA ATT CGA GAG CCT    3024
Ala Leu Arg Glu Tyr Glu Pro Ala Glu Ala Glu Pro Ile Arg Glu Pro
        995                 1000                1005

GAG CCC CAG ACA CAC ATG TGT GTC GAG AAT GAG GAG TCC GTG CTA GAA    3072
Glu Pro Gln Thr His Met Cys Val Glu Asn Glu Glu Ser Val Leu Glu
    1010                1015                1020

GAG TAC AAA GAG GAA CTC TTG GAA AAG TTT GAC AGA GAG ATC CAC TCG    3120
Glu Tyr Lys Glu Glu Leu Leu Glu Lys Phe Asp Arg Glu Ile His Ser
1025                1030                1035                1040

GAA TCC CAT GGT CAT TCA AAC TGT GTC CAA ACA GAA GAC ACA ACC ATT    3168
Glu Ser His Gly His Ser Asn Cys Val Gln Thr Glu Asp Thr Thr Ile
                1045                1050                1055

CAG TTG TTT TCG CAT CAA CAA GCA AAA GAT GAG ACC CTC CTC TGG GCG    3216
Gln Leu Phe Ser His Gln Gln Ala Lys Asp Glu Thr Leu Leu Trp Ala
            1060                1065                1070

ACT ATA GAT GCG CGG CTC AAG ATT AGC AAT CAA GAG ACA AAC TTC CGA    3264
Thr Ile Asp Ala Arg Leu Lys Ile Ser Asn Gln Glu Thr Asn Phe Arg
        1075                1080                1085
```

| | | | | | | | | | | | | | | | | |
|---|---|---|---|---|---|---|---|---|---|---|---|---|---|---|---|---|
| GAA | TTC | TTG | AGC | AAG | AAG | GAC | ATT | GGG | GAC | GTT | CTG | TTT | TTG | AAC | TAC | 3312 |
| Glu 1090 | Phe | Leu | Ser | Lys | Lys 1095 | Asp | Ile | Gly | Asp | Val 1100 | Leu | Phe | Leu | Asn | Tyr | |
| CAA | AAA | GCT | ATG | GGT | CTG | CCC | AAA | GAG | CGT | ATT | CCC | TTT | TCA | CAA | GAG | 3360 |
| Gln 1105 | Lys | Ala | Met | Gly | Leu 1110 | Pro | Lys | Glu | Arg | Ile 1115 | Pro | Phe | Ser | Gln | Glu 1120 | |
| GTC | TGG | GAA | GCT | TGT | GCC | CAT | GAA | GTA | CAA | AGC | AAG | TAC | CTC | AGT | AAG | 3408 |
| Val | Trp | Glu | Ala | Cys 1125 | Ala | His | Glu | Val | Gln 1130 | Ser | Lys | Tyr | Leu | Ser 1135 | Lys | |
| TCA | AAG | TGC | AAC | TTG | ATC | AAC | GGG | ACT | GTG | AGA | CAG | AGC | CCA | GAC | TTT | 3456 |
| Ser | Lys | Cys | Asn 1140 | Leu | Ile | Asn | Gly | Thr 1145 | Val | Arg | Gln | Ser | Pro 1150 | Asp | Phe | |
| GAC | GAA | AAC | AAA | ATT | ATG | GTA | TTC | CTC | AAG | TCG | CAG | TGG | GTC | ACA | AAG | 3504 |
| Asp | Glu | Asn | Lys 1155 | Ile | Met | Val | Phe | Leu 1160 | Lys | Ser | Gln | Trp | Val 1165 | Thr | Lys | |
| GTG | GAA | AAG | CTA | GGT | CTA | CCC | AAG | ATT | AAG | CCA | GGT | CAA | ACC | ATA | GCA | 3552 |
| Val | Glu | Lys 1170 | Leu | Gly | Leu | Pro | Lys 1175 | Ile | Lys | Pro | Gly | Gln 1180 | Thr | Ile | Ala | |
| GCT | TTT | TAT | CAG | CAG | ACT | GTG | ATG | CTT | TTT | GGA | ACT | ATG | GCT | AGG | TAC | 3600 |
| Ala 1185 | Phe | Tyr | Gln | Gln | Thr 1190 | Val | Met | Leu | Phe | Gly 1195 | Thr | Met | Ala | Arg | Tyr 1200 | |
| ATG | CGA | TGG | TTC | AGA | CAG | GCT | TTC | CAG | CCA | AAA | GAA | GTC | TTC | ATA | AAC | 3648 |
| Met | Arg | Trp | Phe | Arg 1205 | Gln | Ala | Phe | Gln | Pro 1210 | Lys | Glu | Val | Phe | Ile 1215 | Asn | |
| TGT | GAG | ACC | ACG | CCA | GAA | GAC | ATG | TCT | GCA | TGG | GCC | TTG | AAC | AAC | TGG | 3696 |
| Cys | Glu | Thr | Thr | Pro 1220 | Glu | Asp | Met | Ser | Ala 1225 | Trp | Ala | Leu | Asn | Asn 1230 | Trp | |
| AAT | TTC | GGC | AGA | CCT | AGC | TTG | GCC | AAT | GAC | TAC | ACA | GCT | TTC | GAC | CAG | 3744 |
| Asn | Phe | Gly | Arg 1235 | Pro | Ser | Leu | Ala | Asn 1240 | Asp | Tyr | Thr | Ala | Phe 1245 | Asp | Gln | |
| TCT | CAG | GAT | GGA | GCT | ATG | CTG | CAA | TTT | GAG | GTG | CTC | AAA | GCC | AAG | CAC | 3792 |
| Ser | Gln | Asp | Gly 1250 | Ala | Met | Leu | Gln | Phe 1255 | Glu | Val | Leu | Lys | Ala 1260 | Lys | His | |
| CAT | TGC | ATA | CCA | GAG | GAA | ATC | ATC | CAA | GCA | TAC | ATA | GAC | ATT | AAG | ACC | 3840 |
| His 1265 | Cys | Ile | Pro | Glu | Glu 1270 | Ile | Ile | Gln | Ala | Tyr 1275 | Ile | Asp | Ile | Lys | Thr 1280 | |
| AAT | GCA | CAG | ATT | TTC | CTA | GGC | ACA | TTG | TCA | ATC | ATG | CGC | CTG | ACT | GGT | 3888 |
| Asn | Ala | Gln | Ile | Phe 1285 | Leu | Gly | Thr | Leu | Ser 1290 | Ile | Met | Arg | Leu | Thr 1295 | Gly | |
| GAG | GGT | CCC | ACT | TTT | GAT | GCA | AAC | ACT | GAG | TGC | AAC | ATA | GCT | TAC | ACC | 3936 |
| Glu | Gly | Pro | Thr | Phe 1300 | Asp | Ala | Asn | Thr | Glu 1305 | Cys | Asn | Ile | Ala | Tyr 1310 | Thr | |
| CAT | ACA | AAG | TTT | GAC | ATC | CCA | GCA | GGA | ACT | GCT | CAA | GTT | TAT | GCA | GGA | 3984 |
| His | Thr | Lys | Phe | Asp 1315 | Ile | Pro | Ala | Gly | Thr 1320 | Ala | Gln | Val | Tyr | Ala 1325 | Gly | |
| GAC | GAC | TCA | GCA | CTG | GAT | TGC | GTT | CCA | GAA | GTG | AAG | CAT | AGC | TTC | CAC | 4032 |
| Asp | Asp | Ser | Ala 1330 | Leu | Asp | Cys | Val | Pro 1335 | Glu | Val | Lys | His | Ser 1340 | Phe | His | |
| AGG | CTT | GAA | GAC | AAA | CTA | CTC | CTT | AAG | TCA | AAG | CCC | GTA | ATC | ACG | CAG | 4080 |
| Arg | Leu | Glu | Asp | Lys 1345 | Leu | Leu | Leu | Lys | Ser 1350 | Lys | Pro | Val | Ile | Thr 1355 | Gln 1360 | |
| CAA | AAG | AAA | GGC | AGT | TGG | CCT | GAG | TTT | TGT | GGT | TGG | CTG | ATT | ACA | CCA | 4128 |
| Gln | Lys | Lys | Gly | Ser 1365 | Trp | Pro | Glu | Phe | Cys 1370 | Gly | Trp | Leu | Ile | Thr 1375 | Pro | |
| AAA | GGG | GTA | ATG | AAA | GAC | CCA | ATT | AAG | CTC | CAT | GTT | AGC | TTA | AAA | TTG | 4176 |
| Lys | Gly | Val | Met | Lys 1380 | Asp | Pro | Ile | Lys | Leu 1385 | His | Val | Ser | Leu | Lys 1390 | Leu | |
| GCC | GAA | GCT | AAG | GGC | GAA | CTC | AAG | AAA | TGT | CAA | GAC | TCC | TAT | GAA | ATT | 4224 |
| Ala | Glu | Ala | Lys | Gly 1395 | Glu | Leu | Lys | Lys | Cys 1400 | Gln | Asp | Ser | Tyr | Glu 1405 | Ile | |

```
GAT CTG AGT TAT GCC TAC GAC CAC AAG GAC TCT CTG CAT GAC TTG TTC      4272
Asp Leu Ser Tyr Ala Tyr Asp His Lys Asp Ser Leu His Asp Leu Phe
    1410                    1415                1420

GAT GAG AAA CAG TGT CAG GCA CAT ACA CTC ACT TGC AGA ACA CTG ATC      4320
Asp Glu Lys Gln Cys Gln Ala His Thr Leu Thr Cys Arg Thr Leu Ile
1425                1430                1435                    1440

AAG TCA GGG AGA GGC ACT GTC TCA CTT CCC CGC CTC AGA AAC TTT CTT      4368
Lys Ser Gly Arg Gly Thr Val Ser Leu Pro Arg Leu Arg Asn Phe Leu
                1445                1450                1455

TAA                                                                   4371
```

( 2 ) INFORMATION FOR SEQ ID NO:2:

( i ) SEQUENCE CHARACTERISTICS:
        ( A ) LENGTH: 1456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Lys Val Arg Glu Val Tyr Gln Ser Phe Thr Asp Ser Thr Thr
 1               5                  10                  15

Lys Thr Leu Ile Gln Asp Glu Ala Tyr Arg Asn Ile Arg Pro Ile Met
            20                  25                  30

Glu Lys His Lys Leu Ala Asn Pro Tyr Ala Gln Thr Val Glu Ala Ala
        35                  40                  45

Asn Asp Leu Glu Gly Phe Gly Ile Ala Thr Asn Pro Tyr Ser Ile Glu
    50                  55                  60

Leu His Thr His Ala Ala Ala Lys Thr Ile Glu Asn Lys Leu Leu Glu
65                  70                  75                  80

Val Leu Gly Ser Ile Leu Pro Gln Glu Pro Val Thr Phe Met Phe Leu
                85                  90                  95

Lys Pro Arg Lys Leu Asn Tyr Met Arg Arg Asn Pro Arg Ile Lys Asp
                100                 105                 110

Ile Phe His Asn Val Ala Ile Glu Pro Arg Asp Val Ala Arg Tyr Pro
            115                 120                 125

Lys Glu Thr Ile Ile Asp Lys Leu Thr Glu Ile Thr Thr Asp Thr Ala
    130                 135                 140

Tyr Ile Ser Asp Thr Leu His Phe Leu Asp Pro Ser Tyr Ile Val Glu
145                 150                 155                 160

Thr Phe Gln Asn Cys Pro Lys Leu Gln Thr Leu Tyr Ala Thr Leu Val
                165                 170                 175

Leu Pro Val Glu Ala Ala Phe Lys Met Glu Ser Thr His Pro Asn Ile
            180                 185                 190

Tyr Ser Leu Lys Tyr Phe Gly Asp Gly Phe Gln Tyr Ile Pro Gly Asn
        195                 200                 205

His Gly Gly Gly Ala Tyr His His Glu Phe Ala His Leu Gln Trp Leu
    210                 215                 220

Lys Val Gly Lys Ile Lys Trp Arg Asp Pro Lys Asp Ser Phe Leu Gly
225                 230                 235                 240

His Leu Asn Tyr Thr Thr Glu Gln Val Glu Met His Thr Val Thr Val
                245                 250                 255

Gln Leu Gln Glu Ser Phe Ala Ala Asn His Leu Tyr Cys Ile Arg Arg
            260                 265                 270

Gly Asp Leu Leu Thr Pro Glu Val Arg Thr Phe Gly Gln Pro Asp Arg
        275                 280                 285
```

-continued

```
Tyr Val Ile Pro Pro Gln Ile Phe Leu Pro Lys Val His Asn Cys Lys
    290             295             300
Lys Pro Ile Leu Lys Lys Thr Met Met Gln Leu Phe Leu Tyr Val Arg
305             310             315             320
Thr Val Lys Val Ala Lys Asn Cys Asp Ile Phe Ala Lys Val Arg Gln
            325             330             335
Leu Ile Lys Ser Ser Asp Leu Asp Lys Tyr Ser Ala Val Glu Leu Val
        340             345             350
Tyr Leu Val Ser Tyr Met Glu Phe Leu Ala Asp Leu Gln Ala Thr Thr
        355             360             365
Cys Phe Ser Asp Thr Leu Ser Gly Gly Leu Leu Thr Lys Thr Leu Ala
370             375             380
Pro Val Arg Ala Trp Ile Gln Glu Lys Lys Met Gln Leu Phe Gly Leu
385             390             395                 400
Glu Asp Tyr Ala Lys Leu Val Lys Ala Val Asp Phe His Pro Val Asp
            405             410             415
Phe Ser Phe Lys Val Glu Thr Trp Asp Phe Arg Phe His Pro Leu Gln
            420             425             430
Ala Trp Lys Ala Phe Arg Pro Arg Glu Val Ser Asp Val Glu Glu Met
        435             440             445
Glu Ser Leu Phe Ser Asp Gly Asp Leu Leu Asp Cys Phe Thr Arg Met
    450             455             460
Pro Ala Tyr Ala Val Asn Ala Glu Glu Asp Leu Ala Thr Ile Arg Lys
465             470             475                 480
Thr Pro Glu Met Asp Val Gly Gln Glu Ala Lys Glu Pro Ala Gly Asp
            485             490             495
Arg Asn Gln Tyr Leu Asn Pro Ala Glu Thr Phe Leu Asn Lys Leu His
        500             505             510
Arg Lys His Ser Arg Glu Val Lys His Gln Ala Val Lys Lys Ala Lys
        515             520             525
Arg Leu Ala Glu Ile Gln Glu Ser Met Arg Ala Glu Gly Glu Ala Glu
530             535             540
Leu Asn Glu Met Ser Gly Gly Met Arg Ala Ile Pro Ser Asn Ala Glu
545             550             555                 560
Leu Pro Ser Thr Asn Asp Ala Arg Gln Glu Leu Thr Leu Pro Thr Thr
            565             570             575
Lys Pro Val Pro Ala Arg Trp Glu Asp Ala Ser Phe Thr Asp Ser Ser
            580             585             590
Val Lys Glu Glu Gln Val Lys Leu Pro Gly Lys Glu Ala Val Glu Thr
        595             600             605
Ala Thr Gln Gln Val Ile Glu Gly Leu Pro Trp Lys His Trp Ile Pro
610             615             620
Gln Leu Asn Ala Val Gly Phe Lys Ala Leu Glu Ile Gln Arg Asp Arg
625             630             635                 640
Ser Gly Thr Met Ile Met Pro Ile Thr Glu Met Val Ser Gly Leu Glu
            645             650             655
Lys Glu Asp Phe Pro Glu Gly Thr Pro Lys Glu Leu Ala Arg Glu Leu
            660             665             670
Leu Ala Met Asn Arg Ser Pro Ala Thr Ile Pro Leu Asp Leu Leu Arg
        675             680             685
Ala Arg Asp Tyr Gly Ser Asp Val Lys Asn Lys Arg Ile Gly Ala Ile
690             695             700
Thr Lys Thr Gln Ala Thr Ser Trp Gly Glu Tyr Leu Thr Gly Lys Ile
```

|     |     |     |     |     |     |     |     |     |     |     |     |     |     |     |
|-----|-----|-----|-----|-----|-----|-----|-----|-----|-----|-----|-----|-----|-----|-----|
| 705 |     |     |     |     | 710 |     |     |     |     | 715 |     |     |     | 720 |
| Glu | Ser | Leu | Thr | Glu | Arg | Lys | Val | Ala | Thr | Cys | Val | Ile | His | Gly | Ala |
|     |     |     |     | 725 |     |     |     |     | 730 |     |     |     | 735 |     |
| Gly | Gly | Ser | Gly | Lys | Ser | His | Ala | Ile | Gln | Lys | Ala | Leu | Arg | Glu | Ile |
|     |     |     | 740 |     |     |     |     | 745 |     |     |     |     | 750 |     |
| Gly | Lys | Gly | Ser | Asp | Ile | Thr | Val | Val | Leu | Pro | Thr | Asn | Glu | Leu | Arg |
|     |     | 755 |     |     |     | 760 |     |     |     |     | 765 |     |     |     |
| Leu | Asp | Trp | Ser | Lys | Lys | Val | Pro | Asn | Thr | Glu | Pro | Tyr | Met | Phe | Lys |
|     | 770 |     |     |     | 775 |     |     |     |     | 780 |     |     |     |     |
| Thr | Tyr | Glu | Lys | Ala | Leu | Ile | Gly | Gly | Thr | Gly | Ser | Ile | Val | Ile | Phe |
| 785 |     |     |     |     | 790 |     |     |     |     | 795 |     |     |     |     | 800 |
| Asp | Asp | Tyr | Ser | Lys | Leu | Pro | Pro | Gly | Tyr | Ile | Glu | Ala | Leu | Ile | Cys |
|     |     |     | 805 |     |     |     |     | 810 |     |     |     |     | 815 |     |
| Phe | Tyr | Ser | Lys | Ile | Lys | Leu | Val | Ile | Leu | Thr | Gly | Asp | Ser | Arg | Gln |
|     |     |     | 820 |     |     |     |     | 825 |     |     |     | 830 |     |     |
| Ser | Val | Tyr | His | Glu | Thr | Ala | Glu | Asp | Ala | Ser | Ile | Arg | His | Leu | Gly |
|     |     | 835 |     |     |     |     | 840 |     |     |     |     | 845 |     |     |
| Pro | Ala | Thr | Glu | Tyr | Phe | Ser | Lys | Tyr | Cys | Arg | Tyr | Tyr | Leu | Asn | Ala |
|     | 850 |     |     |     |     | 855 |     |     |     |     | 860 |     |     |     |
| Thr | His | Arg | Asn | Lys | Lys | Asp | Leu | Ala | Asn | Met | Leu | Gly | Val | Tyr | Ser |
| 865 |     |     |     |     | 870 |     |     |     |     | 875 |     |     |     |     | 880 |
| Glu | Arg | Thr | Gly | Val | Thr | Glu | Ile | Ser | Met | Ser | Ala | Glu | Phe | Leu | Glu |
|     |     |     |     | 885 |     |     |     |     | 890 |     |     |     |     | 895 |     |
| Gly | Ile | Pro | Thr | Leu | Val | Pro | Ser | Asp | Glu | Lys | Arg | Lys | Leu | Tyr | Met |
|     |     |     | 900 |     |     |     |     | 905 |     |     |     |     | 910 |     |
| Gly | Thr | Gly | Arg | Asn | Asp | Thr | Phe | Thr | Tyr | Ala | Gly | Cys | Gln | Gly | Leu |
|     |     | 915 |     |     |     |     | 920 |     |     |     |     | 925 |     |     |
| Thr | Lys | Pro | Lys | Val | Gln | Ile | Val | Leu | Asp | His | Asn | Thr | Gln | Val | Cys |
|     | 930 |     |     |     |     | 935 |     |     |     |     | 940 |     |     |     |
| Ser | Ala | Asn | Val | Met | Tyr | Thr | Ala | Leu | Ser | Arg | Ala | Thr | Asp | Arg | Ile |
| 945 |     |     |     |     | 950 |     |     |     |     | 955 |     |     |     |     | 960 |
| His | Phe | Val | Asn | Thr | Ser | Ala | Asn | Ser | Ser | Ala | Phe | Trp | Glu | Lys | Leu |
|     |     |     |     | 965 |     |     |     |     | 970 |     |     |     |     | 975 |     |
| Asp | Ser | Thr | Pro | Tyr | Leu | Lys | Thr | Phe | Leu | Ser | Val | Val | Arg | Glu | Gln |
|     |     |     | 980 |     |     |     |     | 985 |     |     |     |     | 990 |     |
| Ala | Leu | Arg | Glu | Tyr | Glu | Pro | Ala | Glu | Ala | Glu | Pro | Ile | Arg | Glu | Pro |
|     |     | 995 |     |     |     | 1000|     |     |     |     | 1005|     |     |     |
| Glu | Pro | Gln | Thr | His | Met | Cys | Val | Glu | Asn | Glu | Glu | Ser | Val | Leu | Glu |
|     |     | 1010|     |     |     | 1015|     |     |     |     | 1020|     |     |     |
| Glu | Tyr | Lys | Glu | Glu | Leu | Leu | Glu | Lys | Phe | Asp | Arg | Glu | Ile | His | Ser |
| 1025|     |     |     |     | 1030|     |     |     |     | 1035|     |     |     |     | 1040|
| Glu | Ser | His | Gly | His | Ser | Asn | Cys | Val | Gln | Thr | Glu | Asp | Thr | Thr | Ile |
|     |     |     |     | 1045|     |     |     |     | 1050|     |     |     |     | 1055|     |
| Gln | Leu | Phe | Ser | His | Gln | Gln | Ala | Lys | Asp | Glu | Thr | Leu | Leu | Trp | Ala |
|     |     |     |     | 1060|     |     |     |     | 1065|     |     |     |     | 1070|     |
| Thr | Ile | Asp | Ala | Arg | Leu | Lys | Ile | Ser | Asn | Gln | Glu | Thr | Asn | Phe | Arg |
|     |     |     | 1075|     |     |     |     | 1080|     |     |     |     | 1085|     |     |
| Glu | Phe | Leu | Ser | Lys | Lys | Asp | Ile | Gly | Asp | Val | Leu | Phe | Leu | Asn | Tyr |
|     |     | 1090|     |     |     |     | 1095|     |     |     |     | 1100|     |     |
| Gln | Lys | Ala | Met | Gly | Leu | Pro | Lys | Glu | Arg | Ile | Pro | Phe | Ser | Gln | Glu |
| 1105|     |     |     |     | 1110|     |     |     |     | 1115|     |     |     |     | 1120|
| Val | Trp | Glu | Ala | Cys | Ala | His | Glu | Val | Gln | Ser | Lys | Tyr | Leu | Ser | Lys |
|     |     |     |     | 1125|     |     |     |     | 1130|     |     |     |     | 1135|     |

Ser Lys Cys Asn Leu Ile Asn Gly Thr Val Arg Gln Ser Pro Asp Phe
                1140                1145                1150

Asp Glu Asn Lys Ile Met Val Phe Leu Lys Ser Gln Trp Val Thr Lys
            1155                1160                1165

Val Glu Lys Leu Gly Leu Pro Lys Ile Lys Pro Gly Gln Thr Ile Ala
    1170                1175                1180

Ala Phe Tyr Gln Gln Thr Val Met Leu Phe Gly Thr Met Ala Arg Tyr
1185                1190                1195                1200

Met Arg Trp Phe Arg Gln Ala Phe Gln Pro Lys Glu Val Phe Ile Asn
                1205                1210                1215

Cys Glu Thr Thr Pro Glu Asp Met Ser Ala Trp Ala Leu Asn Asn Trp
                1220                1225                1230

Asn Phe Gly Arg Pro Ser Leu Ala Asn Asp Tyr Thr Ala Phe Asp Gln
            1235                1240                1245

Ser Gln Asp Gly Ala Met Leu Gln Phe Glu Val Leu Lys Ala Lys His
    1250                1255                1260

His Cys Ile Pro Glu Glu Ile Ile Gln Ala Tyr Ile Asp Ile Lys Thr
1265                1270                1275                1280

Asn Ala Gln Ile Phe Leu Gly Thr Leu Ser Ile Met Arg Leu Thr Gly
                1285                1290                1295

Glu Gly Pro Thr Phe Asp Ala Asn Thr Glu Cys Asn Ile Ala Tyr Thr
                1300                1305                1310

His Thr Lys Phe Asp Ile Pro Ala Gly Thr Ala Gln Val Tyr Ala Gly
            1315                1320                1325

Asp Asp Ser Ala Leu Asp Cys Val Pro Glu Val Lys His Ser Phe His
    1330                1335                1340

Arg Leu Glu Asp Lys Leu Leu Leu Lys Ser Lys Pro Val Ile Thr Gln
1345                1350                1355                1360

Gln Lys Lys Gly Ser Trp Pro Glu Phe Cys Gly Trp Leu Ile Thr Pro
                1365                1370                1375

Lys Gly Val Met Lys Asp Pro Ile Lys Leu His Val Ser Leu Lys Leu
            1380                1385                1390

Ala Glu Ala Lys Gly Glu Leu Lys Lys Cys Gln Asp Ser Tyr Glu Ile
    1395                1400                1405

Asp Leu Ser Tyr Ala Tyr Asp His Lys Asp Ser Leu His Asp Leu Phe
    1410                1415                1420

Asp Glu Lys Gln Cys Gln Ala His Thr Leu Thr Cys Arg Thr Leu Ile
1425                1430                1435                1440

Lys Ser Gly Arg Gly Thr Val Ser Leu Pro Arg Leu Arg Asn Phe Leu
                1445                1450                1455

( 2 ) INFORMATION FOR SEQ ID NO:3:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

GAAAACTAAA CCATACACCA CCAACACAAC CAAACCCACC ACGCCCAATT GTTACACACC    60

CGCTTGAAAA AGCAAGTCTG ACAA    84

( 2 ) INFORMATION FOR SEQ ID NO:4:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ii) MOLECULE TYPE: DNA (synthetic)

(xi) SEQUENCE DESCRIPTION: SEQ ID NO:4:

TATGGTTTAG TTTTCGAGCT CTATAGTGAG TCGTAT    36

(2) INFORMATION FOR SEQ ID NO:5:

(i) SEQUENCE CHARACTERISTICS:
  (A) LENGTH: 33 base pairs
  (B) TYPE: nucleic acid
  (C) STRANDEDNESS: single
  (D) TOPOLOGY: linear (ii) MOLECULE TYPE: DNA (synthetic)

(xi) SEQUENCE DESCRIPTION: SEQ ID NO:5:

GGTAACTTAA CGGGAGCTCT TAAAGAAAGT TTC    33

(2) INFORMATION FOR SEQ ID NO:6:

(i) SEQUENCE CHARACTERISTICS:
  (A) LENGTH: 2022 base pairs
  (B) TYPE: nucleic acid
  (C) STRANDEDNESS: double
  (D) TOPOLOGY: linear (ii) MOLECULE TYPE: cDNA (ix) FEATURE:
  (A) NAME/KEY: CDS
  (B) LOCATION: 1..2022

(xi) SEQUENCE DESCRIPTION: SEQ ID NO:6:

| ATG | GCC | AAA | GTG | CGC | GAG | GTT | TAC | CAA | TCC | TTT | ACA | GAC | TCC | ACC | ACA | 48 |
| Met | Ala | Lys | Val | Arg | Glu | Val | Tyr | Gln | Ser | Phe | Thr | Asp | Ser | Thr | Thr | |
| 1 | | | | 5 | | | | | 10 | | | | | 15 | | |

| AAA | ACT | CTC | ATC | CAA | GAT | GAG | GCT | TAT | AGA | AAT | ATT | CGT | CCC | ATC | ATG | 96 |
| Lys | Thr | Leu | Ile | Gln | Asp | Glu | Ala | Tyr | Arg | Asn | Ile | Arg | Pro | Ile | Met | |
| | | | 20 | | | | | 25 | | | | | 30 | | | |

| GAA | AAA | CAT | AAA | CTA | GCT | AAC | CCG | TAC | GCT | CAA | ACG | GTT | GAA | GCG | GCT | 144 |
| Glu | Lys | His | Lys | Leu | Ala | Asn | Pro | Tyr | Ala | Gln | Thr | Val | Glu | Ala | Ala | |
| | | 35 | | | | | 40 | | | | | 45 | | | | |

| AAT | GAT | CTA | GAG | GGG | TTC | GGC | ATA | GCC | ACC | AAT | CCC | TAT | AGC | ATT | GAG | 192 |
| Asn | Asp | Leu | Glu | Gly | Phe | Gly | Ile | Ala | Thr | Asn | Pro | Tyr | Ser | Ile | Glu | |
| | | 50 | | | | | 55 | | | | | 60 | | | | |

| TTG | CAT | ACA | CAT | GCA | GCT | GCT | AAG | ACC | ATA | GAG | AAT | AAA | CTT | CTA | GAG | 240 |
| Leu | His | Thr | His | Ala | Ala | Ala | Lys | Thr | Ile | Glu | Asn | Lys | Leu | Leu | Glu | |
| 65 | | | | | 70 | | | | | 75 | | | | | 80 | |

| GTG | CTT | GGT | TCC | ATC | CTA | CCA | CAA | GAA | CCT | GTT | ACA | TTT | ATG | TTC | CTT | 288 |
| Val | Leu | Gly | Ser | Ile | Leu | Pro | Gln | Glu | Pro | Val | Thr | Phe | Met | Phe | Leu | |
| | | | | 85 | | | | | 90 | | | | | 95 | | |

| AAA | CCC | AGG | AAG | CTA | AAC | TAC | ATG | AGA | AGA | AAC | CCG | CGG | ATC | AAG | GAC | 336 |
| Lys | Pro | Arg | Lys | Leu | Asn | Tyr | Met | Arg | Arg | Asn | Pro | Arg | Ile | Lys | Asp | |
| | | | 100 | | | | | 105 | | | | | 110 | | | |

| ATT | TTC | CAC | AAT | GTT | GCC | ATT | GAA | CCG | AGA | GAC | GTA | GCA | AGG | TAC | CCC | 384 |
| Ile | Phe | His | Asn | Val | Ala | Ile | Glu | Pro | Arg | Asp | Val | Ala | Arg | Tyr | Pro | |
| | | 115 | | | | | 120 | | | | | 125 | | | | |

| AAG | GAA | ACA | ATA | ATT | GAC | AAA | CTC | ACA | GAG | ATC | ACA | ACA | GAC | ACA | GCA | 432 |
| Lys | Glu | Thr | Ile | Ile | Asp | Lys | Leu | Thr | Glu | Ile | Thr | Thr | Asp | Thr | Ala | |
| | | 130 | | | | | 135 | | | | | 140 | | | | |

| | | | | | | | | | | | | | | | |
|---|---|---|---|---|---|---|---|---|---|---|---|---|---|---|---|
| TAC | ATT | AGT | GAC | ACT | CTG | CAC | TTC | TTG | GAT | CCG | AGC | TAC | ATA | GTG | GAG | 480 |
| Tyr | Ile | Ser | Asp | Thr | Leu | His | Phe | Leu | Asp | Pro | Ser | Tyr | Ile | Val | Glu | |
| 145 | | | | 150 | | | | | 155 | | | | | 160 | | |
| ACA | TTC | CAA | AAC | TGC | CCA | AAA | CTG | CAA | ACA | TTG | TAT | GCG | ACC | TTA | GTT | 528 |
| Thr | Phe | Gln | Asn | Cys | Pro | Lys | Leu | Gln | Thr | Leu | Tyr | Ala | Thr | Leu | Val | |
| | | | | 165 | | | | | 170 | | | | | 175 | | |
| CTC | CCC | GTT | GAG | GCA | GCC | TTC | AAA | ATG | GAA | AGC | ACT | CAC | CCG | AAC | ATA | 576 |
| Leu | Pro | Val | Glu | Ala | Ala | Phe | Lys | Met | Glu | Ser | Thr | His | Pro | Asn | Ile | |
| | | | 180 | | | | | 185 | | | | | 190 | | | |
| TAC | AGC | CTC | AAA | TAC | TTC | GGA | GAT | GGT | TTC | CAG | TAT | ATA | CCA | GGC | AAC | 624 |
| Tyr | Ser | Leu | Lys | Tyr | Phe | Gly | Asp | Gly | Phe | Gln | Tyr | Ile | Pro | Gly | Asn | |
| | | 195 | | | | | 200 | | | | | 205 | | | | |
| CAT | GGT | GGT | GGA | GCG | TAC | CAT | CAT | GAA | TTT | GCT | CAT | TTA | CAA | TGG | CTC | 672 |
| His | Gly | Gly | Gly | Ala | Tyr | His | His | Glu | Phe | Ala | His | Leu | Gln | Trp | Leu | |
| | 210 | | | | | 215 | | | | | 220 | | | | | |
| AAA | GTG | GGA | AAG | ATC | AAA | TGG | AGG | GAC | CCC | AAG | GAT | AGC | TTT | CTC | GGA | 720 |
| Lys | Val | Gly | Lys | Ile | Lys | Trp | Arg | Asp | Pro | Lys | Asp | Ser | Phe | Leu | Gly | |
| 225 | | | | | 230 | | | | | 235 | | | | | 240 | |
| CAT | CTC | AAT | TAC | ACG | ACT | GAG | CAG | GTT | GAG | ATG | CAC | ACA | GTG | ACA | GTG | 768 |
| His | Leu | Asn | Tyr | Thr | Thr | Glu | Gln | Val | Glu | Met | His | Thr | Val | Thr | Val | |
| | | | | 245 | | | | | 250 | | | | | 255 | | |
| CAG | TTG | CAG | GAA | TCG | TTC | GCG | GCA | AAC | CAC | TTG | TAC | TGC | ATC | AGG | AGA | 816 |
| Gln | Leu | Gln | Glu | Ser | Phe | Ala | Ala | Asn | His | Leu | Tyr | Cys | Ile | Arg | Arg | |
| | | | 260 | | | | | 265 | | | | | 270 | | | |
| GGA | GAT | TTG | CTC | ACA | CCG | GAG | GTG | CGC | ACT | TTT | GGC | CAA | CCT | GAC | AGG | 864 |
| Gly | Asp | Leu | Leu | Thr | Pro | Glu | Val | Arg | Thr | Phe | Gly | Gln | Pro | Asp | Arg | |
| | | | 275 | | | | | 280 | | | | | 285 | | | |
| TAT | GTG | ATT | CCA | CCA | CAG | ATC | TTC | CTC | CCG | AAA | GTC | CAT | AAC | TGC | AAG | 912 |
| Tyr | Val | Ile | Pro | Pro | Gln | Ile | Phe | Leu | Pro | Lys | Val | His | Asn | Cys | Lys | |
| | 290 | | | | | 295 | | | | | 300 | | | | | |
| AAG | CCG | ATT | CTT | AAA | AAA | ACT | ATG | ATG | CAG | CTC | TTC | TTG | TAT | GTT | AGG | 960 |
| Lys | Pro | Ile | Leu | Lys | Lys | Thr | Met | Met | Gln | Leu | Phe | Leu | Tyr | Val | Arg | |
| 305 | | | | | 310 | | | | | 315 | | | | | 320 | |
| ACA | GTT | AAG | GTC | GCA | AAA | AAT | TGT | GAC | ATT | TTT | GCC | AAA | GTC | AGA | CAA | 1008 |
| Thr | Val | Lys | Val | Ala | Lys | Asn | Cys | Asp | Ile | Phe | Ala | Lys | Val | Arg | Gln | |
| | | | | 325 | | | | | 330 | | | | | 335 | | |
| TTA | ATT | AAA | TCA | TCT | GAC | CTG | GAC | AAA | TAT | TCT | GCT | GTG | GAA | CTG | GTT | 1056 |
| Leu | Ile | Lys | Ser | Ser | Asp | Leu | Asp | Lys | Tyr | Ser | Ala | Val | Glu | Leu | Val | |
| | | | 340 | | | | | 345 | | | | | 350 | | | |
| TAC | TTA | GTA | AGC | TAT | ATG | GAG | TTC | CTT | GCC | GAT | CTA | CAA | GCT | ACC | ACC | 1104 |
| Tyr | Leu | Val | Ser | Tyr | Met | Glu | Phe | Leu | Ala | Asp | Leu | Gln | Ala | Thr | Thr | |
| | | 355 | | | | | 360 | | | | | 365 | | | | |
| TGC | TTC | TCA | GAC | ACA | CTT | TCT | GGT | GGC | TTA | CTA | ACA | AAG | ACC | CTT | GCA | 1152 |
| Cys | Phe | Ser | Asp | Thr | Leu | Ser | Gly | Gly | Leu | Leu | Thr | Lys | Thr | Leu | Ala | |
| | 370 | | | | | 375 | | | | | 380 | | | | | |
| CCG | GTG | AGG | GCT | TGG | ATA | CAA | GAG | AAA | AAG | ATG | CAG | CTG | TTT | GGT | CTT | 1200 |
| Pro | Val | Arg | Ala | Trp | Ile | Gln | Glu | Lys | Lys | Met | Gln | Leu | Phe | Gly | Leu | |
| 385 | | | | | 390 | | | | | 395 | | | | | 400 | |
| GAG | GAC | TAC | GCG | AAG | TTA | GTC | AAA | GCA | GTT | GAT | TTC | CAC | CCA | GTG | GAT | 1248 |
| Glu | Asp | Tyr | Ala | Lys | Leu | Val | Lys | Ala | Val | Asp | Phe | His | Pro | Val | Asp | |
| | | | | 405 | | | | | 410 | | | | | 415 | | |
| TTT | TCT | TTT | AAA | GTT | GAA | ACT | TGG | GAC | TTC | AGA | TTC | CAC | CCC | TTG | CAA | 1296 |
| Phe | Ser | Phe | Lys | Val | Glu | Thr | Trp | Asp | Phe | Arg | Phe | His | Pro | Leu | Gln | |
| | | | 420 | | | | | 425 | | | | | 430 | | | |
| GCG | TGG | AAA | GCC | TTC | CGA | CCA | AGG | GAA | GTG | TCG | GAT | GTA | GAG | GAA | ATG | 1344 |
| Ala | Trp | Lys | Ala | Phe | Arg | Pro | Arg | Glu | Val | Ser | Asp | Val | Glu | Glu | Met | |
| | | 435 | | | | | 440 | | | | | 445 | | | | |
| GAA | AGT | TTG | TTC | TCA | GAT | GGG | GAC | CTG | CTT | GAC | TGC | TTC | ACA | AGA | ATG | 1392 |
| Glu | Ser | Leu | Phe | Ser | Asp | Gly | Asp | Leu | Leu | Asp | Cys | Phe | Thr | Arg | Met | |
| | 450 | | | | | 455 | | | | | 460 | | | | | |

| | | | | | | | | | | | | | | | | |
|---|---|---|---|---|---|---|---|---|---|---|---|---|---|---|---|---|
| CCA | GCT | TAT | GCA | GTA | AAC | GCA | GAG | GAA | GAT | TTA | GCT | ACA | ATC | AGG | AAA | 1440 |
| Pro | Ala | Tyr | Ala | Val | Asn | Ala | Glu | Glu | Asp | Leu | Ala | Thr | Ile | Arg | Lys | |
| 465 | | | | 470 | | | | | 475 | | | | | | 480 | |
| ACG | CCC | GAG | ATG | GAT | GTC | GGT | CAA | GAA | GCC | AAA | GAA | CCT | GCA | GGA | GAC | 1488 |
| Thr | Pro | Glu | Met | Asp | Val | Gly | Gln | Glu | Ala | Lys | Glu | Pro | Ala | Gly | Asp | |
| | | | | 485 | | | | | 490 | | | | | 495 | | |
| AGA | AAT | CAA | TAC | TTA | AAC | CCT | GCA | GAA | ACT | TTC | CTC | AAC | AAG | CTC | CAC | 1536 |
| Arg | Asn | Gln | Tyr | Leu | Asn | Pro | Ala | Glu | Thr | Phe | Leu | Asn | Lys | Leu | His | |
| | | | 500 | | | | | 505 | | | | | 510 | | | |
| AGG | AAA | CAC | AGT | AGG | GAG | GTG | AAA | CAT | CAG | GCC | GTA | AAG | AAA | GCT | AAA | 1584 |
| Arg | Lys | His | Ser | Arg | Glu | Val | Lys | His | Gln | Ala | Val | Lys | Lys | Ala | Lys | |
| | | | 515 | | | | | 520 | | | | | 525 | | | |
| CGC | CTA | GCT | GAA | ATC | CAG | GAG | TCC | ATG | AGA | GCT | GAG | GGT | GAG | GCC | GAA | 1632 |
| Arg | Leu | Ala | Glu | Ile | Gln | Glu | Ser | Met | Arg | Ala | Glu | Gly | Glu | Ala | Glu | |
| | | 530 | | | | | 535 | | | | | 540 | | | | |
| CTA | AAT | GAG | ATG | AGC | GGG | GGC | ATG | AGG | GCA | ATA | CCT | AGC | AAC | GCA | GAA | 1680 |
| Leu | Asn | Glu | Met | Ser | Gly | Gly | Met | Arg | Ala | Ile | Pro | Ser | Asn | Ala | Glu | |
| 545 | | | | | 550 | | | | | 555 | | | | | 560 | |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn | Asp | Ala | Arg | Gln | Glu | Leu | Thr | Leu | Pro | Thr | Thr | |
| | | | | 565 | | | | | 570 | | | | | 575 | | |
| AAA | CCT | GTC | CCT | GCA | AGG | TGG | GAA | GAT | GCT | TCA | TTC | ACA | GAT | TCT | AGT | 1776 |
| Lys | Pro | Val | Pro | Ala | Arg | Trp | Glu | Asp | Ala | Ser | Phe | Thr | Asp | Ser | Ser | |
| | | | 580 | | | | | 585 | | | | | 590 | | | |
| GTG | AAA | GAG | GAG | CAA | GTG | AAA | CTC | CCT | GGA | AAA | GAA | GCC | GTT | GAG | ACA | 1824 |
| Val | Lys | Glu | Glu | Gln | Val | Lys | Leu | Pro | Gly | Lys | Glu | Ala | Val | Glu | Thr | |
| | | 595 | | | | | 600 | | | | | 605 | | | | |
| GCG | ACG | CAA | CAA | GTC | ATA | GAA | GGA | CTC | CCT | TGG | AAA | CAC | TGG | ATT | CCT | 1872 |
| Ala | Thr | Gln | Gln | Val | Ile | Glu | Gly | Leu | Pro | Trp | Lys | His | Trp | Ile | Pro | |
| | 610 | | | | | 615 | | | | | 620 | | | | | |
| CAA | CTA | AAT | GCT | GTT | GGA | TTC | AAG | GCG | CTG | GAA | ATT | CAG | AGG | GAT | AGG | 1920 |
| Gln | Leu | Asn | Ala | Val | Gly | Phe | Lys | Ala | Leu | Glu | Ile | Gln | Arg | Asp | Arg | |
| 625 | | | | | 630 | | | | | 635 | | | | | 640 | |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile | Met | Pro | Ile | Thr | Glu | Met | Val | Ser | Gly | Leu | Glu | |
| | | | | 645 | | | | | 650 | | | | | 655 | | |
| AAA | GAG | GAC | TTC | CCG | GAA | GGA | ACT | CCA | AAA | GAG | TTG | GCA | CGA | GAA | TTG | 2016 |
| Lys | Glu | Asp | Phe | Pro | Glu | Gly | Thr | Pro | Lys | Glu | Leu | Ala | Arg | Glu | Leu | |
| | | | 660 | | | | | 665 | | | | | 670 | | | |
| CTC | GCT | | | | | | | | | | | | | | | 2022 |
| Leu | Ala | | | | | | | | | | | | | | | |

(2) INFORMATION FOR SEQ ID NO:7:

(i) SEQUENCE CHARACTERISTICS:
        (A) LENGTH: 674 amino acids
        (B) TYPE: amino acid
        (D) TOPOLOGY: linear (ii) MOLECULE TYPE: protein (xi) SEQUENCE DESCRIPTION: SEQ ID NO:7:

| | | | | | | | | | | | | | | |
|---|---|---|---|---|---|---|---|---|---|---|---|---|---|---|
| Met | Ala | Lys | Val | Arg | Glu | Val | Tyr | Gln | Ser | Phe | Thr | Asp | Ser | Thr |
| 1 | | | | 5 | | | | | 10 | | | | | 15 |
| Lys | Thr | Leu | Ile | Gln | Asp | Glu | Ala | Tyr | Arg | Asn | Ile | Arg | Pro | Ile | Met |
| | | | 20 | | | | | 25 | | | | | 30 | | |
| Glu | Lys | His | Lys | Leu | Ala | Asn | Pro | Tyr | Ala | Gln | Thr | Val | Glu | Ala | Ala |
| | | | 35 | | | | | 40 | | | | | 45 | | |
| Asn | Asp | Leu | Glu | Gly | Phe | Gly | Ile | Ala | Thr | Asn | Pro | Tyr | Ser | Ile | Glu |
| | | | 50 | | | | | 55 | | | | | 60 | | |
| Leu | His | Thr | His | Ala | Ala | Ala | Lys | Thr | Ile | Glu | Asn | Lys | Leu | Leu | Glu |

|  65 |  |  |  |  |  | 70 |  |  |  |  | 75 |  |  |  |  | 80 |
|---|---|---|---|---|---|---|---|---|---|---|---|---|---|---|---|---|
| Val | Leu | Gly | Ser | Ile | Leu | Pro | Gln | Glu | Pro | Val | Thr | Phe | Met | Phe | Leu |
|  |  |  |  | 85 |  |  |  |  | 90 |  |  |  |  | 95 |  |
| Lys | Pro | Arg | Lys | Leu | Asn | Tyr | Met | Arg | Arg | Asn | Pro | Arg | Ile | Lys | Asp |
|  |  |  | 100 |  |  |  |  | 105 |  |  |  |  | 110 |  |  |
| Ile | Phe | His | Asn | Val | Ala | Ile | Glu | Pro | Arg | Asp | Val | Ala | Arg | Tyr | Pro |
|  |  | 115 |  |  |  |  | 120 |  |  |  |  | 125 |  |  |  |
| Lys | Glu | Thr | Ile | Ile | Asp | Lys | Leu | Thr | Glu | Ile | Thr | Thr | Asp | Thr | Ala |
|  | 130 |  |  |  |  | 135 |  |  |  |  | 140 |  |  |  |  |
| Tyr | Ile | Ser | Asp | Thr | Leu | His | Phe | Leu | Asp | Pro | Ser | Tyr | Ile | Val | Glu |
| 145 |  |  |  |  | 150 |  |  |  |  | 155 |  |  |  |  | 160 |
| Thr | Phe | Gln | Asn | Cys | Pro | Lys | Leu | Gln | Thr | Leu | Tyr | Ala | Thr | Leu | Val |
|  |  |  |  | 165 |  |  |  |  | 170 |  |  |  |  | 175 |  |
| Leu | Pro | Val | Glu | Ala | Ala | Phe | Lys | Met | Glu | Ser | Thr | His | Pro | Asn | Ile |
|  |  |  | 180 |  |  |  |  | 185 |  |  |  |  | 190 |  |  |
| Tyr | Ser | Leu | Lys | Tyr | Phe | Gly | Asp | Gly | Phe | Gln | Tyr | Ile | Pro | Gly | Asn |
|  |  | 195 |  |  |  |  | 200 |  |  |  |  | 205 |  |  |  |
| His | Gly | Gly | Gly | Ala | Tyr | His | His | Glu | Phe | Ala | His | Leu | Gln | Trp | Leu |
|  | 210 |  |  |  |  | 215 |  |  |  |  | 220 |  |  |  |  |
| Lys | Val | Gly | Lys | Ile | Lys | Trp | Arg | Asp | Pro | Lys | Asp | Ser | Phe | Leu | Gly |
| 225 |  |  |  |  | 230 |  |  |  |  | 235 |  |  |  |  | 240 |
| His | Leu | Asn | Tyr | Thr | Thr | Glu | Gln | Val | Glu | Met | His | Thr | Val | Thr | Val |
|  |  |  |  | 245 |  |  |  |  | 250 |  |  |  |  | 255 |  |
| Gln | Leu | Gln | Glu | Ser | Phe | Ala | Ala | Asn | His | Leu | Tyr | Cys | Ile | Arg | Arg |
|  |  |  | 260 |  |  |  |  | 265 |  |  |  |  | 270 |  |  |
| Gly | Asp | Leu | Leu | Thr | Pro | Glu | Val | Arg | Thr | Phe | Gly | Gln | Pro | Asp | Arg |
|  |  | 275 |  |  |  |  | 280 |  |  |  |  | 285 |  |  |  |
| Tyr | Val | Ile | Pro | Pro | Gln | Ile | Phe | Leu | Pro | Lys | Val | His | Asn | Cys | Lys |
|  | 290 |  |  |  |  | 295 |  |  |  |  | 300 |  |  |  |  |
| Lys | Pro | Ile | Leu | Lys | Lys | Thr | Met | Met | Gln | Leu | Phe | Leu | Tyr | Val | Arg |
| 305 |  |  |  |  | 310 |  |  |  |  | 315 |  |  |  |  | 320 |
| Thr | Val | Lys | Val | Ala | Lys | Asn | Cys | Asp | Ile | Phe | Ala | Lys | Val | Arg | Gln |
|  |  |  |  | 325 |  |  |  |  | 330 |  |  |  |  | 335 |  |
| Leu | Ile | Lys | Ser | Ser | Asp | Leu | Asp | Lys | Tyr | Ser | Ala | Val | Glu | Leu | Val |
|  |  |  | 340 |  |  |  |  | 345 |  |  |  |  | 350 |  |  |
| Tyr | Leu | Val | Ser | Tyr | Met | Glu | Phe | Leu | Ala | Asp | Leu | Gln | Ala | Thr | Thr |
|  |  | 355 |  |  |  |  | 360 |  |  |  |  | 365 |  |  |  |
| Cys | Phe | Ser | Asp | Thr | Leu | Ser | Gly | Gly | Leu | Leu | Thr | Lys | Thr | Leu | Ala |
|  | 370 |  |  |  |  | 375 |  |  |  |  | 380 |  |  |  |  |
| Pro | Val | Arg | Ala | Trp | Ile | Gln | Glu | Lys | Lys | Met | Gln | Leu | Phe | Gly | Leu |
| 385 |  |  |  |  | 390 |  |  |  |  | 395 |  |  |  |  | 400 |
| Glu | Asp | Tyr | Ala | Lys | Leu | Val | Lys | Ala | Val | Asp | Phe | His | Pro | Val | Asp |
|  |  |  |  | 405 |  |  |  |  | 410 |  |  |  |  | 415 |  |
| Phe | Ser | Phe | Lys | Val | Glu | Thr | Trp | Asp | Phe | Arg | Phe | His | Pro | Leu | Gln |
|  |  |  | 420 |  |  |  |  | 425 |  |  |  |  | 430 |  |  |
| Ala | Trp | Lys | Ala | Phe | Arg | Pro | Arg | Glu | Val | Ser | Asp | Val | Glu | Glu | Met |
|  |  | 435 |  |  |  |  | 440 |  |  |  |  | 445 |  |  |  |
| Glu | Ser | Leu | Phe | Ser | Asp | Gly | Asp | Leu | Leu | Asp | Cys | Phe | Thr | Arg | Met |
|  | 450 |  |  |  |  | 455 |  |  |  |  | 460 |  |  |  |  |
| Pro | Ala | Tyr | Ala | Val | Asn | Ala | Glu | Glu | Asp | Leu | Ala | Thr | Ile | Arg | Lys |
| 465 |  |  |  |  | 470 |  |  |  |  | 475 |  |  |  |  | 480 |
| Thr | Pro | Glu | Met | Asp | Val | Gly | Gln | Glu | Ala | Lys | Glu | Pro | Ala | Gly | Asp |
|  |  |  |  | 485 |  |  |  |  | 490 |  |  |  |  | 495 |  |

| | | | | | | | | | | | | | | |
|---|---|---|---|---|---|---|---|---|---|---|---|---|---|---|
| Arg | Asn | Gln | Tyr<br>500 | Leu | Asn | Pro | Ala | Glu<br>505 | Thr | Phe | Leu | Asn<br>510 | Lys | Leu | His |
| Arg | Lys | His<br>515 | Ser | Arg | Glu | Val | Lys<br>520 | His | Gln | Ala | Val | Lys<br>525 | Lys | Ala | Lys |
| Arg | Leu<br>530 | Ala | Glu | Ile | Gln | Glu<br>535 | Ser | Met | Arg | Ala | Glu<br>540 | Gly | Glu | Ala | Glu |
| Leu<br>545 | Asn | Glu | Met | Ser | Gly<br>550 | Gly | Met | Arg | Ala | Ile<br>555 | Pro | Ser | Asn | Ala | Glu<br>560 |
| Leu | Pro | Ser | Thr | Asn<br>565 | Asp | Ala | Arg | Gln | Glu<br>570 | Leu | Thr | Leu | Pro | Thr<br>575 | Thr |
| Lys | Pro | Val | Pro<br>580 | Ala | Arg | Trp | Glu | Asp<br>585 | Ala | Ser | Phe | Thr | Asp<br>590 | Ser | Ser |
| Val | Lys | Glu<br>595 | Glu | Gln | Val | Lys | Leu<br>600 | Pro | Gly | Lys | Glu | Ala<br>605 | Val | Glu | Thr |
| Ala | Thr | Gln<br>610 | Gln | Val | Ile | Glu<br>615 | Gly | Leu | Pro | Trp | Lys<br>620 | His | Trp | Ile | Pro |
| Gln | Leu<br>625 | Asn | Ala | Val | Gly<br>630 | Phe | Lys | Ala | Leu | Glu<br>635 | Ile | Gln | Arg | Asp | Arg<br>640 |
| Ser | Gly | Thr | Met | Ile<br>645 | Met | Pro | Ile | Thr | Glu<br>650 | Met | Val | Ser | Gly | Leu<br>655 | Glu |
| Lys | Glu | Asp | Phe<br>660 | Pro | Glu | Gly | Thr | Pro<br>665 | Lys | Glu | Leu | Ala | Arg<br>670 | Glu | Leu |
| Leu | Ala | | | | | | | | | | | | | | |

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

| | | | |
|---|---|---|---|
| GAATTGCTCG CTTAAGAGCT CATGAACAGA AGCC | | | 3 4 |

( 2 ) INFORMATION FOR SEQ ID NO:9:

( i ) SEQUENCE CHARACTERISTICS:
        ( A ) LENGTH: 597 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

| | | | | | |
|---|---|---|---|---|---|
| TCATCAAAAT | ATTTAGCAGC | ATTCCAGATT | GGGTTCAATC | AACAAGGTAC | GAGCCATATC | 60 |
| ACTTTATTCA | AATTGGTATC | GCCAAAACCA | AGAAGGAACT | CCCATCCTCA | AAGGTTTGTA | 120 |
| AGGAAGAATT | CTCAGTCCAA | AGCCTCAACA | AGGTCAGGGT | ACAGAGTCTC | CAAACCATTA | 180 |
| GCCAAAAGCT | ACAGGAGATC | AATGAAGAAT | CTTCAATCAA | AGTAAACTAC | TGTTCCAGCA | 240 |
| CATGCATCAT | GGTCAGTAAG | TTTCAGAAAA | AGACATCCAC | CGAAGACTTA | AAGTTAGTGG | 300 |
| GCATCTTTGA | AAGTAATCTT | GTCAACATCG | AGCAGCTGGC | TTGTGGGGAC | AGACAAAAA | 360 |
| AGGAATGGTG | CAGAATTGTT | AGGCGCACCT | ACCAAAAGCA | TCTTTGCCTT | TATTGCAAAG | 420 |
| ATAAAGCAGA | TTCCTCTAGT | ACAAGTGGGG | AACAAAATAA | CGTGGAAAAG | AGCTGTCCTG | 480 |
| ACAGCCCACT | CACTAATGCG | TATGACGAAC | GCAGTGACGA | CCACAAAAGA | ATTCCCTCTA | 540 |

TATAAGAAGG CATTCATTCC CATTTGAAGG ATCATCAGAT ACTAACCAAT ATTTCTC    597

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

GAATTGCTCG CTAAGAGCTC ATGAACAGAA GCC    33

( 2 ) INFORMATION FOR SEQ ID NO:11:

( i ) SEQUENCE CHARACTERISTICS:
        ( A ) LENGTH: 2124 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2124

( x i ) SEQUENCE DESCRIPTION: SEQ ID NO:11:

```
ATG  GCC  AAA  GTG  CGC  GAG  GTT  TAC  CAA  TCC  TTT  ACA  GAC  TCC  ACC  ACA     48
Met  Ala  Lys  Val  Arg  Glu  Val  Tyr  Gln  Ser  Phe  Thr  Asp  Ser  Thr  Thr
 1              5                        10                       15

AAA  ACT  CTC  ATC  CAA  GAT  GAG  GCT  TAT  AGA  AAT  ATT  CGT  CCC  ATC  ATG     96
Lys  Thr  Leu  Ile  Gln  Asp  Glu  Ala  Tyr  Arg  Asn  Ile  Arg  Pro  Ile  Met
                 20                       25                       30

GAA  AAA  CAT  AAA  CTA  GCT  AAC  CCG  TAC  GCT  CAA  ACG  GTT  GAA  GCG  GCT    144
Glu  Lys  His  Lys  Leu  Ala  Asn  Pro  Tyr  Ala  Gln  Thr  Val  Glu  Ala  Ala
         35                       40                       45

AAT  GAT  CTA  GAG  GGG  TTC  GGC  ATA  GCC  ACC  AAT  CCC  TAT  AGC  ATT  GAG    192
Asn  Asp  Leu  Glu  Gly  Phe  Gly  Ile  Ala  Thr  Asn  Pro  Tyr  Ser  Ile  Glu
     50                       55                       60

TTG  CAT  ACA  CAT  GCA  GCT  GCT  AAG  ACC  ATA  GAG  AAT  AAA  CTT  CTA  GAG    240
Leu  His  Thr  His  Ala  Ala  Ala  Lys  Thr  Ile  Glu  Asn  Lys  Leu  Leu  Glu
 65                       70                       75                       80

GTG  CTT  GGT  TCC  ATC  CTA  CCA  CAA  GAA  CCT  GTT  ACA  TTT  ATG  TTC  CTT    288
Val  Leu  Gly  Ser  Ile  Leu  Pro  Gln  Glu  Pro  Val  Thr  Phe  Met  Phe  Leu
                 85                       90                       95

AAA  CCC  AGG  AAG  CTA  AAC  TAC  ATG  AGA  AGA  AAC  CCG  CGG  ATC  AAG  GAC    336
Lys  Pro  Arg  Lys  Leu  Asn  Tyr  Met  Arg  Arg  Asn  Pro  Arg  Ile  Lys  Asp
        100                      105                      110

ATT  TTC  CAC  AAT  GTT  GCC  ATT  GAA  CCG  AGA  GAC  GTA  GCA  AGG  TAC  CCC    384
Ile  Phe  His  Asn  Val  Ala  Ile  Glu  Pro  Arg  Asp  Val  Ala  Arg  Tyr  Pro
    115                      120                      125

AAG  GAA  ACA  ATA  ATT  GAC  AAA  CTC  ACA  GAG  ATC  ACA  ACA  GAC  ACA  GCA    432
Lys  Glu  Thr  Ile  Ile  Asp  Lys  Leu  Thr  Glu  Ile  Thr  Thr  Asp  Thr  Ala
130                      135                      140

TAC  ATT  AGT  GAC  ACT  CTG  CAC  TTC  TTG  GAT  CCG  AGC  TAC  ATA  GTG  GAG    480
Tyr  Ile  Ser  Asp  Thr  Leu  His  Phe  Leu  Asp  Pro  Ser  Tyr  Ile  Val  Glu
145                      150                      155                      160

ACA  TTC  CAA  AAC  TGC  CCA  AAA  CTG  CAA  ACA  TTG  TAT  GCG  ACC  TTA  GTT    528
Thr  Phe  Gln  Asn  Cys  Pro  Lys  Leu  Gln  Thr  Leu  Tyr  Ala  Thr  Leu  Val
                 165                      170                      175

CTC  CCC  GTT  GAG  GCA  GCC  TTC  AAA  ATG  GAA  AGC  ACT  CAC  CCG  AAC  ATA    576
```

| | | | | | | | | | | | | | | |
|---|---|---|---|---|---|---|---|---|---|---|---|---|---|---|
| Leu | Pro | Val | Glu<br>180 | Ala | Ala | Phe | Lys | Met<br>185 | Glu | Ser | Thr | His | Pro<br>190 | Asn | Ile |

```
TAC AGC CTC AAA TAC TTC GGA GAT GGT TTC CAG TAT ATA CCA GGC AAC      624
Tyr Ser Leu Lys Tyr Phe Gly Asp Gly Phe Gln Tyr Ile Pro Gly Asn
        195                 200                 205

CAT GGT GGT GGA GCG TAC CAT CAT GAA TTT GCT CAT TTA CAA TGG CTC      672
His Gly Gly Gly Ala Tyr His His Glu Phe Ala His Leu Gln Trp Leu
    210                 215                 220

AAA GTG GGA AAG ATC AAA TGG AGG GAC CCC AAG GAT AGC TTT CTC GGA      720
Lys Val Gly Lys Ile Lys Trp Arg Asp Pro Lys Asp Ser Phe Leu Gly
225                 230                 235                 240

CAT CTC AAT TAC ACG ACT GAG CAG GTT GAG ATG CAC ACA GTG ACA GTG      768
His Leu Asn Tyr Thr Thr Glu Gln Val Glu Met His Thr Val Thr Val
            245                 250                 255

CAG TTG CAG GAA TCG TTC GCG GCA AAC CAC TTG TAC TGC ATC AGG AGA      816
Gln Leu Gln Glu Ser Phe Ala Ala Asn His Leu Tyr Cys Ile Arg Arg
                260                 265                 270

GGA GAT TTG CTC ACA CCG GAG GTG CGC ACT TTT GGC CAA CCT GAC AGG      864
Gly Asp Leu Leu Thr Pro Glu Val Arg Thr Phe Gly Gln Pro Asp Arg
            275                 280                 285

TAT GTG ATT CCA CCA CAG ATC TTC CTC CCG AAA GTC CAT AAC TGC AAG      912
Tyr Val Ile Pro Pro Gln Ile Phe Leu Pro Lys Val His Asn Cys Lys
    290                 295                 300

AAG CCG ATT CTT AAA AAA ACT ATG ATG CAG CTC TTC TTG TAT GTT AGG      960
Lys Pro Ile Leu Lys Lys Thr Met Met Gln Leu Phe Leu Tyr Val Arg
305                 310                 315                 320

ACA GTT AAG GTC GCA AAA AAT TGT GAC ATT TTT GCC AAA GTC AGA CAA     1008
Thr Val Lys Val Ala Lys Asn Cys Asp Ile Phe Ala Lys Val Arg Gln
            325                 330                 335

TTA ATT AAA TCA TCT GAC CTG GAC AAA TAT TCT GCT GTG GAA CTG GTT     1056
Leu Ile Lys Ser Ser Asp Leu Asp Lys Tyr Ser Ala Val Glu Leu Val
                340                 345                 350

TAC TTA GTA AGC TAT ATG GAG TTC CTT GCC GAT CTA CAA GCT ACC ACC     1104
Tyr Leu Val Ser Tyr Met Glu Phe Leu Ala Asp Leu Gln Ala Thr Thr
            355                 360                 365

TGC TTC TCA GAC ACA CTT TCT GGT GGC TTA CTA ACA AAG ACC CTT GCA     1152
Cys Phe Ser Asp Thr Leu Ser Gly Gly Leu Leu Thr Lys Thr Leu Ala
    370                 375                 380

CCG GTG AGG GCT TGG ATA CAA GAG AAA AAG ATG CAG CTG TTT GGT CTT     1200
Pro Val Arg Ala Trp Ile Gln Glu Lys Lys Met Gln Leu Phe Gly Leu
385                 390                 395                 400

GAG GAC TAC GCG AAG TTA GTC AAA GCA GTT GAT TTC CAC CCA GTG GAT     1248
Glu Asp Tyr Ala Lys Leu Val Lys Ala Val Asp Phe His Pro Val Asp
            405                 410                 415

TTT TCT TTT AAA GTT GAA ACT TGG GAC TTC AGA TTC CAC CCC TTG CAA     1296
Phe Ser Phe Lys Val Glu Thr Trp Asp Phe Arg Phe His Pro Leu Gln
                420                 425                 430

GCG TGG AAA GCC TTC CGA CCA AGG GAA GTG TCG GAT GTA GAG GAA ATG     1344
Ala Trp Lys Ala Phe Arg Pro Arg Glu Val Ser Asp Val Glu Glu Met
            435                 440                 445

GAA AGT TTG TTC TCA GAT GGG GAC CTG CTT GAC TGC TTC ACA AGA ATG     1392
Glu Ser Leu Phe Ser Asp Gly Asp Leu Leu Asp Cys Phe Thr Arg Met
    450                 455                 460

CCA GCT TAT GCA GTA AAC GCA GAG GAA GAT TTA GCT ACA ATC AGG AAA     1440
Pro Ala Tyr Ala Val Asn Ala Glu Glu Asp Leu Ala Thr Ile Arg Lys
465                 470                 475                 480

ACG CCC GAG ATG GAT GTC GGT CAA GAA GCC AAA GAA CCT GCA GGA GAC     1488
Thr Pro Glu Met Asp Val Gly Gln Glu Ala Lys Glu Pro Ala Gly Asp
            485                 490                 495

AGA AAT CAA TAC TTA AAC CCT GCA GAA ACT TTC CTC AAC AAG CTC CAC     1536
```

|  |  |  |  |  |  |  |  |  |  |  |  |  |  |  |  |
|---|---|---|---|---|---|---|---|---|---|---|---|---|---|---|---|
| Arg | Asn | Gln | Tyr<br>500 | Leu | Asn | Pro | Ala | Glu<br>505 | Thr | Phe | Leu | Asn | Lys<br>510 | Leu | His |

| AGG | AAA | CAC | AGT | AGG | GAG | GTG | AAA | CAT | CAG | GCC | GTA | AAG | AAA | GCT | AAA | 1584 |
|---|---|---|---|---|---|---|---|---|---|---|---|---|---|---|---|---|
| Arg | Lys | His<br>515 | Ser | Arg | Glu | Val<br>520 | Lys | His | Gln | Ala | Val<br>525 | Lys | Lys | Ala | Lys | |
| CGC | CTA | GCT | GAA | ATC | CAG | GAG | TCC | ATG | AGA | GCT | GAG | GGT | GAG | GCC | GAA | 1632 |
| Arg<br>530 | Leu | Ala | Glu | Ile | Gln<br>535 | Glu | Ser | Met | Arg | Ala<br>540 | Glu | Gly | Glu | Ala | Glu | |
| CTA | AAT | GAG | ATG | AGC | GGG | GGC | ATG | AGG | GCA | ATA | CCT | AGC | AAC | GCA | GAA | 1680 |
| Leu<br>545 | Asn | Glu | Met | Ser<br>550 | Gly | Gly | Met | Arg | Ala<br>555 | Ile | Pro | Ser | Asn | Ala | Glu<br>560 | |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn<br>565 | Asp | Ala | Arg | Gln | Glu<br>570 | Leu | Thr | Leu | Pro | Thr<br>575 | Thr | |
| AAA | CCT | GTC | CCT | GCA | AGG | TGG | GAA | GAT | GCT | TCA | TTC | ACA | GAT | TCT | AGT | 1776 |
| Lys | Pro | Val | Pro<br>580 | Ala | Arg | Trp | Glu | Asp<br>585 | Ala | Ser | Phe | Thr | Asp<br>590 | Ser | Ser | |
| GTG | AAA | GAG | GAG | CAA | GTG | AAA | CTC | CCT | GGA | AAA | GAA | GCC | GTT | GAG | ACA | 1824 |
| Val | Lys | Glu<br>595 | Glu | Gln | Val | Lys | Leu<br>600 | Pro | Gly | Lys | Glu | Ala<br>605 | Val | Glu | Thr | |
| GCG | ACG | CAA | CAA | GTC | ATA | GAA | GGA | CTC | CCT | TGG | AAA | CAC | TGG | ATT | CCT | 1872 |
| Ala | Thr<br>610 | Gln | Gln | Val | Ile | Glu<br>615 | Gly | Leu | Pro | Trp | Lys<br>620 | His | Trp | Ile | Pro | |
| CAA | CTA | AAT | GCT | GTT | GGA | TTC | AAG | GCG | CTG | GAA | ATT | CAG | AGG | GAT | AGG | 1920 |
| Gln<br>625 | Leu | Asn | Ala | Val | Gly<br>630 | Phe | Lys | Ala | Leu | Glu<br>635 | Ile | Gln | Arg | Asp | Arg<br>640 | |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile<br>645 | Met | Pro | Ile | Thr | Glu<br>650 | Met | Val | Ser | Gly | Leu<br>655 | Glu | |
| AAA | GAG | GAC | TTC | CCG | GAA | GGA | ACT | CCA | AAA | GAG | TTG | GCA | CGA | GAA | TTG | 2016 |
| Lys | Glu | Asp | Phe<br>660 | Pro | Glu | Gly | Thr | Pro<br>665 | Lys | Glu | Leu | Ala | Arg<br>670 | Glu | Leu | |
| CTC | GCT | AAG | AGC | TCG | CCC | GGG | GAT | CCA | GCT | TTC | GTT | CGT | ATC | GGT | TTC | 2064 |
| Leu | Ala | Lys<br>675 | Ser | Ser | Pro | Gly | Asp<br>680 | Pro | Ala | Phe | Val | Arg<br>685 | Ile | Gly | Phe | |
| GAC | AAC | GTT | CGT | CAA | GTT | CAA | TGC | ATC | AGT | TTC | ATT | GCG | CAC | ACA | CCA | 2112 |
| Asp | Asn<br>690 | Val | Arg | Gln | Val | Gln<br>695 | Cys | Ile | Ser | Phe | Ile<br>700 | Ala | His | Thr | Pro | |
| GAA | TCC | TAC | TGA | | | | | | | | | | | | | 2124 |
| Glu<br>705 | Ser | Tyr | | | | | | | | | | | | | | |

( 2 ) INFORMATION FOR SEQ ID NO:12:

( i ) SEQUENCE CHARACTERISTICS:
        ( A ) LENGTH: 707 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met<br>1 | Ala | Lys | Val | Arg<br>5 | Glu | Val | Tyr | Gln | Ser<br>10 | Phe | Thr | Asp | Ser<br>15 | Thr |
|---|---|---|---|---|---|---|---|---|---|---|---|---|---|---|
| Lys | Thr | Leu | Ile<br>20 | Gln | Asp | Glu | Ala | Tyr<br>25 | Arg | Asn | Ile | Arg | Pro<br>30 | Ile | Met |
| Glu | Lys | His<br>35 | Lys | Leu | Ala | Asn | Pro<br>40 | Tyr | Ala | Gln | Thr | Val<br>45 | Glu | Ala | Ala |
| Asn | Asp<br>50 | Leu | Glu | Gly | Phe | Gly<br>55 | Ile | Ala | Thr | Asn | Pro<br>60 | Tyr | Ser | Ile | Glu |
| Leu | His | Thr | His | Ala | Ala | Ala | Lys | Thr | Ile | Glu | Asn | Lys | Leu | Leu | Glu |

-continued

```
         65                        70                          75                       80
Val  Leu  Gly  Ser  Ile  Leu  Pro  Gln  Glu  Pro  Val  Thr  Phe  Met  Phe  Leu
                    85                      90                       95

Lys  Pro  Arg  Lys  Leu  Asn  Tyr  Met  Arg  Arg  Asn  Pro  Arg  Ile  Lys  Asp
                   100                     105                      110

Ile  Phe  His  Asn  Val  Ala  Ile  Glu  Pro  Arg  Asp  Val  Ala  Arg  Tyr  Pro
              115                     120                      125

Lys  Glu  Thr  Ile  Ile  Asp  Lys  Leu  Thr  Glu  Ile  Thr  Thr  Asp  Thr  Ala
         130                     135                      140

Tyr  Ile  Ser  Asp  Thr  Leu  His  Phe  Leu  Asp  Pro  Ser  Tyr  Ile  Val  Glu
145                     150                      155                           160

Thr  Phe  Gln  Asn  Cys  Pro  Lys  Leu  Gln  Thr  Leu  Tyr  Ala  Thr  Leu  Val
                   165                     170                      175

Leu  Pro  Val  Glu  Ala  Ala  Phe  Lys  Met  Glu  Ser  Thr  His  Pro  Asn  Ile
                   180                     185                      190

Tyr  Ser  Leu  Lys  Tyr  Phe  Gly  Asp  Gly  Phe  Gln  Tyr  Ile  Pro  Gly  Asn
              195                     200                      205

His  Gly  Gly  Gly  Ala  Tyr  His  His  Glu  Phe  Ala  His  Leu  Gln  Trp  Leu
         210                     215                      220

Lys  Val  Gly  Lys  Ile  Lys  Trp  Arg  Asp  Pro  Lys  Asp  Ser  Phe  Leu  Gly
225                     230                      235                           240

His  Leu  Asn  Tyr  Thr  Thr  Glu  Gln  Val  Glu  Met  His  Thr  Val  Thr  Val
                   245                     250                      255

Gln  Leu  Gln  Glu  Ser  Phe  Ala  Ala  Asn  His  Leu  Tyr  Cys  Ile  Arg  Arg
                   260                     265                      270

Gly  Asp  Leu  Leu  Thr  Pro  Glu  Val  Arg  Thr  Phe  Gly  Gln  Pro  Asp  Arg
              275                     280                      285

Tyr  Val  Ile  Pro  Pro  Gln  Ile  Phe  Leu  Pro  Lys  Val  His  Asn  Cys  Lys
         290                     295                      300

Lys  Pro  Ile  Leu  Lys  Lys  Thr  Met  Met  Gln  Leu  Phe  Leu  Tyr  Val  Arg
305                     310                      315                           320

Thr  Val  Lys  Val  Ala  Lys  Asn  Cys  Asp  Ile  Phe  Ala  Lys  Val  Arg  Gln
                   325                     330                      335

Leu  Ile  Lys  Ser  Ser  Asp  Leu  Asp  Lys  Tyr  Ser  Ala  Val  Glu  Leu  Val
                   340                     345                      350

Tyr  Leu  Val  Ser  Tyr  Met  Glu  Phe  Leu  Ala  Asp  Leu  Gln  Ala  Thr  Thr
              355                     360                      365

Cys  Phe  Ser  Asp  Thr  Leu  Ser  Gly  Gly  Leu  Leu  Thr  Lys  Thr  Leu  Ala
         370                     375                      380

Pro  Val  Arg  Ala  Trp  Ile  Gln  Glu  Lys  Lys  Met  Gln  Leu  Phe  Gly  Leu
385                     390                      395                           400

Glu  Asp  Tyr  Ala  Lys  Leu  Val  Lys  Ala  Val  Asp  Phe  His  Pro  Val  Asp
                   405                     410                      415

Phe  Ser  Phe  Lys  Val  Glu  Thr  Trp  Asp  Phe  Arg  Phe  His  Pro  Leu  Gln
                   420                     425                      430

Ala  Trp  Lys  Ala  Phe  Arg  Pro  Arg  Glu  Val  Ser  Asp  Val  Glu  Glu  Met
              435                     440                      445

Glu  Ser  Leu  Phe  Ser  Asp  Gly  Asp  Leu  Leu  Asp  Cys  Phe  Thr  Arg  Met
         450                     455                      460

Pro  Ala  Tyr  Ala  Val  Asn  Ala  Glu  Glu  Asp  Leu  Ala  Thr  Ile  Arg  Lys
465                     470                      475                           480

Thr  Pro  Glu  Met  Asp  Val  Gly  Gln  Glu  Ala  Lys  Glu  Pro  Ala  Gly  Asp
                   485                     490                      495
```

```
Arg Asn Gln Tyr Leu Asn Pro Ala Glu Thr Phe Leu Asn Lys Leu His
            500             505                 510
Arg Lys His Ser Arg Glu Val Lys His Gln Ala Val Lys Lys Ala Lys
        515             520                 525
Arg Leu Ala Glu Ile Gln Glu Ser Met Arg Ala Glu Gly Glu Ala Glu
    530             535             540
Leu Asn Glu Met Ser Gly Gly Met Arg Ala Ile Pro Ser Asn Ala Glu
545             550             555                         560
Leu Pro Ser Thr Asn Asp Ala Arg Gln Glu Leu Thr Leu Pro Thr Thr
                565             570                     575
Lys Pro Val Pro Ala Arg Trp Glu Asp Ala Ser Phe Thr Asp Ser Ser
            580             585                 590
Val Lys Glu Glu Gln Val Lys Leu Pro Gly Lys Glu Ala Val Glu Thr
        595             600             605
Ala Thr Gln Gln Val Ile Glu Gly Leu Pro Trp Lys His Trp Ile Pro
    610             615             620
Gln Leu Asn Ala Val Gly Phe Lys Ala Leu Glu Ile Gln Arg Asp Arg
625             630             635                         640
Ser Gly Thr Met Ile Met Pro Ile Thr Glu Met Val Ser Gly Leu Glu
            645             650                 655
Lys Glu Asp Phe Pro Glu Gly Thr Pro Lys Glu Leu Ala Arg Glu Leu
            660             665                 670
Leu Ala Lys Ser Ser Pro Gly Asp Pro Ala Phe Val Arg Ile Gly Phe
        675             680             685
Asp Asn Val Arg Gln Val Gln Cys Ile Ser Phe Ile Ala His Thr Pro
    690             695             700
Glu Ser Tyr
705
```

PLANTS RESISTANT TO INFECTION BY PVX

This application is a continuing application of application Ser. No. 07/804,862 filed Dec. 6, 1991, now abandoned, which is a continuation-in-part of application Ser. No. 07/771,912 filed Oct. 4, 1991, now abandoned.

FIELD OF THE INVENTION

This invention is related, in general, to plant genetic engineering and, more specifically, to a means and method for imparting resistance to a plant from viral infection using a gene encoding a non-structural viral protein.

BACKGROUND OF THE INVENTION

Many agriculturally important crops are susceptible to infection by plant viruses. These viruses can seriously damage a crop and drastically reduce its economic value to the grower. This eventually leads to a higher cost for the consumer. Attempts to control or prevent infection of a crop by a plant virus have been made, yet viral pathogens continue to be a significant problem in agriculture.

Potato virus X (PVX) is the type member of the potexvirus plant virus group. PVX is a positive-sense, single-stranded RNA virus that is surrounded by a repeating proteinaceous monomer, which is termed the coat protein (CP). The encapsidated virus has a flexous rod morphology, which is characteristic of the potexvirus group. PVX RNA resembles eucaryotic mRNA in that the 5' terminus is capped and the 3' end contains a poly A tail.

The PVX genomic RNA replicates through RNA intermediates in a DNA-independent fashion. PVX RNA has five open readings frames (ORFs). ORFs 1–5 have the potential for encoding proteins of 165, 22.5, 12, 8 and 25 kilodaltons (kDa), respectively. Except for ORF5, which encodes for the 25 kDa coat protein, the functions of ORFs 1–4 are not completely understood.

ORF1 is the largest of the open reading frames and encompasses more than two thirds of the viral genome. ORF1 is proposed to encode a replicase protein by virtue of its sequence similarity to other known replicase genes. In particular, ORF1 contains several conserved motifs that are found in other replicase genes, such as the NTP binding domain and the GDD motif (Hodgman 1988). The NTP domain is a conserved 7–8 amino acid sequence that is found in many proteins, including replicases, ATPases and helicases. The function of the NTP domain is to bind and subsequently cleave a nucleotide triphosphate. The GDD domain is larger than the NTP domain and contains a glycine amino acid residue (G) followed by two aspartate amino acid residues (D). GDD domains are often found in replicase proteins and are believed to be involved in catalytic function.

The host range of PVX is extremely large. PVX infects at least 240 species in 16 plant families, although more than half of the species belong to members of the Solanaceae family, including potato, tobacco and tomato (Purcifull and Edwardson, 1981). Potato plants are particularly susceptible to infection by PVX. Infection by PVX of a potato crop results in a substantially reduced yield. Moreover, simultaneous infection by PVX and the potyvirus Potato virus Y (PVY) cause a devastating synergistic effect. A combined PVX and PVY infection can reduce yields as much as 90% (deBokx, 1986). Because most of the commercial potato cultivars are propagated vegetatively, maintaining virus-free lines is of critical importance to the potato grower.

PVX is a mechanically-transmitted virus. Healthy plants commonly become infected if they come in contact with PVX infected plants (Loughnance and Murphy, 1938; deBokx, 1972). PVX can also be spread by walking through a field, or by handling the plants. Infectious PVX has been detected on the fabric of trousers a month after they were worn djuring a walk among infected potato plants. In addition, small animals can also spread PVX; infectious PVX has been recovered from dog and rabbit fur a day after the animals had run among infected plants (Todd 1957). Because of the ease of transmission of PVX, potato growers must adhere to strict cultural practices to control PVX infection. These methods include isolating plants from sources of infection, wide spacing to avoid plant contact, and sterilization of cultivating and harvesting tools. Fields must also be visually inspected for morphological signs of infection. Plants showing visual signs of PVX infection are destroyed by the grower. Farmers plant "potato seeds," which are actually not true seeds, but rather pieces of potato tubers. Before "potato seeds" can be sold to the farmer, they must pass a rigorous series of tests to be certified virus free. PVX infection of "potato seeds" is a cause of seed de-certification.

It has previously been shown that expression of a plant virus capsid protein, which is termed the c(oat protein, in a plant can confer resistance to the homologous virus and to related viruses (Abel et al. 1986; Tumer et al. 1987: Cuozzo et al. 1988; Hemenway et al. 1988; Stark and Beachy 1989; Lawson et al. 1990;

Kaniewski et al. 1990). In these studies, resistance to virus disease is defined as either reduced incidence of infection, delayed symptom development, reduced virus replication or viral antigen levels, or slower to no systemic virus movement. Expression of the virus coat protein in these transgenic plants is responsible for the observed effects in the reduction of virus disease by an as yet undetermined mechanism (Abel et al. 1986; van Dun et al. 1988). This type of protection to viral infection is termed coat protein mediated protection.

A portion of the proposed replicase gene from tobacco mosaic virus (TMV) recently has been found to provide resistance against TMV when expressed in tobacco plants (Golemboski et al. 1990). In TMV, two proteins, the 183 kDa and 126 kDa proteins, have been speculated to be replicase components (Ishikawa et al. 1986). The 183 kDa protein is a readthrough product of the 126 kDa sequence. The 126 kDa protein contains the NTP binding motif. The 183 kd protein contains both the NTP and GDD motifs. More specifically, the 54 kDa readthrough portion of the 183 kDa protein is the portion that contains the GDD motif. Thus, the 183 kd protein of TMV most resembles the PVX 165 kd protein. Golemboski et al. (1990) found that transgenic tobacco plants expressing the 54 kDa readthrough portion were protected against infection by TMV. They did not, however, observe protection in transgenic plants expressing the 126 kDa protein. Moreover, they did not report any protection data on plants expressing the 183 kd protein.

Others have conducted protection experiments with transgenic plants expressing components of non-structural viral proteins. For example, van Dun et al. (1988) analyzed protection in tobacco plants expressing either of two genes encoding proteins involved in the replication of alfalfa mosaic virus (AlMV). These plants were transformed with RNAs 1 or 2 of AlMV, which encode proteins P1 and P2, respectively. The polypeptides encoded by these RNAs have amino acid homologies to other viral replicases, and both RNAs are known to be essential for replication. In contrast to the PVX ORF1, the NTP and GDD binding motifs for AlMV reside on different RNAs and consequently different proteins. In particular, P1 on RNA1 has homology to the NTP binding motif and P2 on RNA2 has homology to the GDD motif. Plants expressing either RNA1 or RNA2 were not protected against infection by AlMV. In addition, plants expressing both RNAs 1 and 2 were likewise not protected against infection by AlMV (Taschner et al. 1991).

SUMMARY OF THE INVENTION

A cDNA sequence encoding ORF1 of the PVX genome has been prepared that provides resistance to infection by PVX in plants expressing the DNA sequence at a sufficient level. It is believed that ORF1 of the PVX genome functions as a replicase gene in PVX. The DNA sequence of ORF1 is inserted into the desired plant species, preferably potato or tomato, and expressed therein to confer resistance to PVX. The DNA sequence encoding the PVX replicase gene is 4455 nucleotides in length, including 84 nucleotides at the 5' end that serve as an untranslated leader sequence. The gene encodes a protein of 1457 amino acids.

In one embodiment of the present invention, a plant gene is provided which comprises a promoter that functions in plant cells to cause the production of an RNA sequence, a DNA sequence encoding a PVX replicase gene, and a 3' non-translated DNA sequence that functions in plants to cause the addition of polyadenylated ribonucleotides to the 3' end of the RNA sequence. This plant gene may be inserted into a plant to express the PVX replicase gene. A plant expressing the PVX replicase gene at a sufficient level exhibits resistance to PVX.

In an alternate embodiment of the present invention, a DNA sequence including nucleotides 1–2106 of the PVX replicase gene is provided. This DNA sequence may be inserted into a desired plant, preferably potato or tomato, to provide resistance to infection by PVX in plants expressing the DNA sequence at a sufficient level. This DNA sequence is referred to as a truncated PVX replicase gene.

A method for providing resistance to infection by PVX in plants of the Solanaceae family is also provided. The method comprises transforming cells of the Solanaceae plant with a DNA sequence encoding a PVX replicase gene and selecting transformed plants that express the PVX replicase gene at a level sufficient to render the plants resistant to infection by PVX.

In a further embodiment of the present invention, a plant gene comprising a modified transcriptional promoter from cauliflower mosaic virus (eCaMV35S), a small synthetic fragment of DNA that facilitates linking the promoter to the replicase gene, an 84 nucleotide leader sequence derived from the PVX replicase coding region, an isolated DNA sequence encoding a PVX replicase gene, an additional small synthetic fragment of DNA that facilitates linking the gene to a 3' termination signal, and a 3' non-translated region that encodes a polyadenylation signal is also provided. This gene can be inserted into a plant to confer high levels of resistance to PVX.

The present invention provides a PVX replicase cDNA sequence that, when expressed in a transgenic plant, provides a reduced to no incidence of infection by PVX, and a reduced or no viral antigen level in both inoculated and systemic leaves.

BRIEF DESCRIPTION OF THE DRAWING

FIG. 1 illustrates the cDNA sequence and the predicted amino acid sequence of a PVX genomic clone that includes the replicase gene sequence. The PVX genomic leader sequence is also shown positioned upstream of the replicase gene coding region.

FIG. 2 illustrates the cDNA sequence of a truncated PVX replicase gene and its predicted amino acid sequence.

FIG. 7 is a graph illustrating the systemic viral antigen level of tobacco plant lines expressing the PVX replicase protein and control lines.

FIG. 8 is a graph illustrating the viral antigen level in inoculated leaves from tobacco plant lines expressing the PVX replicase protein and control lines.

FIG. 12 illustrates the DNA sequence of the full-length transcript promoter from figwort mosaic virus.

FIG. 13 illustrates the DNA sequence of the truncated PVX gene extended by 33 codons.

DESCRIPTION OF THE PREFERRED EMBODIMENTS

Figure 3:
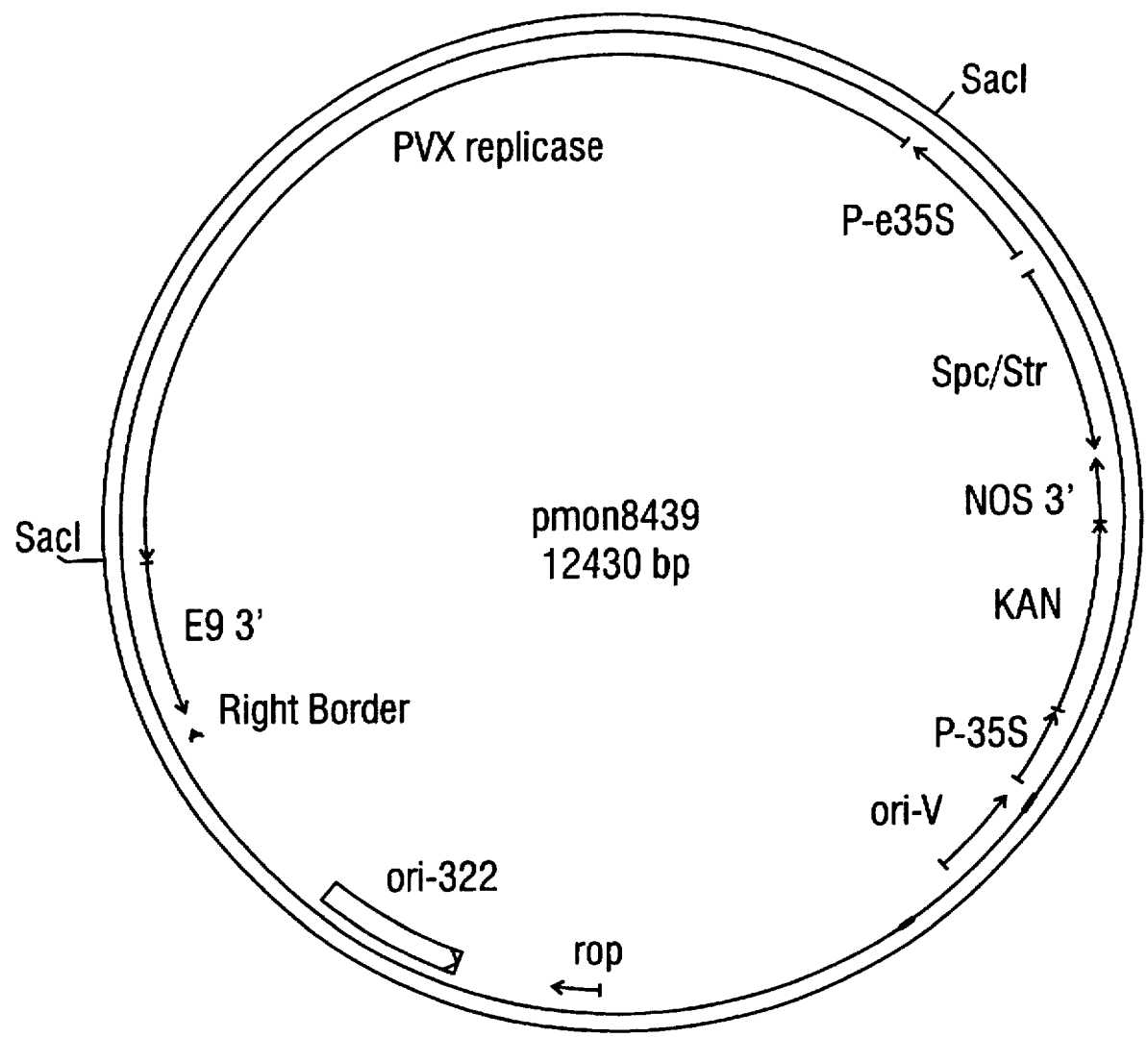
FIG. 3 illustrates a physical map of the plasmid pMON8439.
Figure 4:
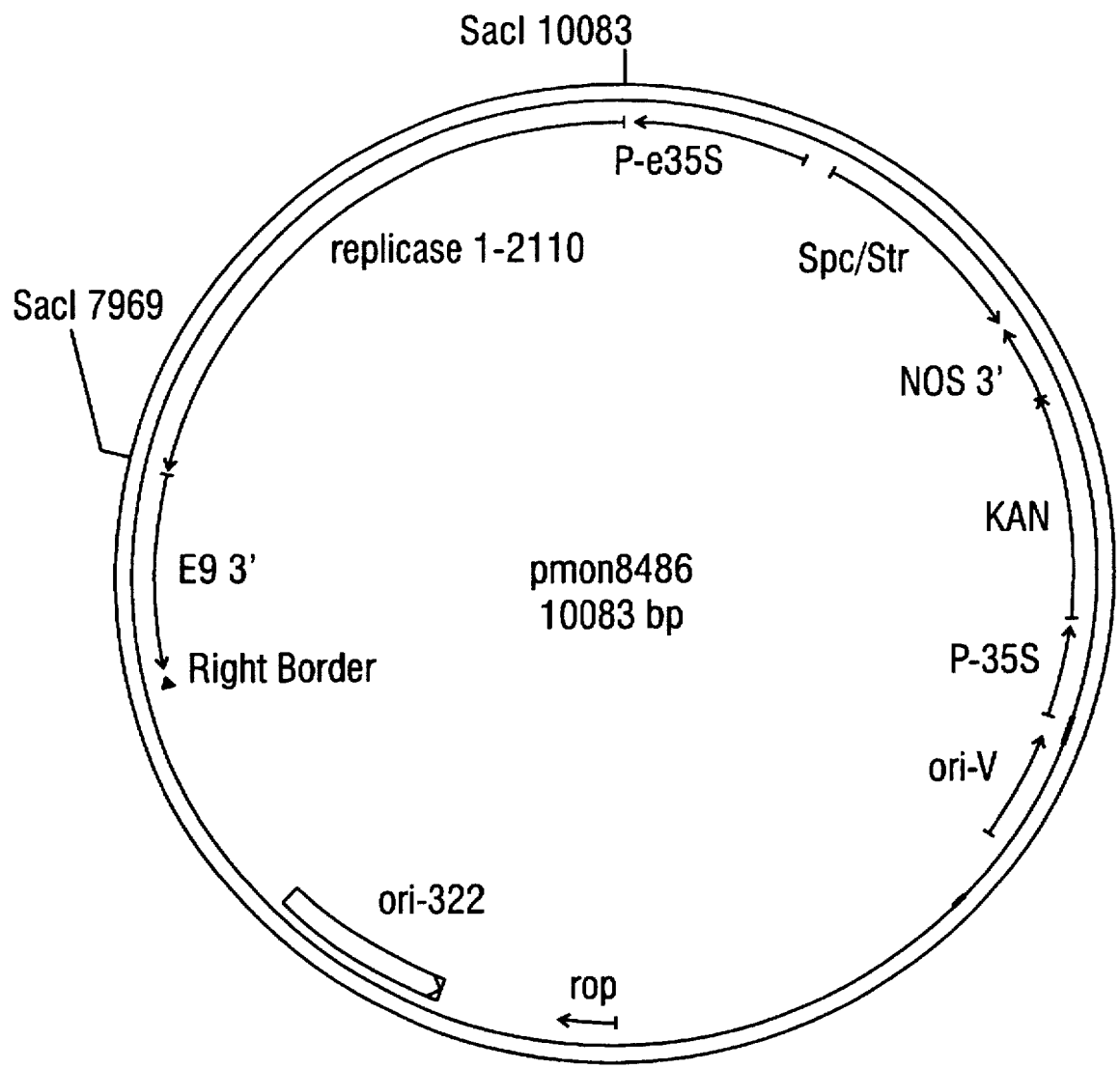
FIG. 4 illustrates a physical map of the plasmid of pMON8486.

The present invention provides a means and a method for conferring resistance in plants to infection from potato virus X (PVX). The resistance is provided by the expression in the plant of an isolated DNA sequence consisting essentially of nucleotides encoding a PVX replicase gene. A PVX replicase gene isolated from any of the various PVX strains or isolates can be used in the present invention. The corresponding replicase gene from different PVX strains is consistently the largest and most 5' ORF of the viral genome. The amino acid sequence of reported PVX replicase ORFs exhibit a high degree of similarity when compared to each other. The PVX replicase amino acid sequence disclosed herein (SE ID NO: 2) is 98% similar to the corresponding sequence of a Dutch strain of PVX replicase and the nucleotide sequences are 97% similar (Huisman et al. 1988). Replicase genes from two Russian PVX strains also are 98% identical at the amino acid level to the Dutch PVX strain (Skryabin et al. 1988). Thus, the similarity exhibited in the amino acid sequence of PVX replicases from PVX strains obtained from diverse geographic regions illustrates that any PVX strain or isolate could be used as the source of a PVX replicase gene for use in this invention.

For the purposes of illustrating the present invention, a field isolate of PVX obtained from Dr. Pete E. Thomas of the United States Department of Agriculture in Prosser, WA was used as the source of the replicase gene. The PVX genome was isolated from a cDNA library made from RNA recovered from purified PVX virions. The cDNA library was made from the PVX isolate obtained from Dr. Thomas.

A full-length PVX genomic clone was isolated and characterized from the cDNA library (Hemenway et al. 1990). When the full-length PVX clone is fused to the T7 bacteriophage transcriptional promoter, infectious PVX RNA can be synthesized in vitro, thus experimentally proving that the PVX cDNA retains the sequence in a formation necessary for biological activity. The cDNA sequence of the PVX replicase gene is 4455 nucleotides in length including a 5' non-translated leader sequence and is illustrated in FIG. 1. The replicase coiling region begins at nucleotide position 85 and contains 4371 nucleotides or 1,457 codons. The PVX replicase coding region is designated as SE ID NO: 1. The deduced amino acid sequence is shown below the cDNA sequence in FIG. 1 and is identified as SE ID NO: 2. The first 84 nucleotides of the PVX genome are referred to as the genomic RNA leader sequence and are untranslated. The cDNA sequence of this untranslated leader sequence is also illustrated in FIG. 1 and is identified as SE ID NO: 3.

This PVX replicase cDNA sequence was the source used to produce the replicase DNA sequences of this invention. The nucleotide sequence of the replicase gene was modified at the 5' and 3' ends to facilitate cloning. DNA sequences were added by site-directed mutagenesis, using the method described by Kunkel (1985), to incorporate SacI sites into the DNA sequence. The oligonucleotide primers used to create the 5' and 3' SacI sites are, respectively, as follows:

5'-TATGGTTTAGTTTTCGAGCTCTATAGTGAGTCGTAT-3' (SEQ ID NO: 4); and
5'-GGTAACTTAACGGGAGCTCTTAAAGAAAGTTTC-3' (SEQ ID NO: 5).

The resulting sequence contained SacI restriction endonuclease recognition sites immediately upstream of position 1 and downstream of the stop codon at position 4455. The resulting SacI fragment that contained the PVX replicase gene was inserted into a plant transformation vector and used in experiments that tested its ability to confer resistance to infection by PVX in tobacco plants as further described in the examples to follow.

A truncated PVX replicase gene is prepared by inserting a stop codon and a SacI site between codons 674 and 675 of the full-length PVX replicase sequence to form a new 3' SacI site. The final 783 codons of the PVX replicase sequence are removed as a SacI - SacI fragment. The cDNA sequence and derived amino acid sequence of this truncated PVX replicase gene is illustrated in FIG. 2. The DNA sequence in FIG. 2 includes the 84 nucleotide PVX leader sequence and the 3' SacI site, but does not include a stop codon after codon 674. A truncated PVX replicase DNA sequence comprising nucleotides 815–2106 is designated as SE ID NO: 6 and the derived amino acid sequence of this truncated PVX replicase is designated SE ID NO: 7.

The replicase gene can be inserted into a suitable plant transformation vector for transformation into the desired plant species. Suitable plant transformation vectors include those derived from a Ti plasmid of Agrobacterium tumefaciens, in addition to those disclosed, for example, by Herrera-Estrella (1983), Bevan (1984), Klee (1985) and U.S. Pat. No. 4,940,838, issued to Schilperoort et al. A plant transformation vector preferably includes all of the necessary elements needed for transformation of plants or plant cells. Typical plant transformation vectors comprise selectable marker genes, one or both of the T-DNA borders, cloning sites, appropriate bacterial genes to facilitate identification of transconjugates, broad host-range replication and mobilization functions and other elements as desired.

The PVX replicase cDNA sequence is inserted into a plant transformation vector as a gene capable of being expressed in a plant. For the purposes of this invention, a "gene" is defined as an element or combination of elements that are capable of being expressed in a plant, either alone or in combination with other elements. Such a gene generally comprises, in the following order, a promoter that functions in plant cells, a 5' non-translated leader sequence, a DNA sequence coding for the desired protein, and a 3' non-translated region that functions in plants to cause the addition of polyadenylated ribonucleotides to the 3' end of the mRNA transcript. In this definition, each above described element is operationally coupled to the adjacent element. A plant gene comprising the above elements can be inserted by known, standard recombinant DNA methods into a plant transformation vector and other elements added to the vector when necessary. A plant transformation vector can be prepared that has all of the necessary elements for plant expression except the desired DNA coding region or portion thereof, which can readily be added to the vector by known methods.

Promoters that are known or found to cause transcription of DNA in plant cells can be used in the present invention. Such promoters can be obtained from a variety of sources such as plants or plant DNA viruses and include, but are not necessarily limited to, promoters isolated from the caulimovirus group, such as the cauliflower mosaic virus 19S and 35S (CaMV19S and CaMV35S) transcript promoters or the figwort mosaic virus full-length transcript promoter (FMV35S). The FMV35S promoter causes a high level of uniform expression of a coding region coupled thereto in most plant tissues. Other useful promoters include the enhanced CaMV35S promoter (eCaMV35S) as described by Kay et al. (1987) and the small subunit promoter of ribulose 1,5-bisphosphate carboxylase oxygenase (RUBISCO).

The promoter selected should be capable of causing sufficient expression of the PVX replicase( gene to result in the production of an effective amount of the replicase RNA or replicase protein to render the plant cells and plants regenerated therefrom substantially resistant to infection by P)TX. In particular, the enhanced CaMV35S promoter or the FMV35S promoter is useful in the present invention. The enhanced CaMV35S promoter causes sufficient levels of the replicase mRNA sequence to be produced in tobacco cells to yield tobacco plants that are highly resistant to infection by PVX.

The nucleotide sequence of an FMV35S promoter is provided in FIG. 12 and is designated SEQ ID NO: 9. Those skilled in the art will know that other promoters can be used with advantageous results in conjunction with the DNA sequences of the present invention and are within the scope of this invention.

The mRNA produced by the promoter contains both the coding region of the replicase gene and the 5' non-translated leader sequence. This non-translated leader sequence can be derived from any suitable source and car, be specifically modified to increase translation of the mRNA. The 5' non-translated region can be obtained from the promoter selected to express the gene, the native 5' leader sequence of the gene or coding region to be expressed, viral RNAs, suitable eucaryotic genes, or a synthetic gene sequence. The present invention is not limited to the construct presented in the following examples, wherein the non-translated region is derived from 45 nucleotides from the eCaMV35S promoter, 6 nucleotides from the linker cassette, and 84 nucleotides of the native PVX leader sequence. The non-translated leader sequence can also be derived from an unrelated promoter or viral coding region as described.

The 3' non-translated region of the chimeric plant gene contains a polyadenylation signal that functions in plants to cause the addition of polyadenylated ribonucleotides to the 3' end of the mRNA. Examples of suitable 3' regions are the 3' transcribed, non-translated regions containing the polyadenylation signal of Agrobacterium tumor inducing (Ti) plasmid genes, such as the NOS gene, and plant genes such as the soybean storage protein genes and the small subunit promoter of the RUBISCO gene. An example of a preferred 3' region is that from the RUBISCO gene from pea (referred to as E9 3' in the figures) as described in the examples below.

The above described plant transformation vectors containing the PVX replicase gene may be used to transform plants of the Solanaceae family. In particular, infection by PVX is a persistent problem in potato and can infect tomato. An Agrobacterium-mediated transformation protocol is known to be effective in transforming members of the Solanaceae family. Other transformation techniques capable of inserting DNA into plant cells such as, but not limited to, electroporation, microprojectile or particle gun technology, and chemicals that increase free DNA uptake may also be used.

When an Agrobacterium mediated transformation is used, the desired transformation vector is mobilized into a suitable Agrobacterium strain. The ABI Agrobacterium strain is described for exemplary purposes. The desired transformation vector is mobilized into an ABI Agrobacterium strain by the triparental conjugation system using the helper plasmid pRK2013 (Ditta et al. 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by Agrobacterium. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the Solanaceae family are known. In particular, various transformation and regeneration protocols for potato and tomato have been established. Exemplary protocols are described below.

For potato, two protocols are described below, but those skilled in the art know that modifications and optimization to the protocols can be made. Agrobacterium containing the desired plant transformation vector is grown overnight in 2 mls of LBSCK broth. LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0. The following day, the bacteria are diluted 1:10 with MSO or until an OD (optical density) reading of 0.2–0.3 is established. MSO contains 4.4 g MX salts (Sigma Chemical Co., St. Louis, MO), 30 g sucrose and 2 ml $B_5$ vitamin (500X) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma Chemical Co., St. Louis, MO), 30 g sucrose, 0.17 g $NaH_2PO_4H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10 MSO with 1.5 mls of TxD cells overlayed with wetted filter paper. Approximately 50 explants are placed on each plate.

After a two (2) day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein which confers resistance to the antibiotic kanamycin to the plant. If the plant is positive for expression of the protein, the plant is kept for further study and maintained in tissue culture.

Alternately, the explants may be placed on callus induction plates containing MSO plus 3.0 mg/l BA (6 benzylaminopurine) and 0.01 mg/l NAA for four (4) weeks with 100 mg/l kanamycin for selection. For shoot induction, the explants are placed on MSO plus 0.3 mg/l $GA_3$ only and 100 mg/ml kanamycin for selection. Shoots begin to appear at about 8 weeks. Shoots are recallused on MSP-5 with 200 mg/ml kanamycin and assayed in two weeks. MSP-5 contains 4.4 g MS salts (Sigma), 5 ml SLLX vitamins (200 X), 30 g sucrose, 2.25 ml BAP, 0.186 ml NAA in 1 liter, pH 5.6 and 0.2% Gelrite agar.

After the potato plant has been transformed and after transformed callus has been identified, the transformed callus tissue is regenerated into whole plants. Any known method of regeneration of potato plants can be used in this invention.

For tomato, the transformation protocol described in McCormick et al. (1986) can generally be used. In particular, cotyledons are obtained from 7–8 day old seedlings. The seeds are surface sterilized for 20 minutes in 30% Clorox bleach and are germinated in Plantcons boxes on Davis germination media. Davis germination media is comprised of 4.3 g/l MS salts, 20 g/l sucrose and 10 mls/l Nitsch vitamins, pH5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C. 40% humidity under cool white lights with an intensity of 80 einsteins $m^{-2}s-1$. The photoperiod is 16 hours of light and 8 hours of dark.

Once germination has occurred, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1 X MS salts, 3% sucrose, 1 X Nitsch vitamins, 2.0 mg/l zeatin, pH 5.8. This solution is autoclaved with 0.8% Noble Agar.

The cotyledons are pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCL 0.2 mls of a 0.5 mg/ml solution of kinetin and 0.1 ml of a 0.2 mg/ml solution of 2.4 D, this solution is adjusted to pH 6.0 with KOH. These plates are overlaid with 1.5–2.0 mls of tobacco suspension cells (TXD's) and a sterile Whatman fitter which is soaked in 2 COO5 K media. 2 COO5 K media is composed of 4.3 g/l Gibco MS salt mixture, 1 ml B5 vitamins (1000X stock), 30 g/l sucrose, 2 mls/l PCPA from 2 mg/ml stock, and 10 µl/l kinetin from 0.5 mg/l stock. The cotyledons are cultured for 1 day in a growth chamber at 25 ° C. under cool white lights with a light intensity of 40–50 einsteins $m^{-2}s^{-1}$ with a continuous light photoperiod.

Cotyledons are then inoculated with a log phase solution of Agrobacterium containing the desired transgenic gene. The concentration of the Agrobacterium is approximately $5 \times 10^8$ cells/ml. The cotyledons are allowed to soak in the bacterial solution for six minutes and are then blotted to remove excess solution on sterile Whatman filter disks and are subsequently replaced to the original feeder plate where they are allowed to co-culture for 2 days. After the two days, cotyledons are transferred to selection plates containing Davis regeneration media with 2 mg/l zeatin riboside, 500 µg/ml carbenicillin, and 100 µg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly from callus tissue and are planted on rooting selection plates. These plates contain 0.5 X MSO containing 50 µg/ml kanamycin and 500 µg/ml carbenicillin. These shoots form roots on the selection media within two weeks. If no shoots appear after 2 weeks, shoots are trimmed and replanted on the selection media. Shoot cultures are incubated in percivals at a temperature of 22 ° C. Shoots with roots are then potted when roots are about 2 cm in length. The plants are hardened off in a growth chamber at 21 ° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and allowed to mature.

The following examples are provided to elucidate better the practice of the present invention and should not be interpreted in any way to limit the scope of the present invention. Those skilled in the art will recognize that various modifications can be made to the methods and genes described herein while not departing from the spirit and scope of the present invention.

EXAMPLE 1

Figure 5:
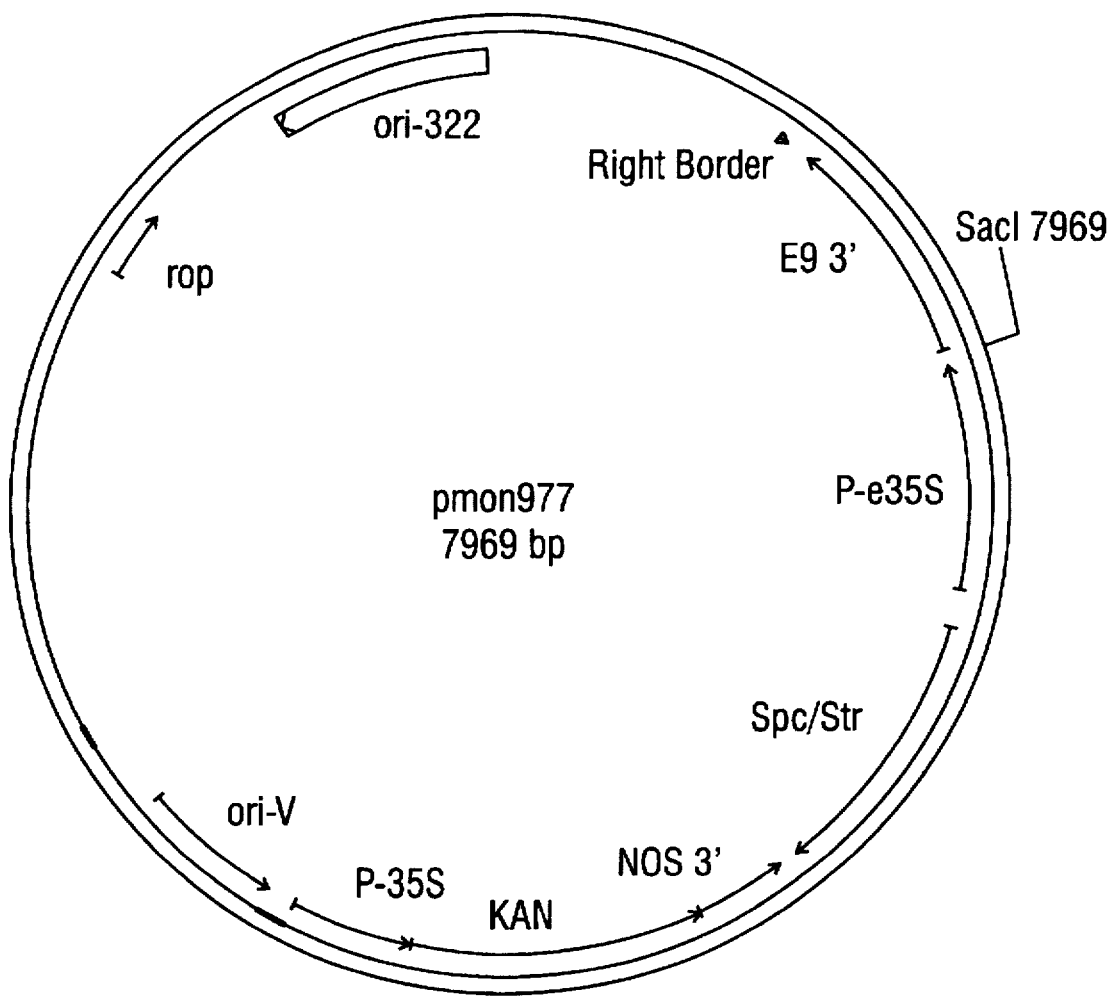
FIG. 5 illustrates a physical map of the plasmid pMON977.

The DNA coding sequence for the PVX replicase gene (SEQ ID NO: 1) was engineered into pMON977, which is a single border plant transformation vector, to study its ability to confer resistance to PVX in plants expressing the replicase gene. A physical map of pMON977 is shown in FIG. 5. The resulting vector containing the PVX replicase gene is pMON8439, and is illustrated in FIG. 3.

Plasmid pMON8439 contains the following DNA segments. Starting near the bottom of FIG. 3 is the origin of bacterial replication for maintenance in E. coli (ori-322) and includes the bom site for conjugational transfer into Agrobacterium tumefaciens cells. Moving in a counter-clockwise direction, next is the ori-V, which is the vegetative origin of replication (Stalker et al. 1981). Next is the chimeric gene used as the selectable marker. The chimera includes 0.35 kilobase (kb) of cauliflower mosaic virus 35S promoter (P-35S) (Odell et al. 1985), a 0.83 kb neomycin phosphotransferase type II gene (KAN), and a 0.25 kb 3' nontranslated region of the nopaline synthase gene (NOS 3' ) (Fraley et al. 1983). Next is the 0.93 kb fragment isolated from transposon Tn7 that encodes the bacterial spectinomycin/streptomycin resistance (Spc/Str), which is a determinant for selection in E. coli and Agrobacterium tumefaciens (Fling et al. 1985). The next sequence contains a second chimeric gene, including PVX replicase. A 0.64 kb DNA sequence containing the enhanced CaMV35S promoter functions as the transcriptional promoter for the PVX replicase coding region (SEQ ID NO: 1). The chimeric gene ends with the 0.65 kb of the E9 3'region from the pea small subunit RUBISCO gene (Coruzzi et al. 1984).

Prior to transformation, E. coli containing pMON8439 were mated into Agrobacterium ABI by a triparental mating with the helper plasmid pRK2013 (Ditta et al. 1980). ABI is the A208 Agrobacterium tumefaciens strain carrying the disarmed pTiC58 plasmid pMP90RK (Koncz and Schell, 1986). The disarmed Ti plasmid provides the trfA gene functions that are required for autonomous replication of the PMON vector after the conjugation into the ABI strain. When plant tissue is incubated with the ABI::pMON conjugate, the vector is transferred to the plant cells by the vir functions encoded by the disarmed pMP90RK Ti plasmid. Agrobacterium were grown 30 hours in LB media (10 g tryptone, 5 g yeast extract and 5 g NaCl per liter) with 25 µg/ml chloramphenicol and 50 mg kanamycin at 30° C. E. coli containing pRK2013 were grown overnight in kanamycin (50 µg/ml). This culture was started with several colonies. E. coli with pMON8439 were grown in LB with 75 µg/ml spectinomycin. After all of the cultures were grown, 4 ml of LB was added to a tube with 100 µl each of Agrobacterium ABI, pRK2013, and pMON8439. This mixture was centrifuged in a microfuge for 5 minutes and the supernatant fraction decanted. The pellet fraction was resuspended in the remaining liquid, and an aliquot was pipetted into the center of an LB plate. After overnight growth at 30° C. an aliquot of cells from this plate was streaked onto an LB plate supplemented with 75 µg/ml spectinomycin, 50 µg/ml kanamycin and 25 µg/ml chloramphenicol.

After 24–48 hours at 30° C. the plate from the triparental mating of pMON8439, pRK2013 and Agrobacterium ABI contained colonies, while the control plate from the mating of pMON8439 and ABI (without pRK2013, which is required For mobilization) did not contain colonies. After the triparental mating, 4 colonies were selected from the former plate, inoculated into a liquid culture of LB supplemented with 75 µg/ml spectinomycin, 50 µg/ml kanamycin and 25 µg/ml chloramphenicol and grown at 30° C. The presence of the PVX replicase gene was shown by DNA blot analysis. One of the cultures verified to contain PVX replicase was used for transformation of tobacco by the leaf disk transformation protocol.

11

The tobacco leaf disk transformation protocol uses healthy leaf tissue approximately one month old (Horsch et al. 1985). After a 15- to 20-minute surface sterilization of the leaves with a 10% v/v Clorox plus a surfactant, the leaves were rinsed 3 times in sterile water. Using a sterile paper punch, leaf discs were punched and placed upside down on MS104 media (4.3 g/l MS salts, 30 g/l sucrose, B5 vitamins, 0.1 mg/l NAA and 1.0 mg/l BA) for a 1 day preculture. Discs were then inoculated with an overnight culture of Agrobacterium ABI: pMON8439 that was diluted 1:5. The inoculation was done by placing the discs in centrifuge tubes with the culture. After 30 to 60 seconds, the liquid was drained off and the discs were blotted between sterile filter paper. Discs were then placed upside down on MS104 feeder plates with a filter disc to co-culture.

After 2–3 days of co-culture, discs were transferred, still upside down, to selection plates with MS104 media. After 2- to 3-weeks, calli formed, and individual clumps were separated from the leaf discs. Shoots were cleanly cut from the callus when they were large enough to distinguish from stems. The shoots were placed on hormone-free rooting media (MSO: MS salts, 30 g/l sucrose, and B5 vitamins) with selection. Roots formed in 1–2 weeks. Rooted shoots were placed in soil and were kept in a high humidity environment (e.g. plastic containers or bags). Shoots were hardened off by gradually exposing them to ambient humidity conditions.

Transgenic lines derived from transformation with pMON8439 were assayed by RNA blot analysis (Thomas, 1980) to determine the presence of PVX replicase mRNA corresponding to the predicted mRNA transcript expected from pMON8439. Transgenic plants with detectable PVX replicase RNA were allowed to self-fertilize and set seed. F1 progeny germinated from this seed were tested for resistance to infection by PVX. Prior to infection, the plants were screened by ELISA for the presence of neomycin phosphotransferase (NPTII). This test was essential because DNA inserted by *Agrobacterium mediated* transformation will segregate in the next generation in a Mendelian fashion. Thus, if one copy of the transferable region of plasmid pMON8439 is incorporated into plant genome, the F1 progeny of such an event will display a 3:1 phenotypic segregation for the transgenic trait (PVX replicase) and the selectable marker (NPTII).

Twenty plants that contained NPTII were selected from each plant line for PVX infection experiments. Nontransformed tobacco (*Nicotiana tabacum* var. samsun) was used as the control line. Plants were grown and tested in an environmentally controlled growth chamber with the following parameters: a 15 hour photoperiod (250 µEinsteins) at 25° C. followed by 9 hours of darkness at 22° C. Throughout the experiment, the chamber was held at 50% relative humidity. Ten of the twenty plants were inoculated with a low concentration of PVX (0.5 µg/ml), and the remaining ten plants were inoculated with, a high concentration of PVX (5.0 µg/ml). Only young plants, containing 5–6 small leaves, were inoculated. 50 µl of inoculum, in a 0.1M, pH 7.0 phosphate buffer, was lightly rubbed onto 2 leaves per plant that were pretreated with carborundum, which is a fine abrasive. This abrasive application slightly wounds the young leaves, and provides an enhanced opportunity for viral infection. Data from four replicase lines are shown in Table 1 (lines 29436, 30199, 30205 and 30219). Plants were monitored daily for visual signs of infection. At six days post infection (dpi), lesions of the inoculated leaves were counted (Table 1).

TABLE 1

| line | 0.5 µg/ml inoculum | 5.0 µg/ml inoculum |
|---|---|---|
| samsun | 13.3 (19.7) | 35.7 (24.4) |
| 29436 | 0.05† (0.22) | 0.15§ (0.37) |
| 30219 | 0.61† (1.0) | 6.3§ (7.2) |
| 30199 | 2.1† (2.8) | 17.2† (16) |
| 30205 | 1.5† (3.4) | 8.5§ (8) |

The mean number of lesions observed are shown for each of two inoculums per line. Sample standard deviations are shown parenthetically following the mean. The mean lesion counts from the transgenic lines were statistically compared to the control samsun line using the Student's t test, using a pooled estimate of variation. The † symbol indicates a statistically significant difference from the control at p=0.05; § indicates a statistically significant difference from the control at p=0.01.

To estimate virus levels in the inoculated and systemic leaves, a #8 sized cork borer, which yields circular samples weighing approximately 50 mg, was used to sample the plants. Inoculated leaves were sampled twice, at 6 and 14 dpi, and the second upper leaf was sampled three times, at 6, 11 and 14 dpi. Two #8 sized discs were taken at each sampling. Sampling the upper leaves estimates the extent of systemic infection. These leaf discs were analyzed for the presence of PVX coat protein (CP) antigen by ELISA. This assay is a quantitative estimation of virus titer. The results of this test are shown in FIGS. 6–9.

Figure 6:
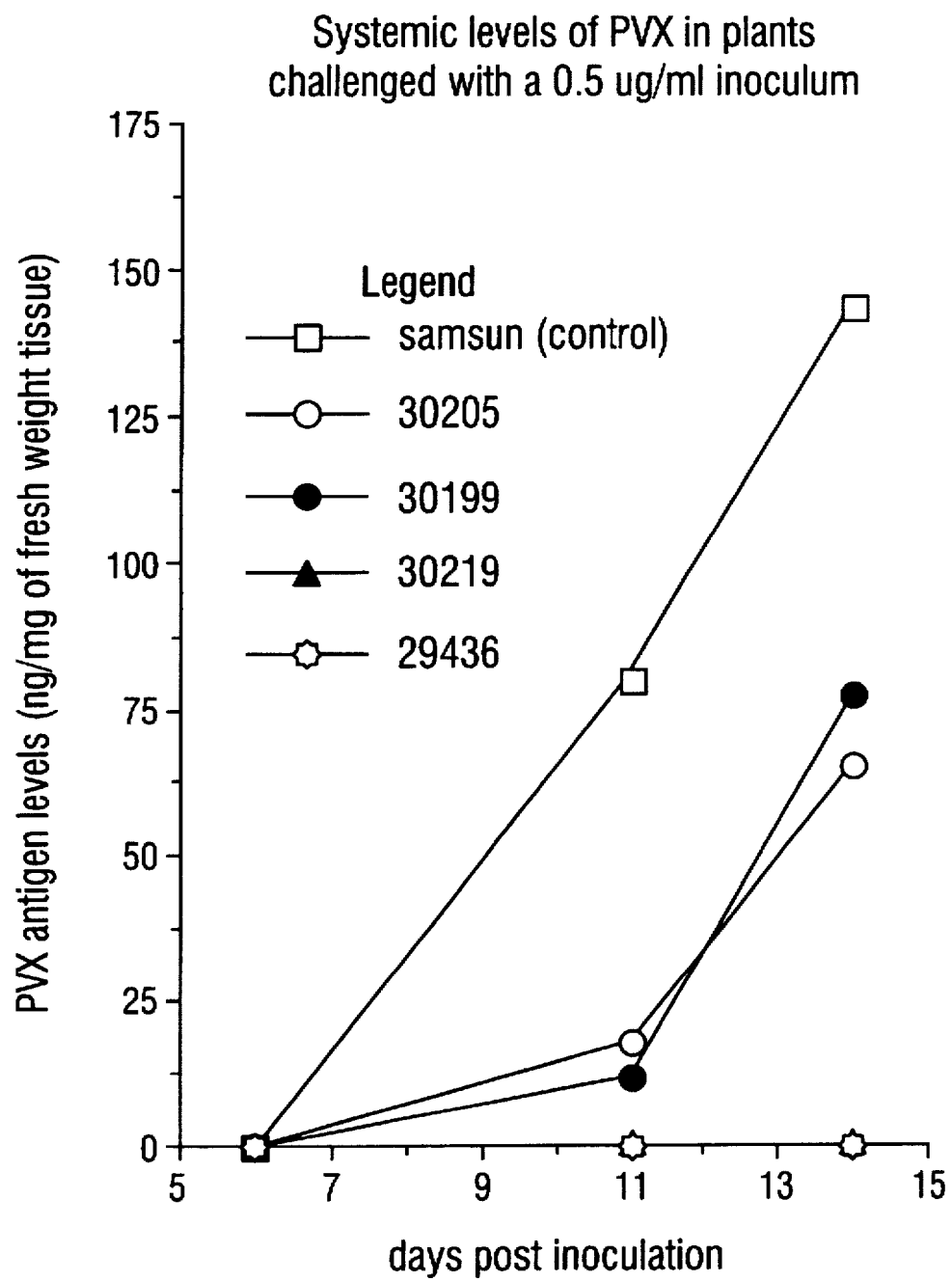
FIG. 6 is a graph illustrating the systemic viral antigen level of tobacco plant lines expressing the PVX replicase protein and control lines.
Figure 9:
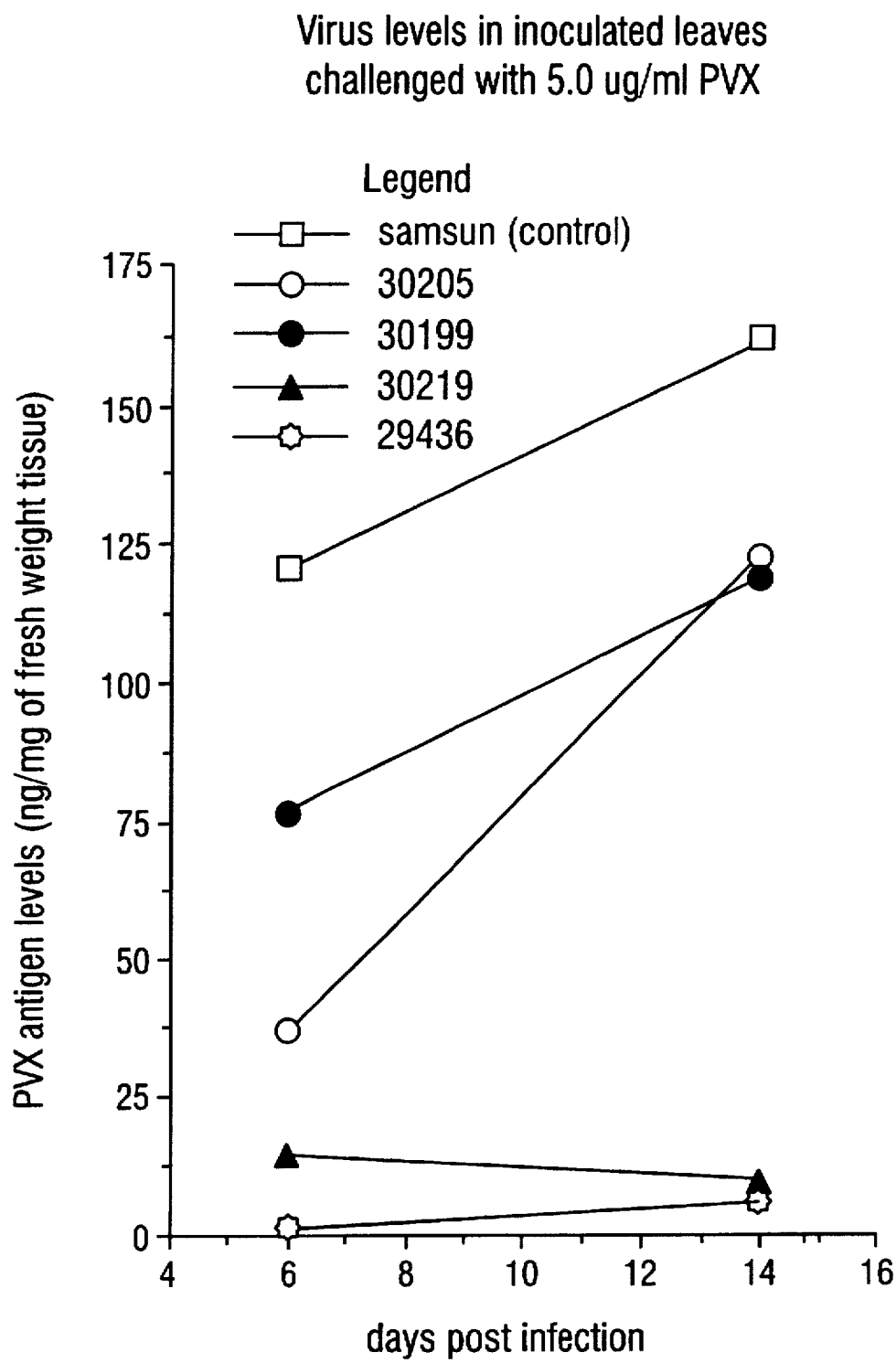
FIG. 9 is a graph illustrating the viral antigen level in inoculated leaves from tobacco plant lines expressing the PVX replicase protein and control lines.

FIG. 6 illustrates graphically the systemic levels of PVX in plants challenged with 0.5 µg/ml of PVX viral inoculum. FIG. 7 illustrates graphically the systemic levels of PVX in plants challenged with a 5.0 µg/ml PVX viral inoculum. FIG. 8 illustrates graphically the PVX antigen levels in inoculated leaves challenged with 0.5 µg/ml PVX viral inoculum. FIG. 9 illustrates graphically PVX antigen levels in inoculated leaves challenged with 5.0 µg/ml PVX viral inoculum. In FIGS. 6 and 7, the number of days post inoculation is plotted vs. PVX CP antigen levels measured in ng/mg fresh weight of tissue. In FIGS. 8 and 9, the number of days post infection is plotted vs. PVX CP antigen levels measured in ng/mg of fresh weight of tissue. As can be seen in FIGS. 6–9, the samsun control line became highly infected at each inoculum concentration, both in the inoculated and systemic leaves. This is a typical PVX infection, where the virus can accumulate to extremely high levels. At 14 dpi (days post infection), approximately 15% of the extractable protein in the systemic samsun leaves is PVX CP. In contrast, the best tobacco line expressing the PVX replicase gene, 29436, has been shown in a separate protection test to contain a 23,000-fold reduction in PVX levels compared to the samsun control. The tobacco lines expressing PVX replicase as shown in FIGS. 6–9 display two types of responses to PVX infection. For example, lines 29436 and 30219 consistently show a very low lev(e.l of PVX antigen at both inoculum concentrations in both the inoculated and upper leaves assayed. Lines 30205 and 30199 show a different type of resistance. While the PVX antigen level in these lines is consistently lower than the samsun control, this type of resistance is best described as a delay in virus infection.

EXAMPLE 2

A truncated PVX replicase gene, containing the native 84 nucleotide leader sequence (SEQ ID NO: 3) and the first 674 codons (SEQ ID NO: 6) is created by site-directed mutagenesis (Kunkel, 1985). The oligonucleotide primer necessary to create this truncated version of the PVX replicase allows for the insertion of a TAA stop codon and a SacI restriction endonuclease site between codons 674 and 675 (between an canine and methionine). The oligonucleotide primer is: 5' -GAATTGCTCGCTTAAGAGCTCATGAACAGAAGCC-3' (SEQ ID NO: 8).

Plasmid pMON8486 was created to test whether a portion of the PVX replicase gene could impart resistance to PVX infection when expressed in a plant. The oligonucleotide primer used to create this truncated version of the PVX replicase gene contains a SacI restriction endonuclease site, which facilitates cloning into a plant transformation vector. The oligonucleotide primer used was: 5' -GAATTGCTCGCTAAGAGCTCATGAACAGAAGCC-3' (SEQ ID NO: 10)

Figure 10:
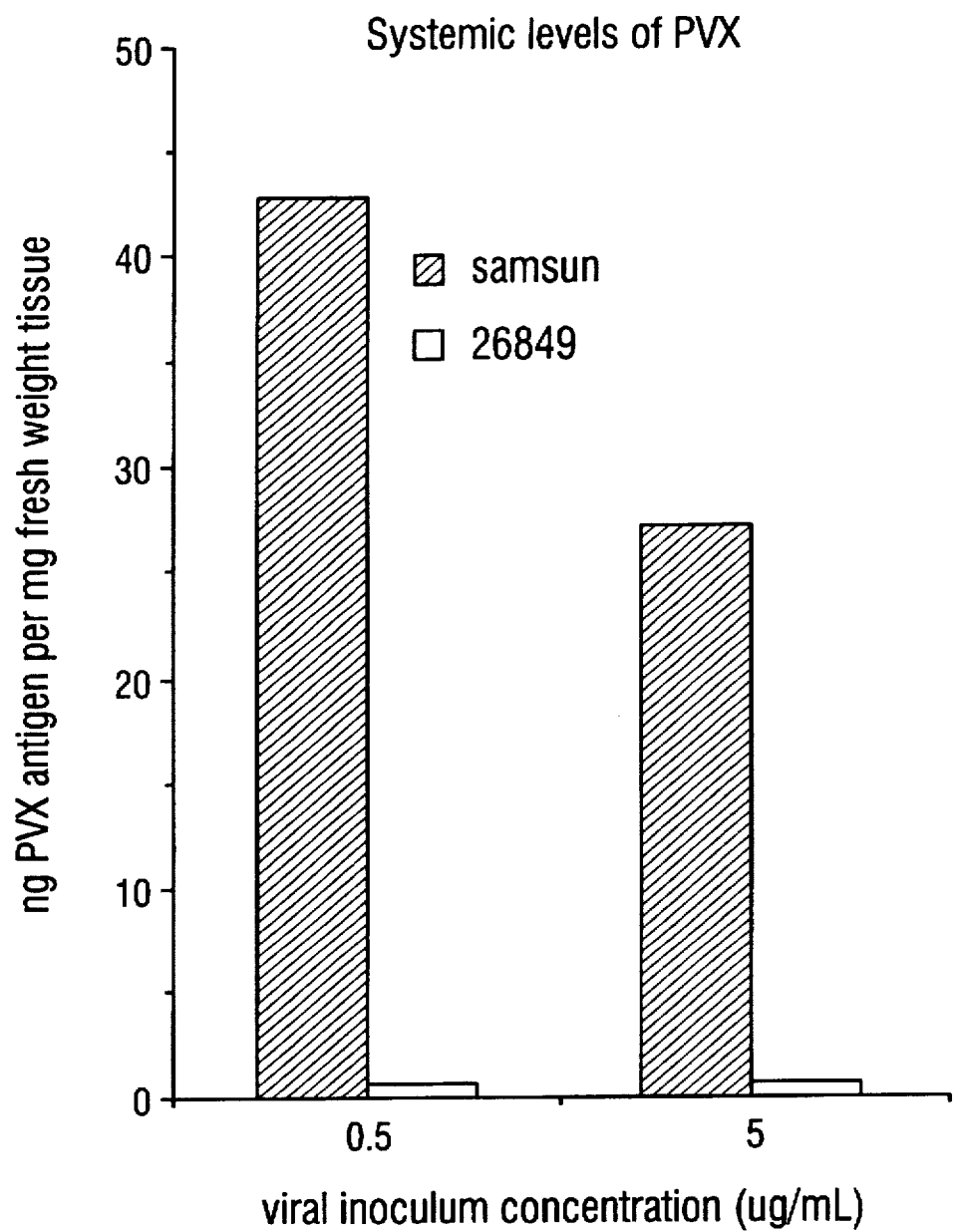
FIG. 10 is a graph illustrating the viral antigen level in a systemic leaf from tobacco plant lines expressing a truncated replicase protein and a control line.
Figure 11:
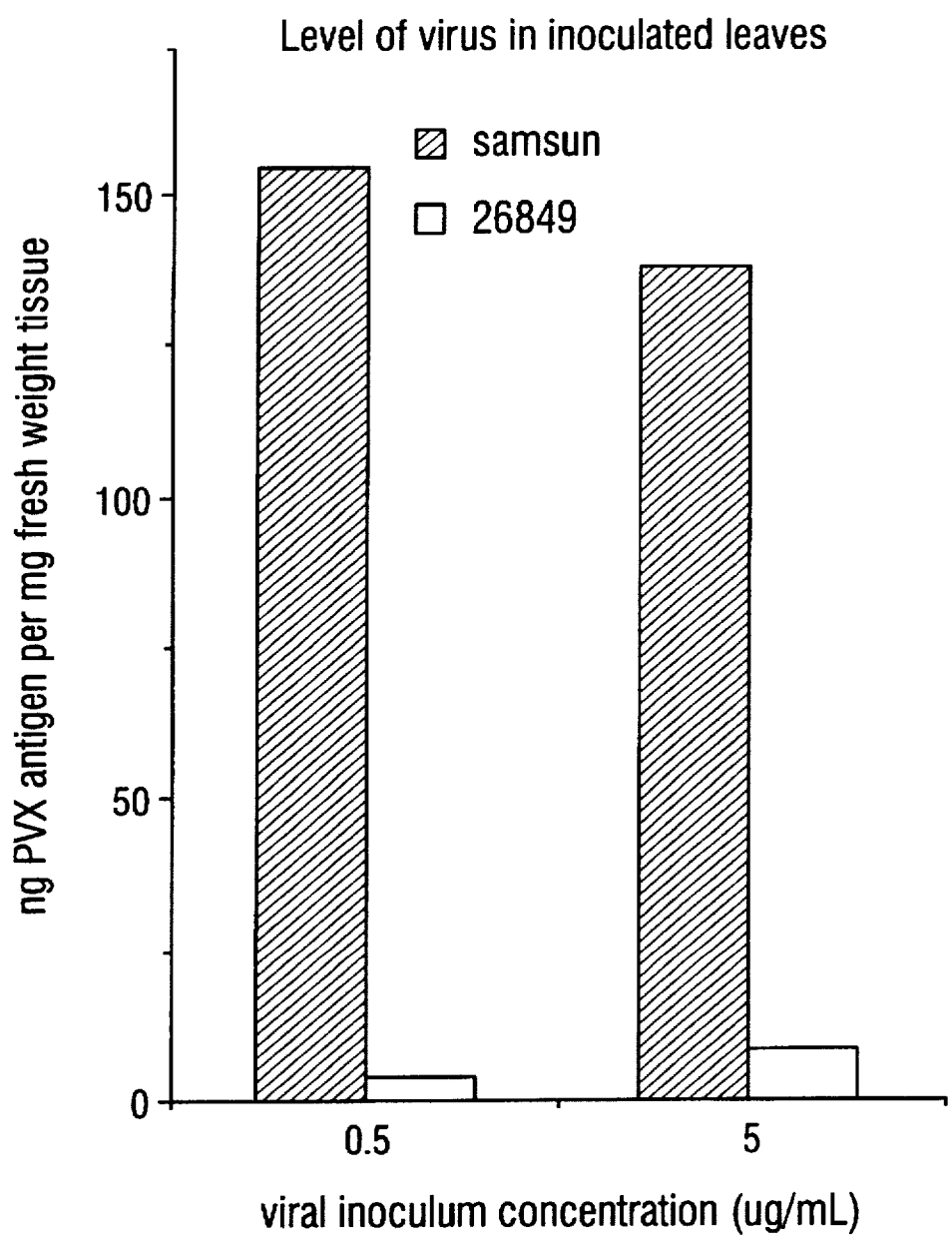
FIG. 11 is a graph illustrating the viral antigen level in inoculated leaves from tobacco plant lines expressing a truncated replicase protein and a control line.

This mutagenesis does not affect the first 674 amino acids of the PVX replicase protein from being translated. The 2215 bp SacI fragment of FIG. 2, containing approximately the first half of the replicase gene was cloned by standard methods into the pMON977 transformation vector. Because the replicase open reading frame was not terminated, the coding region extends into the E9 3' region of pMON977 by an additional 33 codons before a TGA stop codon terminates the open reading frame. The truncated PVX gene, which is extended by 33 codons is designated SEQ ID NO: 11, as shown in FIG. 13. The derived amino acid sequence of this extended gene is designated as SEQ ID NO: 12. Plasmid pMON8486 was mated with Agrobacterium and transformed into tobacco by the methods as described in Example 1. Expression analysis of primary transformants and protection tests were designed as described in Example 1. FIGS. 10 and 11 show that line 26849, which contains it truncated portion of the PVX replicase gene, is resistant to PVX infection when compared to the samsun control. In FIGS. 10 and 11, CP antigen levels, which are a measure of virus infection, are clearly reduced at two inoculum concentrations in both systemic and inoculated leaves. FIG. 10 represents the systemic level of PVX in plants challenged with 0.5 µg/ml PVX inoculum concentrations and 5 µg/ml PVX viral inoculum concentrations vs. ng PVX antigen per mg fresh weight of tissue. FIG. 11 represents the levels of PVX virus in inoculated leaves under the same conditions as described for FIG. 10. Ten NPTII positive F1 plants were used per inoculum concentration in the transgenic line.

EXAMPLE 3

The plant transformation vector pMON8439 containing a PVX replicase gene can be transformed into potato using the protocol described below.

Agrobacterium containing the desired plant transformation vector are grown overnight in 2 mls of LBSCK broth. LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0. The following day, the bacteria are diluted 1:10 with MSO or until an OD (optical density) reading of 0.2–0.3 is established. MSO contains 4.4 g MX salts (Sigma), 30 g sucrose and 2 ml $B_5$ vitamin (500 X) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma), 30 g sucrose, 0.17 g $NaH_2PO_4 \cdot H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10MSO with 1.5 mls of TxD cells overlayed with wetted filter paper. Approximately 50 explants are placed on each plate.

After a two (2) day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein (NPTII) which confers resistance to the antibiotic kanamycin to the plant. If the plant is positive for expression of the protein, the plant is kept for further study and maintained in tissue culture.

After the plant has been transformed and after transformed callus has been identified, the transformed callus tissue is regenerated into whole plants.

Potato plants derived from transformation with pMON8439 are screened by ELISA for the presence of neomycin phosphotransferase (NPTII) to identify transgenic potato plants. These plants are then assayed by RNA blot analysis (Thomas, 1980) to determine the presence of PVX replicase mRNA corresponding to the predicted mRNA transcript expected from pMON8439. Transgenic plants with detectable PVX RNA levels are then propagated by cuttings.

Twenty plants from each line are used in PVX protection experiments. Non-transformed Russet Burbank potato plants are used as control. Each plant is inoculated with 5 µg/ml PVX by applying 50 µl of inoculum in 0.1M phosphate buffer pH7.0, on two leaves per plant. Prior to inoculation, leaves are dusted with carborundum. Virus levels are quantitated by ELISA at 2, 3 and 4 weeks post inoculation as described in Example 1. Potato plants are selected that express the PVX replicase gene and exhibit resistance to infection by PVX.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth or shown in the accompanying drawing is to be interpreted as illustrative and not a limiting sense.

BIBLIOGRAPHY

Abel et al. (1986) *Science* 232: 738–743.
Bevan 1984 *Nucl.Acids Res.* 12: 8711–8721.
Coruzzi et al. (1990) *EMBO J.* 3:1671.
Cuozzo et al. (1988) *BioTechnol.* 6: 549–557.
deBokx (1972) Viruses of Potatoes and Seed-Potato Production. p. 233. Centre for Agric. Publ. and Documentation, Wageningen, The Netherlands.

deBokx (1986) Potato Virus Y. in: Compendium of Potato Diseases p. 7–71. W. Hooker ed. American Phytopathology Society. Ditta et al. (1980) *Proc. Natl. Acad. Sci.* USA 77: 7347–7351.
Fling et al. (1985) *Nucl.Acids Res.* 13: 7095–7106.
Fraley et al. (1983) *Proc. Natl. Acad. Sci.* USA80: 4803–4807.
Golemboski et al. (1990) *Proc. Natl. Acad. Sci.* USA 87: 6311–6315.
Hemenway et al. (1988) *EMBO J.* 7: 1273–12.80.
Hemenway et al. (1990) *Virology* 175: 365–1971.
Herrera-Estrell (1983) *Nature* 303: 209.
Hodgman (1988) *Nature* 333: 22–23.
Horsch et al. (1985) *Science* 227: 1229–1231.
Huisman et al. (1988) *J. Gen. Virol.* 69: 1789–1798.
Ishikawa et al. (1986) *Nucleic Acids Res.* 14: 8291–8305.
Kaniewski et al. (1990) *Biotechnol.* 8:750–754.
Kay et al. (1987) *Science* 236: 1299–1302.
Klee et al. (1985) *BioTechnol.* 3: 637–642.
Koncz and Schell (1986) *Mol. Gen. Genet.* 204: 383–396.
Kunkel (1985) *Proc. Natl. Acad. Sci.* USA 82: 488–492.
Lawson et al. (1990) *BioTechnol.* 8: 127–134.
Odell et al. (1985) *Nature* 313: 810–812.
Purcifull and Edwardson (1981) in: Handbook of Plant Virus Infections and Comparative Diagnosis. E. Kurstak (ed). Elsevier/North Holland Biomedical Press.
Skryabin et al. (1988) *FEBS Lett.* 240: 3340.
Stalker et al. (1981) *Mol. Gen. Genet.* 181: 8–12.
Stark and Beachy (1989) *BioTechnol.* 7: 1257.1262.
Taschner et al. (1991) *Virology* 181: 445–450.
Todd, (1957) *Proc 3rd Conf. Potato Virus Diseases* p. 132. Lisse-Wageninger, The Netherlands.
Thomas (1980) *Proc. Natl. Acad. Sci.* USA 77: 5201–5205.
Turner et al. (1987) *EMBO J.* 6:1181–1188.
van Dun et al. (1988) *Virology* 163: 572–578.
van Dun et al. (1988) *Virology* 164: 383–389.
Zuidema et al. (1980) *J. Gen. Virol.* 70: 267–276.

What is claimed is:

1. A double stranded DNA molecule comprising:
   a promoter which functions in plant cells to cause the production of an RNA sequence; which is operably linked to a fragment encoding an N-terminal portion of PVX replicase which consists essentially of SEQ ID NO:6; which is operably linked to a 3' non-translated DNA sequence that functions in plants to cause the polyadenylation of the 3' end of the transcribed mRNA sequence.

2. The double stranded DNA molecule of claim 1 wherein said promoter is selected from the group consisting of the FMV35S promoter, the CaMV35S promoter and the enhanced CaMV35S promoter.

3. A transgenic potato plant cell which contain in its genome the double stranded DNA molecule of claim 1.

4. A transgenic potato tuber comprising cells of claim 3.

5. A method for providing resistance in Solanaceae plants to infection by PVX comprising the steps of:
   stably transforming cells of a Solanaceae plant with the double stranded DNA molecule of claim 1; and selecting transformed plants which express SEQ ID NO:6 at a level sufficient to render the plants resistant to infection by PVX.

6. A method according to claim 5 wherein said Solanaceae plant is selected from the group consisting of potato and tomato.

7. A method according to claim 5 wherein said plant is potato.

8. A transgenic potato plant comprising potato plant cells of claim 5.

* * * * *